United States Patent
Pfeifer et al.

(10) Patent No.: US 11,541,110 B2
(45) Date of Patent: Jan. 3, 2023

(54) COMPREHENSIVE VACCINE DESIGN FOR COMMENSAL DISEASE PROGRESSION

(71) Applicant: The Research Foundation for The State University of New York, Amherst, NY (US)

(72) Inventors: Blaine Pfeifer, Buffalo, NY (US); Charles Jones, North Tonawanda, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 229 days.

(21) Appl. No.: 16/755,537

(22) PCT Filed: Oct. 12, 2018

(86) PCT No.: PCT/US2018/055676
§ 371 (c)(1),
(2) Date: Apr. 10, 2020

(87) PCT Pub. No.: WO2019/075372
PCT Pub. Date: Apr. 18, 2019

(65) Prior Publication Data
US 2020/0376108 A1   Dec. 3, 2020

Related U.S. Application Data

(60) Provisional application No. 62/670,419, filed on May 11, 2018, provisional application No. 62/572,081, filed on Oct. 13, 2017.

(51) Int. Cl.
| | | |
|---|---|---|
| *A01N 63/00* | (2020.01) | |
| *A61K 39/09* | (2006.01) | |
| *A61K 9/127* | (2006.01) | |
| *A61K 39/00* | (2006.01) | |

(52) U.S. Cl.
CPC .......... *A61K 39/092* (2013.01); *A61K 9/1271* (2013.01); *A61K 2039/55555* (2013.01); *A61K 2039/6037* (2013.01); *A61K 2039/6068* (2013.01); *A61K 2039/622* (2013.01); *A61K 2039/625* (2013.01)

(58) Field of Classification Search
CPC .................................................. A61K 39/092
See application file for complete search history.

(56) References Cited

U.S. PATENT DOCUMENTS

| | | |
|---|---|---|
| 7,005,139 B2 | 2/2006 | Wong et al. |
| 8,753,647 B2 | 6/2014 | Bacon et al. |
| 9,289,488 B2 | 3/2016 | Hickman et al. |
| 9,499,593 B2 | 11/2016 | Malley et al. |
| 9,724,401 B2 | 8/2017 | Killeen et al. |
| 9,750,692 B2 | 9/2017 | Bacon et al. |
| 2002/0122820 A1 | 9/2002 | Hildebrand et al. |
| 2004/0202668 A1 | 10/2004 | Boutriau et al. |
| 2014/0248337 A1 | 9/2014 | Bacon et al. |
| 2016/0090404 A1 | 3/2016 | Malley et al. |

FOREIGN PATENT DOCUMENTS

| | | |
|---|---|---|
| CN | 101024079 A | 8/2007 |
| EP | 1768647 B1 | 8/2012 |
| EP | 2514410 B1 | 5/2016 |
| EP | 2056871 B1 | 11/2017 |
| WO | 00/63385 A2 | 10/2000 |
| WO | 2007/039583 A1 | 4/2007 |
| WO | 2007/039584 A1 | 4/2007 |
| WO | 2011/103588 A1 | 8/2011 |
| WO | 2013/153179 A1 | 10/2013 |
| WO | 2017/067962 A1 | 4/2017 |
| WO | 2017/176833 A1 | 10/2017 |

OTHER PUBLICATIONS

Jones, C.H., et al., Comprehensive vaccine design for commensal disease progression; Science Advances, Oct. 18, 2017, vol. 3, e1701797, pp. 1-8.
Hill, A., et al., Engineering a next-generation flycoconjugate-like *Streptococcus pneumoniea* vaccine, Infections Diseases, Sep. 4, 2018, vol. 4, No. 11, pp. 1553-1563.
Colino, J., et al., Noncovalent Association of Protein and Capsular Polysaccharide on Bacteria-Sized Latex Beads as a Model for Polysaccharide-Specific Humoral Immunity to Intact Gram-Positive Extracellular Bacteria, Journal of Immunology, Aug. 7, 2013, vol. 191, No. 6, pp. 3254-3263.
Tada, R., et al., Nasal vaccination with pneumococcal surface protein A in combination with cationic liposomes consisting of DOTAP and DC-chol confers antigen-mediated protective immunity against *Streptococcus pneumoniae* infections in mice, International Immunopharmacology, Aug. 2018, vol. 61, pp. 385-393.
Chen, M., et al., A versatile drug delivery system using streptavidin-tagged pegylated liposomes and biotinylated biomaterials, International Journal of Pharmaceutics, Jun. 24, 2013, vol. 454, pp. 478-485.
Li, Y, et al., Directed vaccination against pneumococcal disease, Proc Natl Acad Sci, Jun. 6, 2016, vol. 113, No. 25, pp. 6898-6903.
Li, Y, et al., In situ pneumococcal vaccine production and delivery through a hybrid biological-biomaterial vector. Science Advances, Jul. 1, 2016, vol. 2, No. 7, article e1600264, 9 pages.

*Primary Examiner* — Albert M Navarro
*Assistant Examiner* — Mark Navarro
(74) *Attorney, Agent, or Firm* — Hodgson Russ LLP

(57) ABSTRACT

Provided are vaccine compositions and methods against *Streptococcus pneumoniae*. The composition comprises liposomes which have polysaccharides from one or more serotypes and have proteins non-covalently attached to the surface and exposed to the exterior.

20 Claims, 37 Drawing Sheets
Specification includes a Sequence Listing.

Table S1

| Serotype / Vaccine | PCV13 | PPSV23 | LEPS (20V) |
|---|---|---|---|
| 1 | 129 | 88 | 40 |
| 2 | --- | 77 | 85 |
| 3 | 98 | 23 | 101 |
| 4 | 34 | 45 | 136 |
| 5 | 47 | 67 | 38 |
| 6A | 55 | --- | 169 |
| 6B | 39 | 26 | 151 |
| 7F | 240 | 29 | 151 |
| 8 | --- | 65 | 98 |
| 9N | --- | 52 | 15 |
| 9V | 176 | 114 | 117 |
| 10A | --- | 128 | --- |
| 11A | --- | 94 | --- |
| 12F | --- | 34 | 128 |
| 14 | 88 | 36 | 44 |
| 15B | --- | 143 | --- |
| 17F | --- | 112 | 101 |
| 18C | 222 | 46 | 156 |
| 19A | 120 | 147 | 154 |
| 19F | 144 | 49 | 243 |
| 20 | --- | 37 | 75 |
| 22F | --- | 77 | 149 |
| 23F | 331 | 13 | 69 |
| 33F | --- | 16 | --- |

Figure 15

Table S2

| Serotype | PCV13 Planktonic | PCV13 BFR | PPSV23 Planktonic | PPSV23 BFR | PncO + GlpO; Alum Planktonic | PncO + GlpO; Alum BFR |
|---|---|---|---|---|---|---|
| 1 | 129 | --- | 88 | --- | --- | 15 |
| 2 | --- | --- | 77 | --- | --- | 122 |
| 3 | 98 | --- | 23 | --- | --- | 160 |
| 4 | 34 | --- | 45 | --- | --- | 430 |
| 5 | 47 | --- | 67 | --- | --- | 339 |
| 6A | 55 | --- | --- | --- | --- | 87 |
| 6B | 39 | --- | 26 | --- | --- | 18 |
| 6C | --- | --- | --- | --- | --- | 276 |
| 6D | --- | --- | --- | --- | --- | 370 |
| 7A | --- | --- | --- | --- | --- | 169 |
| 7B | --- | --- | --- | --- | --- | 99 |
| 7C | --- | --- | 29 | --- | --- | 145 |
| 7F | 240 | --- | 65 | --- | --- | 45 |
| 8 | --- | --- | 52 | --- | --- | 61 |
| 9A | --- | --- | --- | --- | --- | 96 |
| 9N | 176 | --- | 114 | --- | --- | 348 |
| 9V | --- | --- | 128 | --- | --- | 382 |
| 10A | --- | --- | --- | --- | --- | 51 |
| 10F | --- | --- | --- | --- | --- | 26 |
| 11A | --- | --- | 94 | --- | --- | 63 |
| 11B | --- | --- | --- | --- | --- | 61 |
| 11C | --- | --- | --- | --- | --- | 85 |
| 12A | --- | --- | --- | --- | --- | 94 |
| 12B | --- | --- | --- | --- | --- | 288 |
| 12F | --- | --- | 34 | --- | --- | 366 |
| 13 | --- | --- | --- | --- | --- | 103 |
| 14 | 88 | --- | 36 | --- | --- | 221 |
| 15A | --- | --- | --- | --- | --- | 51 |
| 15B | --- | --- | 143 | --- | --- | 368 |
| 15C | --- | --- | --- | --- | --- | 253 |
| 15F | --- | --- | --- | --- | --- | 166 |
| 16A | --- | --- | --- | --- | --- | 184 |
| 16F | --- | --- | --- | --- | --- | 202 |
| 17A | --- | --- | --- | --- | --- | 248 |
| 17F | --- | --- | 112 | --- | --- | 196 |
| 18A | --- | --- | --- | --- | --- | 139 |
| 18B | --- | --- | --- | --- | --- | 275 |
| 18C | 222 | --- | 46 | --- | --- | 339 |
| 18F | --- | --- | --- | --- | --- | 190 |
| 19A | 120 | --- | 147 | --- | --- | 62 |
| 19C | --- | --- | --- | --- | --- | 183 |
| 19F | 144 | --- | 49 | --- | --- | 339 |
| 20 | --- | --- | 37 | --- | --- | 214 |
| 21 | --- | --- | --- | --- | --- | 266 |
| 22A | --- | --- | --- | --- | --- | 325 |
| 22F | --- | --- | 77 | --- | --- | 366 |
| 23A | --- | --- | --- | --- | --- | 77 |
| 23B | --- | --- | --- | --- | --- | 353 |
| 23F | 331 | --- | 13 | --- | --- | 273 |
| 24A | --- | --- | --- | --- | --- | 24 |
| 24B | --- | --- | --- | --- | --- | 281 |
| 24F | --- | --- | --- | --- | --- | 75 |
| 25F | --- | --- | --- | --- | --- | 236 |
| 27 | --- | --- | --- | --- | --- | 110 |
| 28A | --- | --- | --- | --- | --- | 235 |
| 28F | --- | --- | --- | --- | --- | 351 |
| 29 | --- | --- | --- | --- | --- | 90 |
| 30 | --- | --- | --- | --- | --- | 292 |
| 31 | --- | --- | --- | --- | --- | 186 |
| 33A | --- | --- | --- | --- | --- | 353 |
| 33F | --- | --- | 16 | --- | --- | 186 |
| 34 | --- | --- | --- | --- | --- | 352 |
| 35A | --- | --- | --- | --- | --- | 97 |
| 35B | --- | --- | --- | --- | --- | 52 |
| 35C | --- | --- | --- | --- | --- | 186 |
| 35F | --- | --- | --- | --- | --- | 31 |
| 37 | --- | --- | --- | --- | --- | 177 |
| 38 | --- | --- | --- | --- | --- | 81 |
| 39 | --- | --- | --- | --- | --- | 186 |
| 41A | --- | --- | --- | --- | --- | 352 |
| 47F | --- | --- | --- | --- | --- | 186 |

Figure 16

Table S3

| Gene | Size (aa) | Function |
|---|---|---|
| GlpO | 609 | α-glycerophosphate oxidase |
| PncO | 230 | Bacteriocin ABC transporter transmembrane protein |

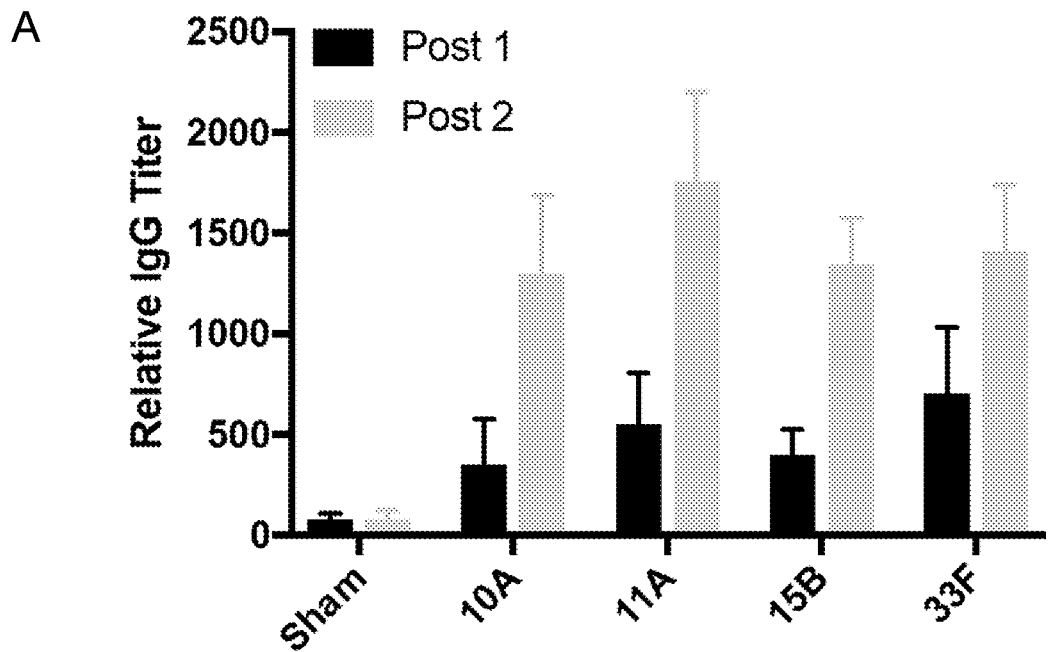
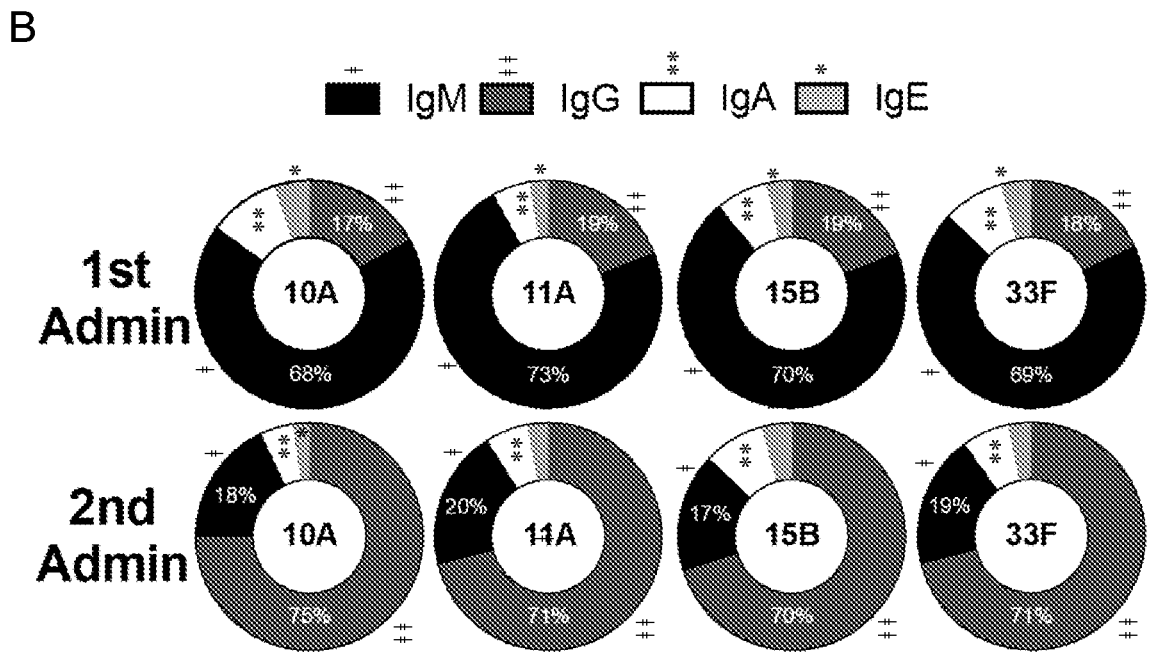
Figure 22

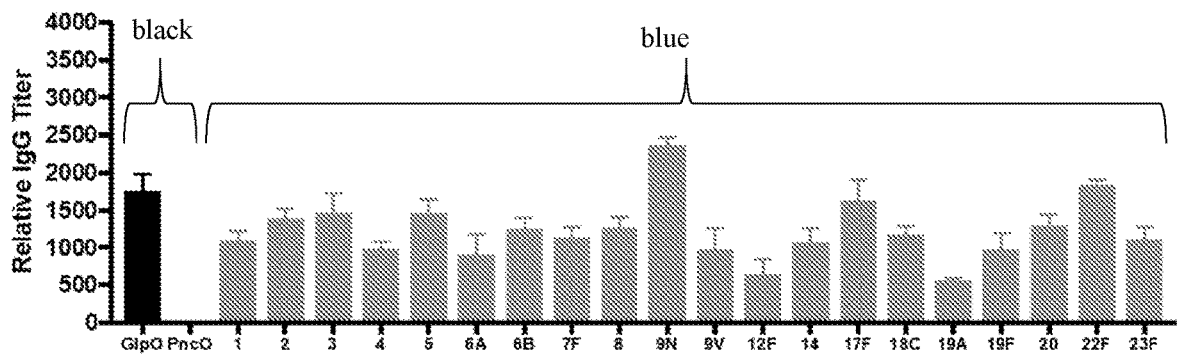
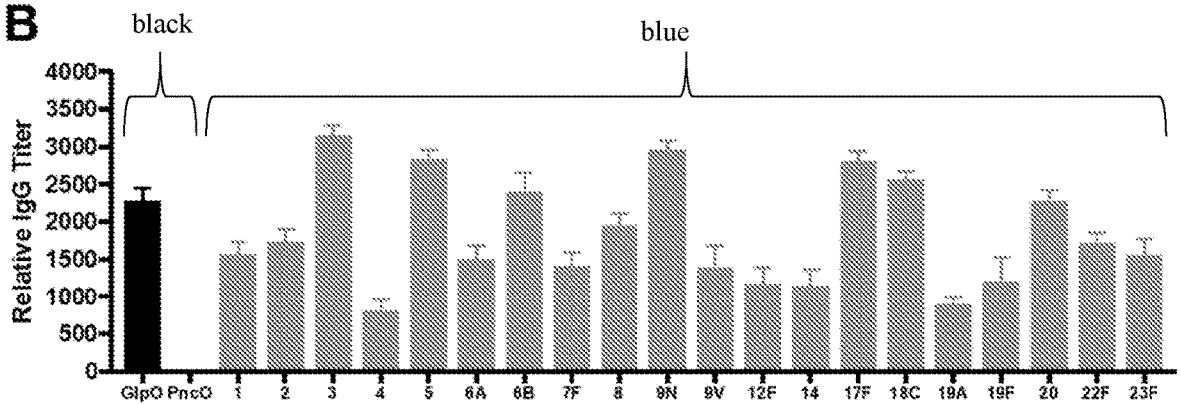
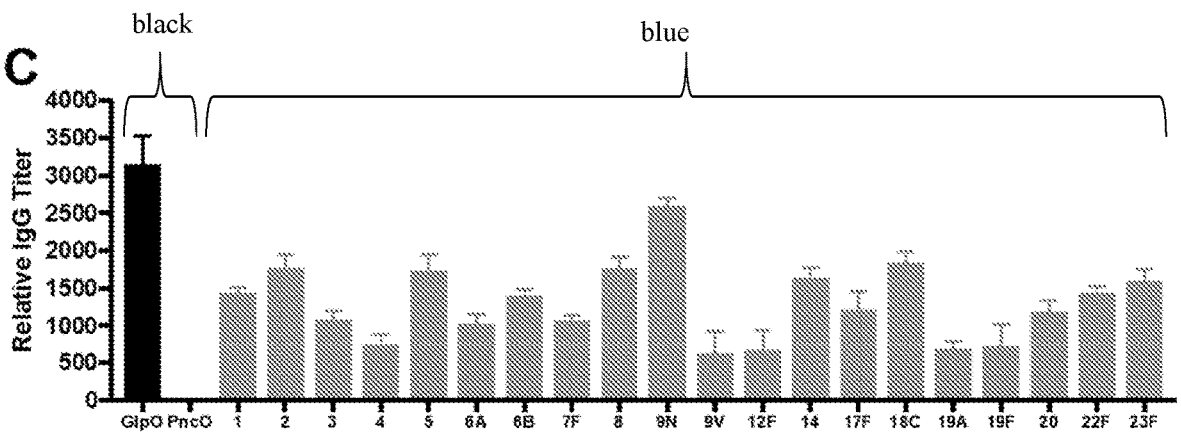
Figure 25

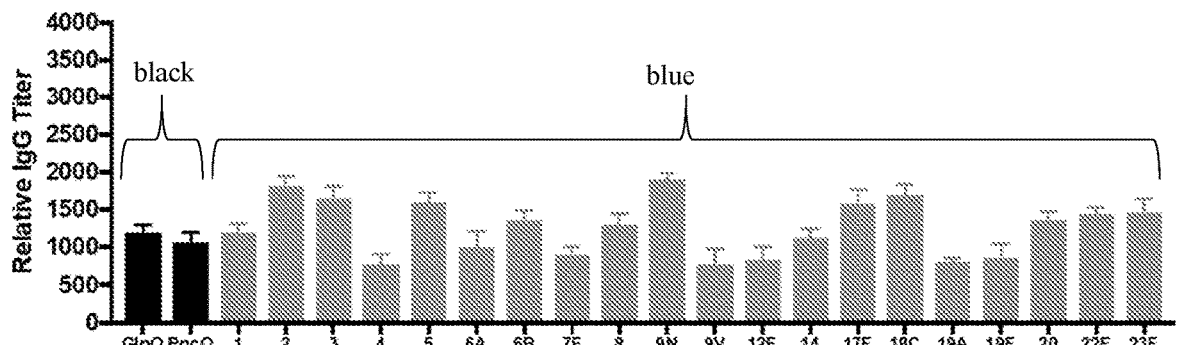
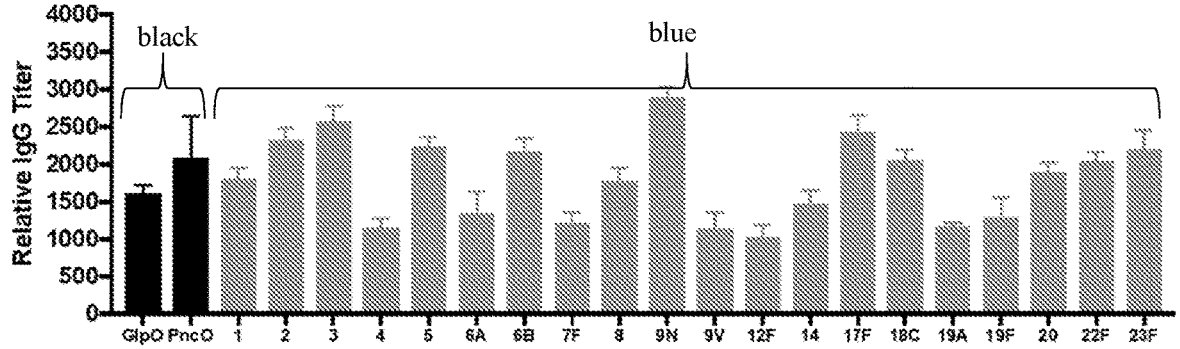
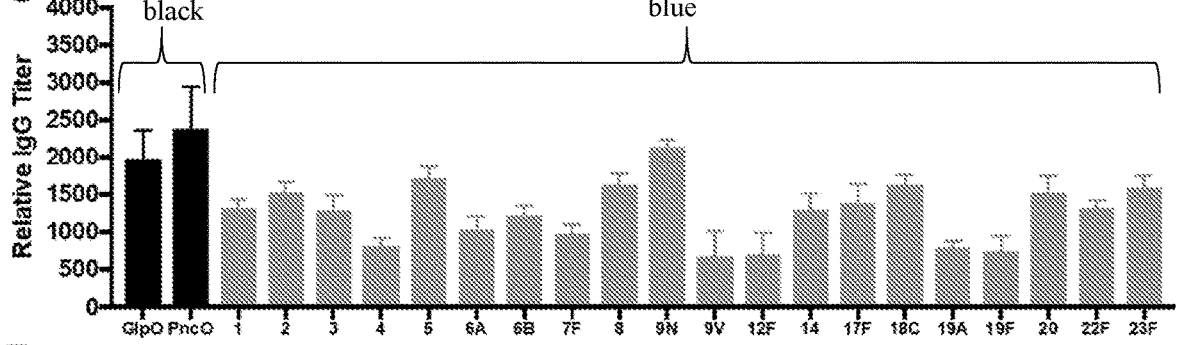
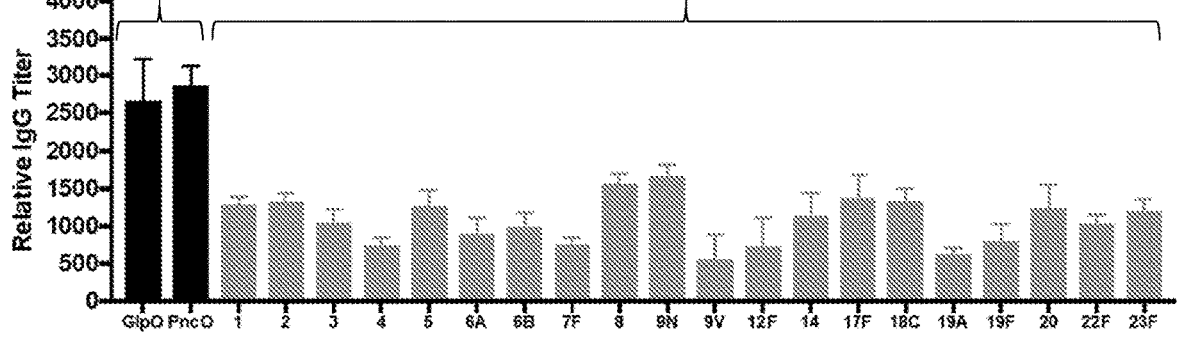
Figure 26

Supplementary Table 4: Microfloral bacteria with GlpO homologs tested for cross-reactivity with percent homology of protein regions indicated

| Species | Colonization Location | Full-Length | Average Homology Surface-Accessible | Epitope |
|---|---|---|---|---|
| *Streptococcus mitis* * | Oral Cavity, Throat, Nasopharynx | 98% | 92% | 99% |
| *Streptococcus oralis* | Oral Cavity | 97% | 97% | 99% |
| *Streptococcus infantis* * | Upper Respiratory | 97% | 97% | 97% |
| *Streptococcus cristatus* | Oral Cavity | 95% | 95% | 95% |
| *Streptococcus parasanguinis* | Oral Cavity | 93% | 92% | 95% |
| *Streptococcus sanguinis* | Oral Cavity | 94% | 94% | 95% |
| *Streptococcus gordonii* | Oral Cavity | 95% | 94% | 94% |
| *Streptococcus salivarius* | Oral Cavity, Upper Respiratory | 94% | 94% | 93% |
| *Streptococcus dysgalactiae* * | Gastrointestinal and Genitourinary Tract | 75% | 75% | 73% |
| *Streptococcus pyogenes* | Upper Respiratory, Skin | 75% | 74% | 72% |
| *Lactobacillus iners* | Vaginal Tract | 63% | 64% | 70% |
| *Streptococcus agalactiae* ** | Gastrointestinal and Genitourinary Tract | 71% | 72% | 68% |
| *Alloiococcus otitis* * | Nasopharynx | 64% | 64% | 64% |
| *Enterococcus durans* | Gastrointestinal Tract | 61% | 61% | 64% |
| *Lactobacillus plantarum* ** | Gastrointestinal Tract | 62% | 63% | 62% |
| *Enterococcus faecalis* * | Gastrointestinal Tract | 63% | 63% | 62% |
| *Lactobacillus salivarius* ** | Gastrointestinal Tract | 60% | 59% | 61% |
| *Aerococcus christensenii* * | Vaginal Tract | 60% | 62% | 61% |
| *Pediococcus acidilactici* ** | Gastrointestinal Tract | 58% | 58% | 58% |
| *Lactobacillus pentosus* | Vaginal Tract, Gastrointestinal Tract | 63% | 62% | 58% |

*Evaluated for antibody binding via immunofluorescence assay
**Evaluated for antibody binding and neutralization activity using OPA assay

Figure 27

Figure 28: Supplementary Table 5: Complete OPA data for LEPS(20V):PncO dose escalation Supplementary Table 5 (continued): Complete OPA data for LEPS(20V):PncO dose escalation

| Serotype | PCV13 | | PPSV23 | | LEPS(20V):PncO (34 µg) | | LEPS(20V):PncO (68 µg) | | LEPS(20V):PncO (136 µg) | |
|---|---|---|---|---|---|---|---|---|---|---|
| | Planktonic | BFR | Planktonic | BFR | Planktonic | BFR | Planktonic | BFR | Planktonic | BFR |
| 18A | --- | --- | --- | --- | --- | 133 | --- | 264 | --- | 163 |
| 18B | --- | --- | --- | --- | --- | 305 | --- | 163 | --- | 379 |
| 18C | 180 | --- | 48 | --- | 312 | 323 | 282 | 333 | 245 | 612 |
| 18F | --- | --- | --- | --- | --- | 173 | --- | 320 | --- | 198 |
| 19A | 180 | --- | 134 | --- | 180 | 76 | 243 | 185 | 224 | 96 |
| 19C | --- | --- | --- | --- | --- | 172 | --- | 75 | --- | 207 |
| 19F | 200 | --- | 55 | --- | 320 | 322 | 343 | 217 | 323 | 513 |
| 20 | --- | --- | 43 | --- | 102 | 201 | 132 | 412 | 122 | 145 |
| 21 | --- | --- | --- | --- | --- | 322 | --- | 462 | --- | 480 |
| 22A | --- | --- | --- | --- | --- | 408 | --- | 412 | --- | 652 |
| 22F | --- | --- | 79 | --- | 201 | 412 | 222 | 511 | 253 | 545 |
| 23A | --- | --- | --- | --- | --- | 72 | --- | 66 | --- | 70 |
| 23B | 170 | --- | --- | --- | --- | 353 | --- | 504 | --- | 615 |
| 23F | --- | --- | 15 | --- | 81 | 303 | 97 | 570 | 106 | 365 |
| 24A | --- | --- | --- | --- | --- | 21 | --- | 66 | --- | 21 |
| 24B | --- | --- | --- | --- | --- | 284 | --- | 455 | --- | 229 |
| 24F | --- | --- | --- | --- | --- | 80 | --- | 176 | --- | 96 |
| 27 | --- | --- | --- | --- | --- | 269 | --- | 217 | --- | 328 |
| 28A | --- | --- | --- | --- | --- | 108 | --- | 283 | --- | 151 |
| 28F | --- | --- | 20 | --- | --- | 214 | --- | 141 | --- | 190 |
| 29 | --- | --- | --- | --- | --- | 328 | --- | 192 | --- | 410 |
| 31 | --- | --- | --- | --- | --- | 271 | --- | 351 | --- | 127 |
| 33A | --- | --- | --- | --- | --- | 106 | --- | 98 | --- | 249 |
| 33F | --- | --- | --- | --- | --- | 401 | --- | 261 | --- | 480 |
| 34 | --- | --- | --- | --- | --- | 199 | --- | 361 | --- | 241 |
| 35A | --- | --- | --- | --- | --- | 120 | --- | 217 | --- | 414 |
| 35B | --- | --- | --- | --- | --- | 108 | --- | 129 | --- | 115 |
| 35C | --- | --- | --- | --- | --- | 61 | --- | 109 | --- | 100 |
| 35F | --- | --- | --- | --- | --- | 212 | --- | 240 | --- | 308 |
| 37 | --- | --- | --- | --- | --- | 72 | --- | 42 | --- | 42 |
| 38 | --- | --- | --- | --- | --- | 161 | --- | 187 | --- | 211 |
| 39 | --- | --- | --- | --- | --- | 92 | --- | 109 | --- | 118 |
| 41A | --- | --- | --- | --- | --- | 371 | --- | 224 | --- | 386 |
| 42 | --- | --- | --- | --- | --- | 320 | --- | 224 | --- | 415 |
| 45 | --- | --- | --- | --- | --- | 188 | --- | 349 | --- | 279 |

Figure 28 (cont.)

Supplementary Table 6: Complete OPA data for LEPS(20V):GlpO+PncO dose escalation

Figure 29

Supplementary Table 6 (continued): Complete OPA data for LEPS(20V):GlpO+PncO dose escalation

Figure 29 (cont.)

Supplementary Table 7: LEPS(24V):PncO planktonic serotype OPA data

| Serotype | PCV13 | PPSV23 | LEPS(24V):CRM197 | LEPS(24V):PncO |
|---|---|---|---|---|
| 1 | 150 | 126 | 156 | 178 |
| 2 | --- | 101 | 129 | 134 |
| 3 | 120 | 30 | 110 | 113 |
| 4 | 48 | 51 | 211 | 209 |
| 5 | 56 | 92 | 105 | 210 |
| 6A | 59 | --- | 254 | 312 |
| 6B | 50 | 30 | 217 | 217 |
| 7F | 180 | 33 | 169 | 186 |
| 8 | --- | 81 | 147 | 181 |
| 9N | --- | 59 | 88 | 108 |
| 9V | 187 | 125 | 165 | 148 |
| 10A | --- | 150 | 178 | 196 |
| 11A | --- | 96 | 205 | 205 |
| 12F | --- | 38 | 179 | 186 |
| 14 | 105 | 37 | 165 | 172 |
| 15B | --- | 172 | 146 | 146 |
| 17F | --- | 110 | 155 | 154 |
| 18C | 180 | 48 | 257 | 272 |
| 19A | 180 | 134 | 211 | 232 |
| 19F | 200 | 55 | 210 | 189 |
| 20 | --- | 43 | 114 | 139 |
| 22F | --- | 79 | 255 | 232 |
| 23F | 170 | 15 | 182 | 189 |
| 33F | --- | 20 | 205 | 262 |

Figure 30

Supplementary Table 8: Size and charge characterization of LEPS variants

| Attachment Strategy | Size (nm) | Zeta Potential (mV) |
|---|---|---|
| [Ni-NTA] | | |
| Empty | 110.0 ± 17.6 | -11.0 ± 1.4 |
| 20-Valent | 193.5 ± 13.8 | -10.2 ± 2.8 |
| 20-Valent + Protein | 179.2 ± 20.6 | -17.9 ± 2.2 |
| 24-Valent | 249.1 ± 9.0 | -12.3 ± 1.6 |
| 24-Valent + Protein | 286.7 ± 20.2 | -15.9 ± 2.7 |
| [Co-NTA] | | |
| Empty | 113.3 ± 22.5 | -9.8 ± 1.7 |
| 20-Valent | 181.9 ± 14.2 | -11.8 ± 3.2 |
| 20-Valent + Protein | 225.8 ± 16.5 | -17.5 ± 2.4 |
| 24-Valent | 221.3 ± 10.8 | -11.8 ± 1.6 |
| 24-Valent + Protein | 237.9 ± 17.8 | -13.5 ± 3.4 |
| BSB | | |
| Empty | 128.5 ± 14.2 | -13.7 ± 2.3 |
| 20-Valent | 249.2 ± 18.9 | -16.4 ± 2.0 |
| 20-Valent + Protein | 207.1 ± 19.7 | -23.1 ± 2.7 |
| 24-Valent | 255.3 ± 13.6 | -16.4 ± 1.9 |
| 24-Valent + Protein | 275.4 ± 21.9 | -22.2 ± 1.8 |
| BS | | |
| Empty | 138.0 ± 16.3 | -15.5 ± 2.6 |
| 20-Valent | 225.3 ± 11.6 | -14.1 ± 2.0 |
| 20-Valent + Protein | 232.5 ± 19.2 | -20.5 ± 1.4 |
| 24-Valent | 256.3 ± 16.0 | -16.6 ± 2.4 |
| 24-Valent + Protein | 265.1 ± 15.5 | -22.0 ± 1.2 |

Figure 31

Supplementary Table 9: Blood cell characterization across protein and LEPS formulations in CD-1 mice

| Animal<br>Blood Cell | Sham | Alum:PsaO | | | LEPS(20V) | | LEPS(20V):CRM197 | |
|---|---|---|---|---|---|---|---|---|
| | | 1x | 5x | 10x | 1x | 5x | 10x |
| Male CD-1 Mice (N=5) | | | | | | | | |
| Basophils (%) | 0.1 ± 0.1 | 0.1 ± 0.1 | 0.1 ± 0.1 | 0.1 ± 0.1 | 0.1 ± 0.1 | 0.1 ± 0.1 | 0.1 ± 0.1 |
| Eosinophils (%) | 3.1 ± 2.2 | 3.2 ± 2.0 | 2.8 ± 2.1 | 2.9 ± 2.2 | 2.9 ± 2.5 | 3.1 ± 2.5 | 3.0 ± 2.5 |
| Lymphocytes (%) | 79.1 ± 5.8 | 80.8 ± 2.7 | 81.4 ± 2.4 | 82.4 ± 3.8 | 80.4 ± 1.4 | 80.7 ± 3.4 | 80.3 ± 4.0 |
| Monocytes (%) | 8.7 ± 3.4 | 8.0 ± 5.3 | 8.3 ± 5.6 | 7.4 ± 2.5 | 8.5 ± 4.4 | 8.3 ± 4.1 | 7.8 ± 6.2 |
| Neutrophils (%) | 8.0 ± 2.9 | 8.0 ± 1.3 | 7.3 ± 2.5 | 7.2 ± 2.3 | 8.4 ± 1.0 | 7.8 ± 1.4 | 7.3 ± 1.5 |
| Erythrocytes (10^12*L^-1) | 7.5 ± 0.3 | 7.2 ± 0.3 | 7.1 ± 0.2 | 7.9 ± 0.3 | 7.9 ± 0.3 | 7.7 ± 0.2 | 7.4 ± 0.2 |
| Leukocytes (10^9*L^-1) | 6.1 ± 1.3 | 6.7 ± 1.1 | 6.8 ± 1.0 | 6.5 ± 1.2 | 6.1 ± 1.0 | 6.2 ± 1.3 | 6.9 ± 1.0 |
| Thrombocytes (10^9*L^-1) | 1100.0 ± 190.0 | 1122.0 ± 160.5 | 1089.0 ± 126.0 | 1056.0 ± 153.0 | 1155.0 ± 124.5 | 1078.0 ± 158.0 | 1100.0 ± 147.0 |
| Female CD-1 Mice (N=5) | | | | | | | | |
| Basophils (%) | 0.0 ± 0.0 | 0.0 ± 0.0 | 0.0 ± 0.0 | 0.0 ± 0.0 | 0.0 ± 0.0 | 0.0 ± 0.0 | 0.0 ± 0.0 |
| Eosinophils (%) | 5.1 ± 2.5 | 5.3 ± 2.8 | 5.3 ± 2.5 | 5.4 ± 2.7 | 5.3 ± 1.9 | 5.2 ± 2.3 | 5.5 ± 2.8 |
| Lymphocytes (%) | 79.4 ± 3.1 | 78.2 ± 4.7 | 80.7 ± 5.0 | 78.9 ± 5.4 | 80.7 ± 3.9 | 76.2 ± 4.1 | 79.9 ± 6.2 |
| Monocytes (%) | 6.3 ± 2.7 | 6.6 ± 3.2 | 6.0 ± 2.1 | 6.7 ± 3.1 | 6.6 ± 2.8 | 6.4 ± 3.2 | 6.4 ± 3.1 |
| Neutrophils (%) | 10.1 ± 4.3 | 10.0 ± 4.2 | 8.1 ± 4.0 | 9.2 ± 3.5 | 7.9 ± 4.1 | 12.0 ± 5.2 | 9.1 ± 4.2 |
| Erythrocytes (10^12*L^-1) | 8.1 ± 0.2 | 8.1 ± 0.2 | 8.1 ± 0.2 | 7.9 ± 0.2 | 7.7 ± 0.3 | 8.5 ± 0.2 | 8.3 ± 0.3 |
| Leukocytes (10^9*L^-1) | 4.2 ± 0.9 | 4.5 ± 0.7 | 4.5 ± 1.0 | 4.7 ± 1.0 | 4.5 ± 0.9 | 4.4 ± 0.7 | 4.2 ± 0.9 |
| Thrombocytes (10^9*L^-1) | 936.0 ± 225.0 | 964.1 ± 269.5 | 982.8 ± 278.8 | 907.9 ± 229.5 | 973.4 ± 200.2 | 893.6 ± 177.8 | 945.4 ± 240.8 |

Figure 32

Supplementary Table 10: Hematological assessment across protein and LEPS formulations in CD-1 mice

| Animal | Sham | Alum:PsaO | | | LEPS(20V):CRM197 | | |
|---|---|---|---|---|---|---|---|
| Molecule | | 1x | 5x | 10x | 1x | 5x | 10x |
| Male CD-1 Mice (N=5) | | | | | | | |
| ALAT (U/L) | 38.0 ± 5.0 | 36.7 ± 4.9 | 35.6 ± 4.2 | 34.9 ± 6.3 | 36.7 ± 4.3 | 36.7 ± 6.1 | 34.9 ± 4.7 |
| AP (U/L) | 140.0 ± 30.0 | 141.4 ± 36.3 | 134.4 ± 27.9 | 133.8 ± 30.6 | 145.6 ± 27.0 | 147.0 ± 24.0 | 133.0 ± 30.9 |
| ASAT (μmol/L) | 70.0 ± 14.0 | 71.4 ± 12.0 | 69.3 ± 10.9 | 70.7 ± 10.7 | 70.0 ± 16.8 | 70.0 ± 17.2 | 68.6 ± 10.9 |
| Bilirubine (μmol/L) | <15 | <15 | <15 | <15 | <15 | <15 | <15 |
| Calcium (mmol/L) | 2.5 ± 0.0 | 2.6 ± 0.1 | 2.5 ± 0.1 | 2.5 ± 0.0 | 2.5 ± 0.1 | 2.5 ± 0.1 | 2.4 ± 0.1 |
| Cholesterol (mmol/L) | 3.7 ± 0.8 | 3.8 ± 0.7 | 3.8 ± 0.9 | 2.7 ± 0.9 | 3.9 ± 0.9 | 3.8 ± 1.0 | 3.8 ± 0.7 |
| Creatinine (μmol/L) | 27.0 ± 2.1 | 28.4 ± 2.1 | 26.5 ± 2.2 | 25.7 ± 2.2 | 27.0 ± 2.3 | 25.9 ± 2.5 | 25.7 ± 1.6 |
| Glucose (mmol/L) | 10.8 ± 1.1 | 11.3 ± 1.2 | 10.3 ± 1.3 | 10.3 ± 1.2 | 11.3 ± 1.0 | 10.5 ± 1.0 | 11.1 ± 1.1 |
| Hematocrite (L/L) | 0.4 ± 0.0 | 0.4 ± 0.0 | 0.4 ± 0.0 | 0.5 ± 0.0 | 0.5 ± 0.0 | 0.5 ± 0.0 | 0.4 ± 0.0 |
| Hemoglobin (mmol/L) | 8.0 ± 0.5 | 7.7 ± 0.6 | 7.9 ± 0.5 | 8.2 ± 0.5 | 7.6 ± 0.5 | 8.3 ± 0.6 | 7.9 ± 0.5 |
| LD (U/L) | 453.0 ± 144.0 | 464.1 ± 122.4 | 464.1 ± 133.9 | 450.5 ± 159.8 | 459.6 ± 175.7 | 468.7 ± 169.9 | 459.6 ± 147.2 |
| Potassium (mmol/L) | 4.1 ± 0.2 | 4.3 ± 0.1 | 4.3 ± 0.2 | 4.0 ± 0.1 | 3.9 ± 0.2 | 4.2 ± 0.2 | 4.2 ± 0.2 |
| Phosphate (mmol/L) | 2.2 ± 0.3 | 2.1 ± 0.3 | 2.1 ± 0.3 | 2.2 ± 0.2 | 2.1 ± 0.3 | 2.1 ± 0.3 | 2.2 ± 0.4 |
| Sodium (mmol/L) | 150.0 ± 2.0 | 157.5 ± 2.3 | 151.5 ± 1.5 | 147.0 ± 1.9 | 148.0 ± 2.0 | 151.0 ± 2.0 | 147.0 ± 1.5 |
| Triglyceride (mmol/L) | 1.5 ± 0.4 | 1.4 ± 0.5 | 1.4 ± 0.5 | 1.4 ± 0.5 | 1.5 ± 0.4 | 1.5 ± 0.4 | 1.4 ± 0.5 |
| Urea (mmol/L) | 7.8 ± 0.8 | 8.1 ± 1.0 | 7.6 ± 0.7 | 8.1 ± 0.8 | 7.6 ± 1.0 | 7.9 ± 0.6 | 8.1 ± 0.6 |
| Female CD-1 Mice (N=5) | | | | | | | |
| ALAT (U/L) | 34.0 ± 8.0 | 34.0 ± 6.6 | 34.7 ± 8.2 | 34.7 ± 7.5 | 34.0 ± 7.9 | 33.0 ± 9.6 | 35.7 ± 8.7 |
| AP (U/L) | 140.0 ± 31.0 | 148.3 ± 38.4 | 146.9 ± 28.8 | 139.7 ± 31.3 | 139.7 ± 30.4 | 146.9 ± 35.0 | 146.9 ± 28.8 |
| ASAT (μmol/L) | 78.0 ± 14.0 | 78.0 ± 12.6 | 78.0 ± 10.9 | 74.1 ± 16.4 | 78.8 ± 16.2 | 76.4 ± 15.7 | 79.6 ± 15.8 |
| Bilirubine (μmol/L) | <15 | <15 | <15 | <15 | <15 | <15 | <15 |
| Calcium (mmol/L) | 2.5 ± 0.3 | 2.4 ± 0.0 | 2.4 ± 0.0 | 2.5 ± 0.0 | 2.4 ± 0.0 | 2.4 ± 0.0 | 2.4 ± 0.0 |
| Cholesterol (mmol/L) | 3.0 ± 0.5 | 3.0 ± 0.4 | 2.9 ± 0.6 | 3.0 ± 0.5 | 3.0 ± 0.6 | 3.0 ± 0.5 | 3.0 ± 0.5 |
| Creatinine (μmol/L) | 30.0 ± 2.0 | 28.8 ± 1.8 | 28.5 ± 1.8 | 31.2 ± 2.0 | 29.1 ± 2.2 | 31.5 ± 2.0 | 28.8 ± 2.4 |
| Glucose (mmol/L) | 8.4 ± 0.9 | 8.8 ± 1.0 | 8.6 ± 1.1 | 8.7 ± 1.0 | 8.7 ± 1.0 | 8.1 ± 1.0 | 8.8 ± 0.7 |
| Hematocrite (L/L) | 0.5 ± 0.0 | 0.5 ± 0.0 | 0.4 ± 0.0 | 0.5 ± 0.0 | 0.5 ± 0.0 | 0.4 ± 0.0 | 0.4 ± 0.0 |
| Hemoglobin (mmol/L) | 8.6 ± 0.2 | 8.8 ± 0.2 | 8.5 ± 0.2 | 8.6 ± 0.2 | 9.0 ± 0.2 | 8.7 ± 0.2 | 9.0 ± 0.2 |
| LD (U/L) | 678.0 ± 100 | 699.3 ± 124.0 | 691.6 ± 76.0 | 684.9 ± 114.0 | 705.1 ± 77.0 | 698.3 ± 81.0 | 664.4 ± 108.0 |
| Potassium (mmol/L) | 3.8 ± 0.2 | 3.6 ± 0.2 | 3.7 ± 0.2 | 3.8 ± 0.2 | 3.6 ± 0.2 | 3.8 ± 0.2 | 3.8 ± 0.2 |
| Phosphate (mmol/L) | 2.6 ± 0.2 | 2.7 ± 0.2 | 2.5 ± 0.2 | 2.6 ± 0.1 | 2.7 ± 0.2 | 2.5 ± 0.2 | 2.5 ± 0.2 |
| Sodium (mmol/L) | 153.0 ± 2.0 | 146.9 ± 2.4 | 146.9 ± 1.5 | 157.6 ± 1.7 | 148.4 ± 2.4 | 151.5 ± 2.0 | 160.7 ± 2.0 |
| Triglyceride (mmol/L) | 1.0 ± 0.3 | 1.0 ± 0.2 | 1.0 ± 0.2 | 1.0 ± 0.3 | 1.0 ± 0.3 | 1.0 ± 0.2 | 1.0 ± 0.3 |
| Urea (mmol/L) | 7.1 ± 1.3 | 7.3 ± 1.5 | 6.9 ± 1.6 | 7.3 ± 1.0 | 7.3 ± 1.0 | 7.5 ± 1.3 | 7.3 ± 1.4 |

ALAT: Alanine aminotransferase; AP: Alkaline phosphatase; ASAT: Aspartate aminotransferase; LD: Lactate dehydrogenase

Figure 33

Supplementary Table 11: Percent change in OPA 50% killing dilution of planktonic S. pneumoniae for LEPS(20V):PncO protein dose escalation

| Serotype | LEPS(20V):PncO OPA Titer Percent Change | |
|---|---|---|
| | 34 → 68 μg | 68 → 136 μg |
| 1 | 71% | -8% |
| 2 | 24% | 26% |
| 3 | 21% | -3% |
| 4 | 28% | -4% |
| 5 | 39% | -16% |
| 6A | 35% | -10% |
| 6B | 32% | -12% |
| 7F | 37% | -3% |
| 8 | 24% | 18% |
| 9N | 17% | 14% |
| 9V | 11% | 17% |
| 12F | 18% | 16% |
| 14 | 23% | -7% |
| 17F | 10% | -10% |
| 18C | 33% | -13% |
| 19A | 35% | -8% |
| 19F | 12% | -11% |
| 20 | 20% | 0% |
| 22F | 35% | -7% |
| 23F | 20% | 9% |

Figure 34

Supplementary Table 12: Percent change in antibody titer for LEPS(20V):PncO protein dose escalation

| Serotype | LEPS(20V):PncO Antibody Titer Percent Change | |
|---|---|---|
| | 34 → 68 µg | 68 → 136 µg |
| PncO | 34% | 49% |
| 1 | 106% | -12% |
| 2 | 38% | 35% |
| 3 | 70% | -69% |
| 4 | -42% | 5% |
| 5 | 119% | -57% |
| 6A | 97% | -42% |
| 6B | 76% | -43% |
| 7F | 66% | -40% |
| 8 | 19% | 17% |
| 9N | -1% | -7% |
| 9V | 24% | -37% |
| 12F | 0% | -20% |
| 14 | 47% | 0% |
| 17F | 33% | -52% |
| 18C | 87% | -21% |
| 19A | 85% | -25% |
| 19F | -20% | 9% |
| 20 | 1% | -21% |
| 22F | -6% | -15% |
| 23F | 80% | -14% |

Figure 35

COMPREHENSIVE VACCINE DESIGN FOR COMMENSAL DISEASE PROGRESSION

CROSS-REFERENCE TO RELATED APPLICATIONS

This application claims priority to U.S. Provisional patent application No. 62/572,081, filed on Oct. 13, 2017, and U.S. Provisional patent application No. 62/670,419, filed on May 11, 2018, the disclosures of which is incorporated herein by reference.

STATEMENT REGARDING FEDERALLY SPONSORED RESEARCH

This invention was made with government support under Grant AI088485 and AI117309 awarded by the National Institutes of Health. The government has certain rights in the invention.

BACKGROUND OF THE INVENTION

Commensal microorganisms generally serve a symbiotic relationship with the inhabited host. However, under certain circumstances, a transition to virulence can prompt disease from a normally benign commensal. This poses a question of whether a therapy should prevent initial colonization, thus, eliminating any potential for future disease but also removing any benefit (either direct or indirect) provided by commensal establishment or whether a therapy should retain colonization (and any associated benefit) while targeting the process of virulence transition. This dilemma is well-represented by ongoing vaccination efforts to address pneumococcal disease.

Pneumococcal disease is a major global infectious disease threat that affects millions worldwide, especially the young, elderly, and resource-limited. Disease outcomes include pneumonia, bacteremia, meningitis, and otitis media (middle ear infection). As introduced generally above, treating this disease is challenging due to the scope of infection and the steps of disease progression.

More specifically, human colonization with the *Streptococcus pneumoniae* bacteria responsible for pneumococcal disease is nearly universal (Bogaert et al., *Lancet Infect Dis* 4, 144-154 (2004). For example, colonization occurs in over 95% of children within the first few years of life (Gray, et al., *J Infect Dis* 142, 923-933 (1980); Huebner et al., *The Pediatric Infectious Disease Journal* 19, 1017-1020 (2000)). The composition of colonization is complicated by >90 different serotypes of *S. pneumoniae*, differentiated by the polysaccharide content coating the bacterial cell (Daniels et al., *J Pediatr Pharmacol Ther* 21, 27-35 (2016)). Current vaccines harvest, purify, and combine the surface capsular polysaccharides (CPSs) of *S. pneumoniae* serotypes associated with aggressive invasive infection (Feldman et al., *The Journal of Infection*, (2014)). The approach has been effective at minimizing initial colonization, enabling herd immunity, and reducing disease (Loo et al., *The Pediatric Infectious Disease Journal* 33 Suppl 2, S140-151 (2014)).

However, the progression of pneumococcal disease requires more than colonization. Upon acquisition, *S. pneumoniae* establishes residence in the nasopharynx as an asymptomatic biofilm (Bakaletz, *Paediatr Respir Rev* 13, 154-159 (2012); Munoz-Elias et al., *Infection and Immunity* 76, 5049-5061 (2008)). In other words, *S. pneumoniae* represents an upper respiratory tract commensal. Disease occurs upon biofilm dissemination, often prompted by disruptive events (such as viral infection) that spur a sub-set of bacteria to become virulent (FIG. 5) (Marks et al., *mBio* 4, (2013)). Upon transition, these bacteria break free of the biofilm; spread to the lungs, blood, middle ear, and other locations; and cause the aforementioned disease types (Marks et al., *Infect Immun* 80, 2744-2760 (2012)). When viewed from this perspective, preventing colonization through current vaccine options serves as an upstream route to eliminating subsequent disease progression.

Yet limiting colonization is only possible for the 13-23 serotypes covered by current vaccines, which fall well short of the >90 serotypes thus far identified (Tin Htar et al., *BMC Infect Dis* 15, 419 (2015)). Hence, eliminating colonization prevents disease but also presents an unintended consequence of offering a niche in the nasopharynx for remaining serotypes to establish residence and progress to virulence (Richter et al., *Emerg Infect Dis* 19, 1074-1083 (2013); Weinberger et al., *Lancet* 378, 1962-1973 (2011)). According to the current strategy, the only hypothetical vaccine capable of providing universal coverage would incorporate polysaccharide surface antigens from every known serotype of *S. pneumoniae*. Such an objective is prohibitively expensive from a manufacturing perspective and still does not eliminate the danger of niche replacement with as yet undetected *S. pneumoniae* serotypes or altogether different upper respiratory tract commensals and pathogens (Weinberger et al., *Lancet* 378, 1962-1973 (2011); Hausdorff et al., *Expert Review of Vaccines* 14, 413-428 (2015); Madhi et al., *Journal of Infectious Diseases* 196, 1662-1666 (2007); Keller et al., Emergence and Pathogenesis. *mBio* 7, e01792 (2016); Spijkerman et al., *PloS One* 7, e39730 (2012)). As such, vaccine strategies are not yet available that can address the issue of new serotypes, or that provides a combined approach against both colonization as well as virulence transition.

SUMMARY OF THE DISCLOSURE

In the present disclosure compositions and methods are provided comprising antigens directed against colonization, and antigens directed against virulence transition. For example, non-covalent co-localization of two classes of complementary antigens, one to prevent colonization of the most aggressive *S. pneumoniae* serotypes and another to restrict virulence transition, provides complete vaccine effectiveness in animal subjects and the most comprehensive coverage of disease reported to date. As a result, the present vaccine formulation offers universal pneumococcal disease prevention with the prospect of effectively managing a disease that afflicts 10s-100s of millions globally. The approach more generally puts forth a balanced prophylactic treatment strategy in response to complex commensal-host dynamics.

In this disclosure, a dual-functioning liposomal formulation allowed co-localization of complementary antigen types, each associated with a separate state in commensal disease progression. From a manufacturing perspective, the liposomal design allows a cost-effective and scalable formulation in stark contrast to the production of current vaccine options. From a potency perspective, the liposomal formulation capacity and the broad and counter-acting nature of the enclosed antigens enable the most robust and comprehensive immune response reported to date as measured against Prevnar and Pneumovax controls, the current standards in commercial vaccine options for pneumococcal disease.

The compositions and methods of the present disclosure relate to liposomal encapsulation of bacterial polysaccharides (termed herein as LEPS). In an aspect, this disclosure provides a vaccine composition comprising liposomes. The liposomes in the composition may encapsulate a single type of bacterial polysaccharide or multiple types of bacterial polysaccharides, such as capsular polysaccharides. At least some of the liposomes have protein non-covalently attached to the surface such that at least a portion of the protein is exposed to the exterior of liposome. For example, the liposomes may encapsulate one or more capsular polysaccharides from Streptococcus pneumoniae serotypes and have one or more proteins attached to the surface via non-covalent attachment such that at least some portion of the protein is displayed on the surface to the exterior of the liposomes.

A vaccine composition may have multiple types of liposome, which each type encapsulating a different type of single or combination of serotypes (i.e., capsular polysaccharides). For example, a plurality of liposomes may encapsulate a first serotype, a plurality of liposomes may encapsulate a second serotype, a plurality of liposomes may encapsulate a third serotype and so on such that a composition may collectively have liposomes encapsulating from 1 to about 100 known serotypes. As additional serotypes are identified, the composition can be modified to add to it liposomes encapsulating the newly identified serotype. Similarly, still further, a plurality of liposomes may encapsulate a first combination of serotypes, a plurality of liposomes may encapsulate a second combination of serotypes and so on. All of some of the liposomes may have protein non-covalently attached such that at least a portion of the protein is displayed on the surface to exterior of the liposome. In an embodiment, a 20 valent (20 serotypes) vaccine composition is provided where the liposomes have single or multiple serotypes encapsulated in the liposomes, and the liposomes further have CRM197, PncO or GlpO, or combinations thereof attached non-covalently. In an embodiment, the 20 serotypes are 1, 2, 3, 4, 5, 6A, 6B, 7F, 8, 9N, 9V, 12F, 14, 17F, 18C, 19A, 19F, 20, 22F, and 23F. In an embodiment, the vaccine is a 24 valent (24 serotypes) vaccine composition, where the liposomes have single or multiple serotypes encapsulated in the liposomes, and wherein the 24 serotypes are 1, 2, 3, 4, 5, 6A, 6B, 7F, 8, 9N, 9V, 10A, 11A, 12F, 14, 15B, 17F, 18C, 19A, 19F, 20, 22F, 23F, and 33F.

In an example, the vaccine composition comprises liposomes, where the liposomes have a single serotype, and wherein the serotype content of all the liposomes in the composition may be same or different. Thus, for example, the composition may have a plurality of sets of liposomes, wherein each set of liposomes comprises a plurality of liposomes, each encapsulating a single serotype. The serotypes may be selected from the serotypes listed in FIG. 16. Additional sets of liposomes comprising other single serotypes may be prepared and added to this composition.

the composition may have one or more of the following: a plurality of liposomes encapsulating serotype 1, a plurality of liposomes encapsulating serotype 2, a plurality of liposomes encapsulating serotype 3, a plurality of liposomes encapsulating serotype 4, a plurality of liposomes encapsulating serotype 5, a plurality of liposomes encapsulating serotype 6A, a plurality of liposomes encapsulating serotype 6B, a plurality of liposomes encapsulating serotype 7F, a plurality of liposomes encapsulating serotype 8, a plurality of liposomes encapsulating serotype 9N, a plurality of liposomes encapsulating serotype 9V, a plurality of liposomes encapsulating serotype 10A, a plurality of liposomes encapsulating serotype 11A, a plurality of liposomes encapsulating serotype 12F, a plurality of liposomes encapsulating serotype 14, a plurality of liposomes encapsulating serotype 15B, a plurality of liposomes encapsulating serotype 17F, a plurality of liposomes encapsulating serotype 18C, a plurality of liposomes encapsulating serotype 19A, a plurality of liposomes encapsulating serotype 19F, a plurality of liposomes encapsulating serotype 20, a plurality of liposomes encapsulating serotype 22F, a plurality of liposomes encapsulating serotype 23F, a plurality of liposomes encapsulating serotype 33F.

Examples of proteins that can be non-covalently attached to the liposomes include the diphtheria toxoid mutant CRM197 or surface exposed proteins or portions of the proteins from bacteria, such as PncO and GlpO. Other examples of immunogenic carriers useful for the production of polysaccharide immunogens include the Diphtheria toxoid (DT), Tetanus toxoid (TT), Keyhole Limpet Haemocyanin (KLH), and the purified protein derivative of Tuberculin (PPD).

In an aspect, this disclosure provides a method for immunizing an individual against bacterial infection, such as S. pneumoniae infection comprising administering to the individual who is to be protected, a composition comprising liposomes, which have one or more serotypes encapsulated therein, and have one or more proteins non-covalently attached to the surface and exposed to the exterior.

BRIEF DESCRIPTION OF THE FIGURES

FIG. 15 (Table S1). OPA comparison between Prevnar 13 (PCV13), Pneumovax 23 (PPSV23), and a LEPS formulation containing 20 polysaccharides (i.e., 20 valent [20V]). Values represent serum dilution at which 50% of cellular killing occurred in the OPA assay. Dashed lines indicate nonvaccine serotypes; higher OPA readings are attributed to a stronger antibody response (i.e., higher titers) for the particular polysaccharide.

FIG. 16 (Table S2). OPA comparison between Prevnar 13 (PCV13), Pneumovax 23 (PPSV23), and the PncO+GlpO protein antigens (administered with Alum adjuvant). Values represent serum dilution at which 50% of cellular killing occurred in the OPA assay. Dashed lines indicate non-vaccine serotypes; higher OPA readings are attributed to a stronger antibody response (i.e., higher titers) for that particular polysaccharide. Serotype-specific *S. pneumoniae* strains utilized in the OPA assay include cellular phenotypes associated with initial colonization (planktonic) and disease (i.e., biofilm-released [BFR]).

FIG. 25: GlpO dose escalation antibody titers. Concentration of protein (black) and CPS (blue) antibodies in mice vaccinated with 34 (a), 68 (b), or 136 (c) μg of protein in LEPS(20V):GlpP formulation.

FIG. 26: GlpO+PncO dose escalation antibody titers. Concentration of protein (black) and CPS (blue) antibodies in mice vaccinated with 34 (a), 68 (b), 136 (c), or 272 (d) μg of total protein in LEPS(20V):GlpO+PncO formulation.

FIG. 27 (Table S4): Bacteria with GlpO homologs with percent homology of various protein regions including those that were tested for cross-reactivity.

FIG. 28 (Table S5): Concentration for metabolites in blood for CD-1 mice.

FIG. 29 (Table S6): Hematological assessment of leukocytes in CD-1 mice.

FIG. 30 (Table S7): Percent change in 50% killing dilution for LEPS(20V):PncO dose escalation FIG. 31 (Table S8): Percent change in antibody titer for LEPS(20V):PncO dose escalation.

FIG. 32 (Table S9): Complete OPA data for LEPS(20V): PncO dose escalation

FIG. 33 (Table S10): Complete OPA data for LEPS(20V): GlpO+PncO dose escalation

FIG. 34 (Table S11): LEPS(24V):PncO CPS OPA titer

FIG. 35 (Table S12): CPS OPA data for Round 1 study for NVT serotypes.

DETAILED DESCRIPTION OF THE DISCLOSURE

Figure 1:
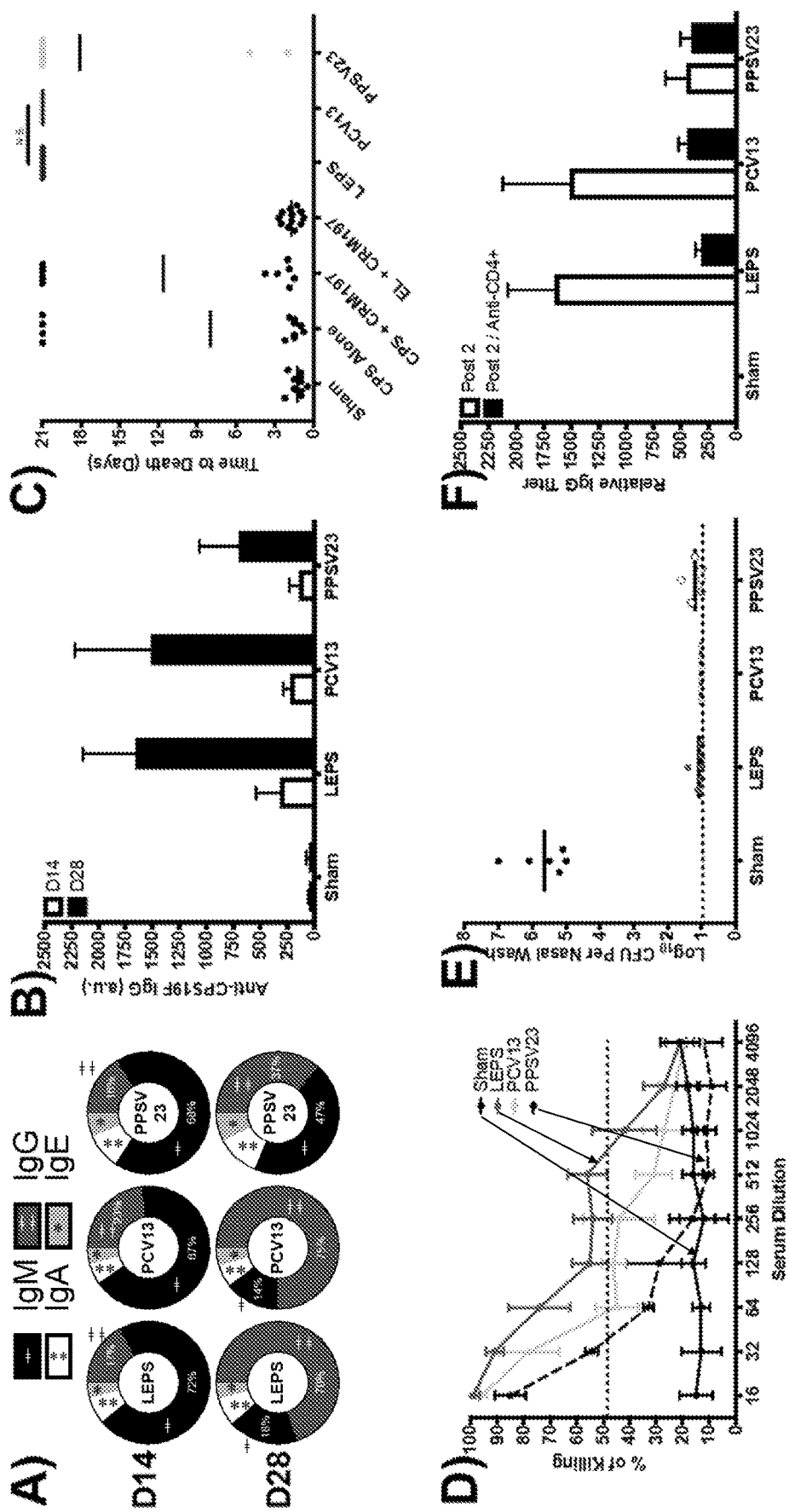
FIG. 1. LEPS vaccine effectiveness compared to commercial standards. Mice were vaccinated at 0 and 14 days with 1) LEPS containing capsular polysaccharide (CPS) from S. pneumoniae serotype 19F, 2) Prevnar 13 (PCV13), 3) Pneumovax 23 (PPSV23), 4) PBS (Sham), and 5) various controls (CPS Alone, CPS+CRM197, and empty LEPS [EL]+CRM197). Serum was collected at 14 and 28 days. (A) Antibody class shifting of LEPS, PCV13, and PPSV23 and (B) total IgG titers. (C) Protection against lethal challenge of serotype 19F in a murine sepsis model. (D) Functional antibody activity assessment of select vaccination strategies using an opsonophagocytic activity (OPA) assay. (E) Nasopharynx bacterial burden assessed in unimmunized or immunized mice measured at 5 days post-colonization. (F) 19F CPS antibody titers measured at 28 days (Post 2) in mice serum without (white) or with (black) CD4+ T cell depletion. N.S.: not significant.

The term "immune response" as used herein refers to the concerted action of the cells of the immune system including one or more of lymphocytes, antigen presenting cells, phagocytic cells, granulocytes, and others that results in selective damage to, destruction of, or elimination from the animal body of invading pathogens, cells or tissues infected with pathogens.

The term "immunogen" as used herein refers to a substance that is able to stimulate or induce a humoral antibody and/or cell-mediated immune response in a mammal. This term may be used interchangeably with "antigen" herein.

The term "isolated" as used herein with respect to polypeptides means polypeptides that are substantially separated from other macromolecules normally associated with the polypeptide in its natural state. An isolated polypeptide can be completely free of other macromolecules normally associated with the polypeptide in its natural state. For example, polypeptides may be at least 50, 60, 70, 80, 90, 95, or 99% pure. An isolated polypeptide, for example, can be purified from a cell that normally expresses the polypeptide, may be synthesized, or can be produced using recombinant DNA methodology.

The polysaccharides are typically from specific serotypes. Many serotypes, including those in Tables S1 and S2 (FIGS. 15 and 16 respectively) are characterized and known in the art. The polysaccharides are capsular polysaccharides from the particular bacteria. The polysaccharides used to prepare the formulations can be isolated capsular polysaccharides.

The terms "polypeptide", "peptide" and "protein" may be used interchangeably to mean a polymer comprising two or more amino acids joined to each other by peptide bonds or modified peptide bonds. Short chains are generally referred to as peptides (about 30 amino acids or less), medium chains as polypeptides (from 30 to 1,000 amino acids), and longer chains as proteins. Polypeptides may contain amino acids other than the 20 gene-encoded amino acids. Polypeptides include amino acid sequences modified either by natural processes, such as post-translational processing, or by chemical modification techniques that are well known in the art.

In contrast to covalent polysaccharide-protein coupling, the present disclosure utilizes liposomal technology to encapsulate the desired bacterial serotype (polysaccharide) content and then the desired protein is non-covalently attached and surface displayed. Thus, this disclosure provides liposomal encapsulation of one or more types of bacterial polysaccharides (LEPS) with the liposomes further comprising non-covalently attached and surface displayed one or more types of proteins, such as bacterial proteins, such as those exposed on the bacterial surface. An example of bacterial polysaccharide is a pneumococcal polysaccharide, such as a polysaccharide from *S. pneumoniae*. In contrast to the Prevnar formulations, the present LEPS formulations achieves glycoconjugate vaccine effectiveness through non-covalent co-localization of polysaccharide and the protein (e.g., CRM197). In contrast to the Prevnar and Pneumovax formulations, the present LEPS formulations comprise both polysaccharides and protein and provide a strategy against colonization as well as virulence transition. In the LEPS formulations, the target antigen (e.g., the surface-displayed *S. pneumoniae* proteins) are separate and in addition to the polysaccharide targets included in Prevnar formulations. In addition, the protein antigens represent a different aspect of commensal disease transition and thus add a new dimension to the potency and breadth of the resulting immune response. The protein antigens in the present formulations are selected because they are surface-located on the bacteria (such as *S. pneumoniae*) such that they are accessible to the immune response.

In one aspect, this disclosure provides a composition comprising liposomes encapsulating one or more types of bacterial polysaccharides and further comprising one or more types of bacterial proteins non-covalently attached and displayed on the surface of the liposome.

By the term "type" in reference to protein or polysaccharide means any particular protein or polysaccharide molecules. Thus, when only one "type" of protein or polysaccharide is present, that means one or more molecules of the particular protein or polysaccharide can be present. When more than one type of protein or polysaccharide are said to be present, that means a plurality of proteins or polysaccharides are present.

The liposomes of the present disclosure may encapsulate only one type of polysaccharide (serotype) or more than one type of polysaccharide. For example, the liposomes may have encapsulated therein only type of bacterial capsular polysaccharide or a plurality of types of bacterial capsular polysaccharides, such as capsular polysaccharides from *S. pneumoniae*.

The serotypes and details are available from various well know sources. For example, information regarding various serotypes for *S. pneumonia* is available including from Global Pneumococcal Strain Bank at the CDC, and the World Health Organization (WHO). (who.int/biologicals/publications/meetings/areas/vaccines/pneumococcal/Pneumo%20Meeting%20Report%20FINAL%20IK%2024_Dec_08.pdf?ua=1). Examples of pneumococcal capsular polysaccharides include serotypes provided in Tables S1 (FIG. 15) and S2 (FIG. 16) of this disclosure. In an embodiment, the serotypes include: one or more of the following: 4, 6B, 9V, 14, 18C, 19F, 23F, 1, 3, 5, 6A, 7F, 19A. In one embodiment, the seropyes are 4, 6B, 9V, 14, 18C, 19F, 23F. In an embodiment the serotypes are 4, 6B, 9V, 14, 18C, 19F, 23F, 1, 3, 5, 6A, 7F, and 19A. In an embodiment, the serotypes are 4, 6B, 9V, 14, 18C, 19F, 23F, 1, 5, 7F. In an embodiment, the serotypes are 1, 2, 3, 4, 5, 6B, 7F, 8, 9N, 9V, 10A, 11A, 12F, 14, 15B, 17F, 18C, 19A, 19F, 20, 22F, 23F, and 33F. In an embodiment, the serotypes are 1, 2, 3, 4, 5, 6A, 6B, 7F, 8, 9N, 9V, 10A, 11A, 12F, 14, 15B, 17F, 18C, 19A, 19F, 20, 22F, 23F, and 33F. In an embodiment, the serotypes are 1, 2, 3, 4, 5, 6A, 6B, 7F, 8, 9N, 9V, 12F, 14, 17F, 18C, 19A, 19F, 20, 22F, 23F.

The polysaccharides may be surface polysaccharides, such as the Vi polysaccharide antigen against *Salmonella typhi*, meningococcal polysaccharides (including type A, C, W135 and Y, and the polysaccharide and modified polysaccharides of group B meningococcus), polysaccharides from *Staphylococcus aureus*, polysaccharides from *Streptococcus agalactae*, polysaccharides from *Streptococcus pneumoniae*, polysaccharides from *Mycobacterium* e.g. *Mycobacterium tuberculosis* (such as mannophosphoinisitides trehaloses, mycolic acid, mannose capped arabinomannans, the capsule therefrom and arabinogalactans), polysaccharide from *Cryptococcus neoformans*, the lipopolysaccharides of non-typeable *Haemophilus influenzae*, the capsular polysaccharide from *Haemophilus influenzae* b, the lipopolysaccharides of *Moraxella catharralis*, the lipopolysaccharides of *Shigella sonnei*, the lipopeptidophosphoglycan (LPPG) of *Trypanosoma cruzi*, the cancer associated gangliosides GD3, GD2, the tumor associated mucins, especially the T-F antigen, and the sialyl T-F antigen, and the HIV associated polysaccharide that is structurally related to the T-F antigen, *Neisseria meningitidis* polysaccharides—in particular from serotypes A, B, C W-135 and Y, a capsular polysaccharide of *Haemophilus influenzae* b (PRP) and the like.

In one aspect, the present disclosure provides compositions comprising liposomes encapsulating one or more types of bacterial polysaccharides, such as bacterial capsular polysaccharides. In an embodiment, this disclosure provides compositions comprising liposomes encapsulating or more types of bacterial capsular polysaccharides from *S. pneumoniae*. A composition of the present disclosure may comprise a plurality of liposomes, with each of at least some of the liposome encapsulating a single type of bacterial (such as *Streptococcus pneumoniae*) capsular polysaccharide. Other liposomes may encapsulate a plurality of types of bacterial capsular polysaccharides. Some liposomes may encapsulate no polysaccharides. In an embodiment, the composition comprises: i) liposomes comprising a single type of polysaccharide, which polysaccharide may be same or different in different liposomes, and/or ii) liposomes comprising a plurality of types of polysaccharides, which plurality types may be different in different liposomes. In addition, optionally, some liposomes may encapsulate no polysaccharides (referred to herein as empty). In an embodiment the composition comprises liposomes, said liposomes comprising more than one type of polysaccharides. In one embodiment, a composition comprises liposomes, wherein some liposomes encapsulate a single type of *S. pneumoniae* capsular polysaccharide, which single type of *S. pneumoniae* capsular polysaccharide may be different in different liposomes, and/or some liposomes encapsulate more than one type of *S. pneumoniae* capsular polysaccharides, which more than one type of capsular polysaccharides may be different in different liposomes, and optionally, some liposomes may be empty.

At least some liposomes in the compositions have, non-covalently attached at the surface, protein molecules such that the proteins are displayed on the exterior surface. The surface displayed protein molecules need not be present in the aqueous compartment of the liposome where the polysaccharides reside. In an embodiment, the surface displayed protein molecules are not present in the aqueous compartment i.e., the liposomes do not encapsulate protein molecules. Rather the protein molecules are only non-covalently attached to the surface and displayed to the exterior of the liposomes. The protein molecules can be bacterial proteins such as surface exposed bacterial proteins. The surface exposed bacterial proteins and the polysaccharide can be from the same type of bacteria or different type of bacteria or may be non-bacterial proteins. In an example, they are from *Streptococcus pneumoniae*.

In an embodiment, the composition comprises:
a) liposomes encapsulating a single type of bacterial polysaccharides, and/or
b) liposomes encapsulating multiple types of bacterial polysaccharides;
and wherein one or more of the liposomes have non-covalently attached on their surface, protein molecules which are displayed to the exterior of the liposomes.

In an embodiment, the composition comprises:
a) liposomes encapsulating a single type of bacterial polysaccharides, and/or
b) liposomes encapsulating multiple types of bacterial polysaccharides;
and wherein one or more of the liposomes from a) and/or b) have non-covalently attached on their surface, protein molecules which are displayed to the exterior of the liposomes.

In an embodiment, the composition comprises:
a) liposomes encapsulating a single type of *S. pneumoniae* capsular polysaccharide, and/or
b) liposomes encapsulating multiple types of *S. pneumoniae* capsular polysaccharides;
and wherein at least some of the liposomes have non-covalently attached on their surface, protein molecules, such that at least a portion of the protein molecule is displayed to the exterior of the liposomes. In an embodiment, the protein molecule is surface exposed *S. pneumoniae* proteins.

In an embodiment, the composition comprises:
a) liposomes encapsulating a single type of *S. pneumoniae* capsular polysaccharide, wherein the capsular polysaccharide is selected from the serotype group consisting of serotypes from Tables S1 and S2 (FIGS. 15 and 16 respectively) and/or
b) liposomes encapsulating multiple types of *S. pneumoniae* capsular polysaccharides selected from the group consisting of serotypes from Tables S1 and S2 (FIGS. 15 and 16 respectively);
and wherein at least some of the liposomes have non-covalently attached on their surface, protein molecules, such that at least a portion of the protein molecule is displayed to the exterior of the liposomes. In an embodiment, the protein molecule is surface exposed *S. pneumoniae* proteins.

In an embodiment, the composition comprises: a plurality of liposomes sets, wherein each set of liposomes encapsulates a single type of *S. pneumoniae* capsular polysaccharide, which is distinct from the single types of capsular polysaccharides encapsulated in other sets of liposomes in the composition, and wherein some liposomes may not encapsulate any capsular polysaccharide, and wherein at least some of the liposomes have non-covalently attached on their surface, protein molecules, such that at least a portion of the protein molecule is displayed to the exterior of the liposomes. In an embodiment, the protein molecule is surface exposed *S. pneumoniae* proteins. The single types of *S. pneumoniae* capsular polysaccharide may be selected from Tables S1 and S2 (FIGS. 15 and 16 respectively)).

In an embodiment, the composition comprises:
a) liposomes encapsulating a single type of *S. pneumoniae* capsular polysaccharide, wherein the capsular polysaccharide is selected from the serotype group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F and/or
b) liposomes encapsulating multiple types of *S. pneumoniae* capsular polysaccharides selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F;
and wherein at least some of the liposomes have non-covalently attached on their surface, protein molecules, such that at least a portion of the protein molecule is displayed to the exterior of the liposomes. In an embodiment, the protein molecule is surface exposed *S. pneumoniae* proteins.

In an embodiment, the composition comprises:
a) liposomes encapsulating a single type of *S. pneumoniae* polysaccharide, wherein the polysaccharide is selected from the serotype group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F and/or
b) liposomes encapsulating multiple types of *S. pneumoniae* polysaccharides selected from the serotype group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F;
and wherein the liposomes have non-covalently attached on their surface, protein molecules comprising or selected from the group consisting of CRM197, Diphtheria toxoid (DT or the CRM197 mutant), Tetanus toxoid (TT), Keyhole Limpet Haemocyanin (KLH), purified protein derivative of Tuberculin (PPD), surface exposed proteins or portions of the proteins from bacteria, such as, PncO, GlpO, and combinations thereof such that at least a portion of the protein molecule is displayed to the exterior of the liposomes.

In one embodiment, the composition may comprise liposomes with each liposome encapsulating a single serotype polysaccharide. However, different liposomes within the composition may have the same or different single serotype polysaccharide. The protein molecules non-covalently attached to the surface of the liposomes may be the same or different on the different liposomes. The liposomes may have a single type of protein molecule displayed on the surface or multiple types of protein molecules displayed on the surface. Further, some liposomes in the composition may not encapsulate polysaccharides and some liposomes in the composition may not have any proteins attached and displayed on the surface. Some liposomes may only encapsulate polysaccharides and have no proteins attached to the surface, and some liposomes may have only proteins attached to the surface and no polysaccharides encapsulated.

When the liposomes encapsulate a plurality of bacterial polysaccharide types (serotypes), the number of the types can be from 2-100. For example, the number can be from 5 to 50, from 5 to 25, from 5 to 20 or any number from 2-100. In one embodiment, the liposomes can encapsulate more than 100 polysaccharide types. In specific embodiments, the serotypes may be 15, 16, 17, 18, 19, 20, 21, 22, 23, 24, 25, 26, 27, 28, 29, 30 or more (up to 100).

Liposome bilayers may comprise one or more types of phospholipids known in the art. The lipid structures encapsulating the polysaccharides and displaying protein molecules on the surface by non-covalent attachment may be monolayers. In an example, a composition may comprise a mix of bilayers, monolayers or other lipidic structures.

As used herein, "phospholipid" is a lipid having a hydrophilic head group having a phosphate group connected via a glycerol backbone to a hydrophobic lipid tail. The phospholipid comprises an acyl side chain of 6 to 22 carbons, including all integer number of carbons and ranges therebetween. The acyl chains may be saturated or unsaturated. Examples of phospholipids include phosphatidylserine, phosphatidylcholine, phosphatidylethanolamine, phosphatidylglycerol, phosphatidylinositol and the like. Examples include 1,2-dioleoyl-sn-glycero-3-phosphocholine (DOPC), 1,2-dimyristoyl-sn-glycero-3-phosphocholine (DMPC) and 1,2-distearoyl-sn-glycero-3-phosphocholine (DSPC).

In an embodiment, for example, the phospholipids can be any phospholipids, saturated or unsaturated. The acyl chains in the phospholipids may contain from 6 to 22 carbons. Liposomes may comprise cholesterol and/or other sterols, and the phospholipids may be PEGylated.

In an embodiment, the liposome bilayer may comprise porphyrin conjugates. In an example, the phospholipid in the porphyrin conjugate is 1-palmitoyl-2-hydroxy-sn-glycero-3-phosphocholine. The phospholipid of the porphyrin conjugate may comprise, or consist essentially of phosphatidylcholine, phosphatidylethanoloamine, phosphatidylserine and/or phosphatidylinositol. In an example, the porphyrin is conjugated to the glycerol group on the phospholipid by a carbon chain linker of 1 to 20 carbons, including all integer number of carbons therebetween.

In various embodiments, in addition to the porphyrin conjugates, the bilayer of the liposomes also comprises other phospholipids. The fatty acid chains of these phospholipids may contain a suitable number of carbon atoms to form a bilayer. For example, the fatty acid chain may contain 12, 14, 16, 18, 20 or 22 carbon atoms. In different embodiments the bilayer comprises phosphatidylcholine, phosphatidylethanoloamine, phosphatidylserine and/or phosphatidylinositol.

For example, the liposomes bilayer can comprise porphyrin phospholipid conjugate, phospholipid that is not conjugated to porphyrin, optionally cholesterol, and optionally PEG-phospholipid. The PEG may be of any convenient size. For example, the average molecular weight of the PEG moiety can be between 500 and 5000 Daltons and all integer values and ranges therebetween. Other PEG sizes may also be used. The PEG-lipid may be present in an amount of 0 to 20 mol % including all percentage amounts therebetween to the tenth decimal point. Examples of PEG lipid include DSPE-PEG such as DSPE-PEG-2000, DSPE-PEG-5000 or other sizes of DSPE-PEG.

The present bilayers and monolayers may also comprise sterols. The sterols may be animal sterols or plant sterols. Examples of sterols include cholesterol, sitosterol, stigmasterol, and cholesterol. In embodiments, cholesterol may be present from 0 mol % to 50 mol %, or 0.1 to 50 mol %. In other embodiments, cholesterol may be present from 1 to 50 mol %, 5 to 45 mol %, or 10 to 30 mol %.

Proteins or peptides are non-covalently attached to the liposome bilayers such that they are displayed on the surface. In an embodiment, histidine tagged (HIS-tag) proteins may be non-covalently attached to the liposomes such that the proteins are displayed on the surface. For example, the liposomes may comprise one or more group(s)/moiety(ies) within a bilayer (e.g., a porphyrin, macrocycle, amino acid, or metal-ion chelating lipid). Using metal as an example, (e.g., $Co^{2+}$, $Ni^{2+}$, $Zn^{2+}$, $Cu^{2+}$, and $Fe^{3+}$) the metal may be chelated to a moiety in the bilayer such that the metal resides in or within the bilayer and a protein can be non-covalently attached to the metal via an interaction (e.g., coordination) between a portion of the protein (e.g., a group or moiety that binds to the metal, such as, for example, a histidine tag) and the metal, such that at least at a portion of the protein is within the bilayer, and the remainder of the protein is presented on the exterior of the structure. For example, the bilayer structures may comprise porphyrins with cobalt chelated thereto such that the cobalt metal resides within the bilayer and the porphyrin macrocycle, and further has protein molecules with a histidine tag non-covalently attached thereto, such that at least a portion of the His-tag is within the bilayer and coordinated to the cobalt metal core. The remainder of the molecule containing the His-tag is displayed on the exterior of the liposome. In another example, metal chelation-ligand interactions, such as occurring between nitrilotriacetic acid (NTA)-nickel and multi-histidines, can provide noncovalent attachment of histidine-tagged proteins to liposomes. Thus, the Ni-NTA can be present in the bilayer and histidine tag can be non-covalently attached thereto, such that at least a portion of the His-tag of the protein is within the bilayer and coordinated to the Ni. The remainder of the protein molecule is displayed on the exterior of the liposome.

In an embodiment, instead of metal chelation chemistries, other affinity based approaches, such as streptavidin-biotin based chemistries can be used to non-covalently attach proteins to the liposomes. The liposomes can incorporate streptavidin in the bilayer and biotinylated proteins can then be non-covalently attached to the liposome bilayers. For example, streptavidin can be attached to the liposome covalently or non-covalently. In another example, the liposomes can incorporate biotinylated lipids (e.g. DSPE-PEG-Biotin). The biotinylated liposomes can be incubated with streptavidin-linked protein to form a biotin-streptavidin linkage (BS linkages). In one embodiment, biotin-containing liposomes can be attached to streptavidin and biotinylated protein to create a biotin-streptavidin-biotin linkage (BSB linkages).

An example of the protein that can be non-covalently conjugated to the liposomes is CRM197. Other examples of immunogenic carriers useful for the production of polysaccharide immunogens include the Diphtheria toxoid (DT or the CRM197 mutant), Tetanus toxoid (TT), Keyhole Limpet Haemocyanin (KLH), and the purified protein derivative of Tuberculin (PPD). Further, additionally or alternatively, surface exposed proteins or portions of the proteins from bacteria may also be used, such as, for example, PncO or GlpO. In one embodiment, both PncO and GlpO may be used. In one embodiment, only GlpO or only PncO may be used.

For example, PncO or a fragment thereof that elicits an immune response protective against a *streptococcus*, such as, for example, *Streptococcus pneumoniae* may be used. The PncO may be any one of those produced by a *Streptococcus* species, including those from *Streptococcus pneumoniae*, *Streptococcus gordonii*, *Streptococcus sanguinis*, Streptococcus thermophilus, Streptococcus suis, Streptococcus agalactiae, Streptococcus pyogenes, Streptococcus mutans, Enterococcus faecalis, Enterococcus faecium, Rhodococcus sp.

The PncO need not be identical to the amino acid sequence of the PncO from S. pneumoniae. Modifications can be made to the protein sequence without altering its immunogenicity, and protective capacity of antibodies raised thereto. For example, conservative substitutions may be made within the group of following amino acids 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). For example, the antigen may be from 90 to 99% identical to the sequence of PncO provided herein, wherein the protein may elicit protective antibodies against a streptococcus, such as, for example, Streptococcus pneumoniae.

The sequence of PncO is available as GenBank Accession No. ABJ54598.1 for pncO (blpY) from Streptococcus pneumoniae D39. The sequence is provided below. The surface accessible regions in the PncO sequence are shown as bolded.

(SEQ ID NO : 1)
MKKYQLLFKISAVFSYLFFVFGLSQLTLIVQNYWQFSSQIGNFVWIQNIL

SLLFSGVMIWILVKTGHGYLFRIPRKKWLWYSILTVLVVVLHISFNVQTA

KHVQSTAEGWNVLIGYSGTNFAELGIYVTLFFLTPLMEELIYRGLLQHAF

FKHSRFGLDLLLPSILFALPHFLSLPSLLDIFVFATFGIIFAGLTRYTKS

IYPSYAVHVINNIVATFPFLLTFLHRVLG

In an embodiment, the sequence of the surface-displayed proteins may be from 80 to 99% identical to the known sequences. Thus, the proteins non-covalently attached to the liposome surface may be at least 70%, at least 75%, at least 80%, at least 85%, at least 90% or at least 95% identical to known sequences, wherein the protein is able to generate protective antibodies against a streptococcus, such as, for example, Streptococcus pneumoniae. In an embodiment, the PncO has at least 70% identity, preferably 80 or 85%, such as at least 90% or at least 95, 98 or 99% identity to the PncO of SEQ ID NO:1.

The sequence of GlpO is available as GenBank Accession No. EC 1.1.3.21 from Streptococcus pneumoniae D39. The sequence is provided below.

(SEQ ID NO: 2)
MEFSKKTRELSIKKMQERTLDLLIIGGGITGAGVALQAAASGLETGLIEM

QDFAEGTSSRSTKLVHGGLRYLKQFDVEVVSDTVSERAVVQQIAPHIPKP

DPMLLPVYDEDGATFSLFRLKVAMDLYDLLAGVSNTPTANKVLSKDQVLE

RQPNLKKEGLVGGGVYLDFRNNDARLVIENIKRANQDGALIANHVKAEGF

LFDESGKITGVVARDLLTDQVFEIKARLVINTTGPWSDKVRNLSNKGTQF

SQMRPTKGVHLVVDSSKIKVSQPVYFDTGLGDGRMVFVLPRENKTYFGTT

DTDYTGDLEHPKVTQEDVDYLLGIVNNRFPESNITIDDIESSWAGLRPLI

AGNSASDYNGGNNGTISDESFDNLIATVESYLSKEKTREDVESAVSKLES

STSEKHLDPSAVSRGSSLDRDDNGLLTLAGGKITDYRKMAEGAMERVVDI

LKAEFDRSFKLINSKTYPVSGGELNPANVDSEIEAFAQLGVSRGLDSKEA

HYLANLYGSNAPKVFALAHSLEQAPGLSLADTLSLHYAMRNELALSPVDF

LLRRTNHMLFMRDSLDSIVEPVLDEMGRFYDWTEEEKATYRADVEAALAN

NDLAELKN

The surface accessible regions in the GlpO sequence are bolded above. The surface protein may be from 80 to 99% identical to the sequence of GlpO provided herein, wherein the antigen is able to generate protective antibodies against a streptococcus, such as, for example, Streptococcus pneumoniae. In one embodiment, the surface protein has at least 70% identity, preferably 80 or 85%, such as at least 90% identity or at least 95, 98 or 99% identity to the GlpO sequence provided herein.

The surface proteins can be a combination of the proteins described herein or other surface exposed proteins of bacteria or their immunogenic variants. For example, the proteins may be stkP or PspA.

The amount of protein and polysaccharides in the liposomes can be varied, for example, to elicit a desirable amount of response to afford protection. As an example, the amount of protein(s) incorporated in the liposomes per dose of the formulation can be from 1 µg/dose to 1 mg/dose (e.g., 30-650 µg/dose), including all 0.1 µg/dose values and ranges therebetween, and/or the amount of polysaccharide(s) in the liposomes can be from 10 µg/dose to 2.0 mg/dose (e.g., 80-1,100 µg/dose), including all 0.1 µg/dose values and ranges therebetween, and/or the amount of liposome lipid(s) is 500 µg/dose to 15 mg/dose (e.g., 900 µg/dose-10 mg/dose), including all 0.1 µg/dose values and ranges therebetween. There may or may not be other protein in the formulation, e.g., in the form of carriers or excipients.

In embodiments, the protein(s) incorporated in the liposomes per dose can be from 10 to 800 µg/dose, including all values and ranges therebetween to the tenth decimal place and ranges therebetween, and/or the polysaccharide(s) in the liposomes per dose can be from 10 µg/dose to 1.5 mg/dose or 50 µg/dose to 1 mg/dose, including all values and ranges therebetween to the tenth decimal place and ranges therebetween, and/or the liposome lipid(s) in the liposomes per dose can be from 750 µg/dose to 10 mg/dose, including all values and ranges therebetween to the tenth decimal place and ranges therebetween.

In an example, the amount of individual polysaccharide is 2-44 µg/dose, the amount of protein is 15-350 µg/dose, and the amount of liposome is 500-5000 µg/dose. For example, a LEPS20V formulation may have about 80 to 900 µg polysaccharide per dose (0.15-1.25 mg/kg normalized to surface area), about 30 to 650 µg of protein per dose (0.09-0.9 mg/kg), and 950-9500 µg of liposome per dose (about 1.4-13.5 mg/kg), which has a polysaccharide to protein ratio of about 0.14-27 µg/µg (1.36 in intended dose), a liposome to polysaccharide ratio of 1.1-110 µg/µg (e.g., 10.82), and a liposome to protein ratio of 1.5-300 µg/µg (e.g., 14.71). In another example, a LEPS24V formulation has 105-1050 µg polysaccharide per dose (0.15-1.25 mg/kg normalized to surface area), 32-650 µg of protein per dose (0.09-0.9 mg/kg), and 950-9500 µg of liposome per dose (1.36-13.55 mg/kg), which has a polysaccharide to protein ratio of 0.16-32 µg/µg (1.6 in intended dose), a liposome to polysaccharide ratio of 0.9-90 µg/µg (e.g., 9), and a liposome to protein ratio of 1.5-300 µg/µg (e.g., 15)

In various examples, the ratio of polysaccharide(s) to protein(s) in the liposomes can be from 0.1 to 50 w/w (based on the total weight of polysaccharide(s) and protein(s)), including all 0.1 values and ranges therebetween. In various examples, the ratio of polysaccharide(s) to protein(s) in the liposomes can be from 0.1 to 40 w/w (based on the total weight of polysaccharide(s) and protein(s)). In various examples, the polysaccharide loading of the liposomes expressed as liposome lipid to polysaccharide ratio can be from 0.5 to 200 w/w (based on the total weight of liposome lipid(s) and polysaccharide(s)). In an example, the protein loading of liposomes expressed as liposome lipid to protein ratio can be from 1 to 500 w/w (based on the total weight of liposome lipid(s) and protein(s)).

In an example, the liposomes (e.g., the liposomes in a composition (e.g., a dose)) comprise a polysaccharide to protein ratio of 0.6 to 0.7 (e.g., 0.68) and/or a liposome lipid to polysaccharide ratio of 10 to 11 (e.g., about 10.8) and/or a liposome lipid to protein ratio of 7-8 (e.g., about 7.35). In another example, a composition (e.g., a dose) comprises a polysaccharide to protein ratio of 0.75 to 0.85 (e.g., about 0.8) and/or a liposome lipid to polysaccharide ratio of about 8.5 to 9.5 (e.g., about 9.1) and/or a liposome lipid to protein ratio of 7-8 (e.g., about 7.35).

The option to scalably encapsulate additional polysaccharides within the LEPS formulation further highlights differences to current glycoconjugate vaccine options, which require successive effort and manufacturing cost with each covalent attachment of a new serotype CPS to CRM197 and this limits both broad vaccine coverage and global access. Scalably encapsulating additional polysaccharides within the LEPS formulations can be done in the form of addition of liposomes that encapsulate only the new one or more polysaccharides or preparing liposomes that encapsulate existing and new polysaccharides. Similarly, new surface displayed proteins may be added to the LEPS formulation by adding liposomes to the existing formulation, wherein the added liposomes have the surface-displaying new proteins or by preparing liposomes with the existing group of protein and the new proteins.

The formulation can include a carrier or excipient. The formulations can include an adjuvant to enhance the extent or nature of the immune reaction. Determination of the amount of the immunogenic antigen and/or the adjuvant can be in accordance with standard techniques in the pharmaceutical or veterinary arts.

In an embodiment, the present composition does not have an adjuvant. Although an adjuvant is not needed with the present composition, an adjuvant may be used if desired. For example, an adjuvant can be used as a 0.001 to 50 wt % solution in phosphate buffered saline, and the antigen is present in the order of micrograms to milligrams, such as about 0.0001 to about 5 wt %, such as about 0.0001 to about 1 wt %, such as about 0.0001 to about 0.05 wt %. The antigen can be present in an amount in the order of micrograms to milligrams, or, about 0.001 to about 20 wt %, such as about 0.01 to about 10 wt %, or about 0.05 to about 5 wt %. The adjuvant can be administered as a separate component in the immunogenic compositions or it can be incorporated into the liposomes.

Adjuvants that may be usefully employed in the preparation of vaccines include the following: oil adjuvants, for example, Freund's complete and incomplete adjuvants, mineral salts, alum, silica, kaolin, and carbon, polynucleotides and certain natural substances of microbial origin. An example of an adjuvant is a non-covalent complex of alpha-lactalbumin and fatty acid. Fatty acids useful for making the complex include unsaturated cis C14 to C20 fatty acids. (See WO 2014/008465).

For the present vaccine compositions, carrier and/or non-carrier adjuvants may be used. Examples include aluminum-based adjuvants (such as alum, aluminum hydroxide or aluminum phosphate), monophosphryl lipid A (MPL), and 3-O-deacylated monophosphoryl lipid A (or 3 De-O-acylated monophosphoryl lipid A or 3-O-desacyl-4' monophosphoryl lipid A) (3D-MPL).

The pharmaceutical preparations can comprise additives, such as diluent, adjuvant, excipient, or carrier. Such additives can be liquids, such as water and oils, saline, glucose or the like, and auxiliary, stabilizing, thickening, or lubricating agents, wetting or emulsifying agents, or pH buffering agents, gelling or viscosity enhancing additives, detergents and solubilizing agents (e.g., TWEEN® 20, TWEEN® 80 also referred to as polysorbate 20 or 80), anti-oxidants (e.g., ascorbic acid, sodium metabisulfite), preservatives (e.g., Thimersol, benzyl alcohol), bulking substances (e.g., lactose, mannitol), flavoring agents, colors, and the like, depending upon the route of administration and the preparation desired. See "Remington's Pharmaceutical Science", 17th edition, 1985. Non-aqueous solvents or vehicles can be used such as propylene glycol, polyethylene glycol, vegetable oils, such as olive oil and corn oil, gelatin, and injectable organic esters such as ethyl oleate. The formulations may be lyophilized and redissolved or resuspended just before use. The formulation may be sterilized by, for example, filtration through a bacteria retaining filter, by incorporating sterilizing agents into the compositions, by irradiating the compositions, or by heating the compositions.

A key feature of the present technology is that it does not require conjugation of the polysaccharide(s) to the protein(s). The conjugation step is not simple and in a conjugation type of vaccine formulation, the number of polysaccharides (serotypes) that can be included are limited by the size of the protein. In contrast, because the present technology does not require conjugation of the polysaccharide to the protein, it does not limit how many serotypes can be represented in a formulation. Thus, the present formulations are adaptable to inclusion of new serotypes that are identified. For example, liposomes encapsulating a new a serotype polysaccharide can be added to an existing formulation.

The present compositions can be provided as liquid preparations, suspensions, emulsions, tablets, pills, sustained-release formulations, emulsions, aerosols, sprays, or any other form suitable for introducing the compositions into a subject to generate an immune response protective against *S. pneumoniae* or other streptococci. The compositions may be administered to a human or a non-human animal.

The compositions can be administered to a population in general, or can be targeted to individuals who are at risk for developing *Streptococcus* infections such as *S. pneumoniae*. For example, it can be administered to any individual who is in close contact with an infected individual.

The compositions can be introduced into a subject using any suitable administration route, including but not limited to parenteral, subcutaneous, intraperitoneal, intramuscular, intravenous, mucosal (e.g., intranasal), topical, intradermal, and oral administration.

Immunization can be done by way of a single dose or it can be done by multiple doses (e.g., 1, 2, 3, 4, or 5 doses) that are spaced apart. For example, an initial administration and subsequent booster doses can be used. The compositions can be administered alone, or can be co-administered or sequentially administered with other prophylactic (such as, for example, other immunogenic compositions) or therapeutic compositions (such as, for example, antibiotics).

In an aspect, this disclosure provides a method of preparing a vaccine composition, such as a vaccine composition against S. pneumoniae, comprising preparing one or more sets of liposomes, wherein all the liposomes in a set encapsulate a single and same type of capsular polysaccharide (serotype), and mixing the sets to obtain a composition comprising liposomes encapsulating desired serotypes. Thus, liposomes encapsulating, for example one or more of the serotypes in FIGS. 15 and 16 may be used to form a vaccine composition. In an example, the serotypes are selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F. As additional serotypes are desired, liposomes encapsulating those additional serotypes may be prepared and added to the existing compositions or new compositions may be prepared that include the previous and the new serotypes.

In one aspect, this disclosure provides a method of preventing pneumonia in an individual comprising administering to the individual an effective amount of a composition described herein. This disclosure also provides a method of reducing the overall incidence of pneumonia in a population comprising administering to a plurality of individuals in the population an effective amount of compositions described herein, whereby administration of the immunogenic compositions prevents the occurrence of pneumonia in at least some of the individuals in the population such that overall incidence of pneumonia n the population is reduced.

Although specific references have been made to liposomal compositions directed toward generating an immune response against streptococci, the strategy, compositions and methods described herein are applicable for any bacteria. For example, the LEPS formulations can be used as vaccine compositions for *Staphylococcus aureus, Haemophilus influenzae, Moraxella catarrhalis, Escherichia coli, Clostridia difficile*. Other bacteria against which the present compositions can be formulated and used include *Streptococcus agalactae, Mycobacterium* e.g. *Mycobacterium tuberculosis, Cryptococcus neoformans*, non-typeable *Haemophilus influenzae, Haemophilus influenzae* b, *Shigella sonnei, Trypanosoma cruzi, Neisseria meningitides* and the like.

The following examples are provided as illustrative examples and are not intended to be restrictive in any way.

EXAMPLE 1

Best-In-Class Vaccination Comparison

Figure 6:
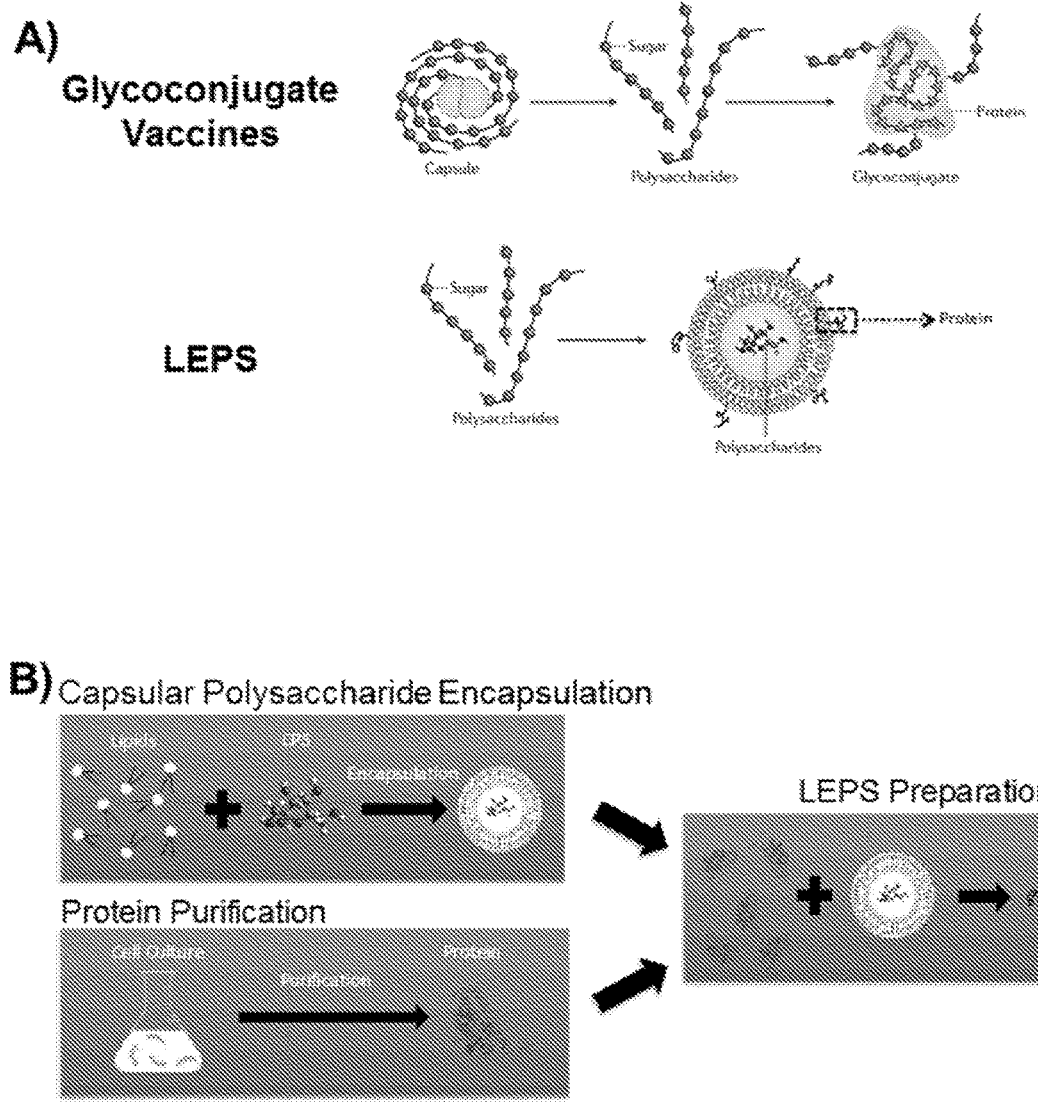
FIG. 6. The LEPS platform. (A) Schematic comparison of a glycoconjugate vaccine (e.g., the Prevnar family) and LEPS. (B) Schematic representation of the formulation procedure to generate the LEPS particle.

In the first experiments of the current work, we sought to establish an alternative to the Prevnar vaccine family, which rely on covalently attaching *S. pneumoniae* polysaccharide from specific serotypes to the immunogenic CRM197 protein (an inactivated mutant of the diphtheria toxin capable of amplifying immune reactivity of the conjugated polysaccharide components), resulting in so-called glycoconjugate vaccines (e.g., Prevnar 13 features 13 different serotype polysaccharides covalently attached to CRM197). As opposed to covalent polysaccharide-protein coupling, we utilized liposomal technology to encapsulate required polysaccharide content and to non-covalently attach and surface display the CRM197 protein (FIGS. 6 and 7; termed liposomal encapsulation of polysaccharides (LEPS)). By doing so, we achieved an in vivo antibody shift pattern from IgM to IgG and effectiveness in total antibody titers and protection against *S. pneumoniae* bacterial challenge comparable to Prevnar 13 (FIG. 1A-C). In these comparisons, the Pneumovax 23 vaccine (which contains purified CPSs from 23 serotypes) was also tested with reduced effectiveness (antibody class shift and titer and bacterial challenge protection) relative to Prevnar 13 and the LEPS formulation. Importantly, LEPS achieves glycoconjugate vaccine effectiveness through non-covalent co-localization of polysaccharide and CRM197. The option to scalably encapsulate additional polysaccharides within the LEPS formulation further highlights differences to current glycoconjugate vaccine options, which require successive effort and manufacturing cost with each covalent attachment of a new serotype CPS to CRM197, thus, limiting both broad vaccine coverage and global access (Gregorio, *Nat Rev Immunol* 14, 505-514 (2014)).

Figure 8:
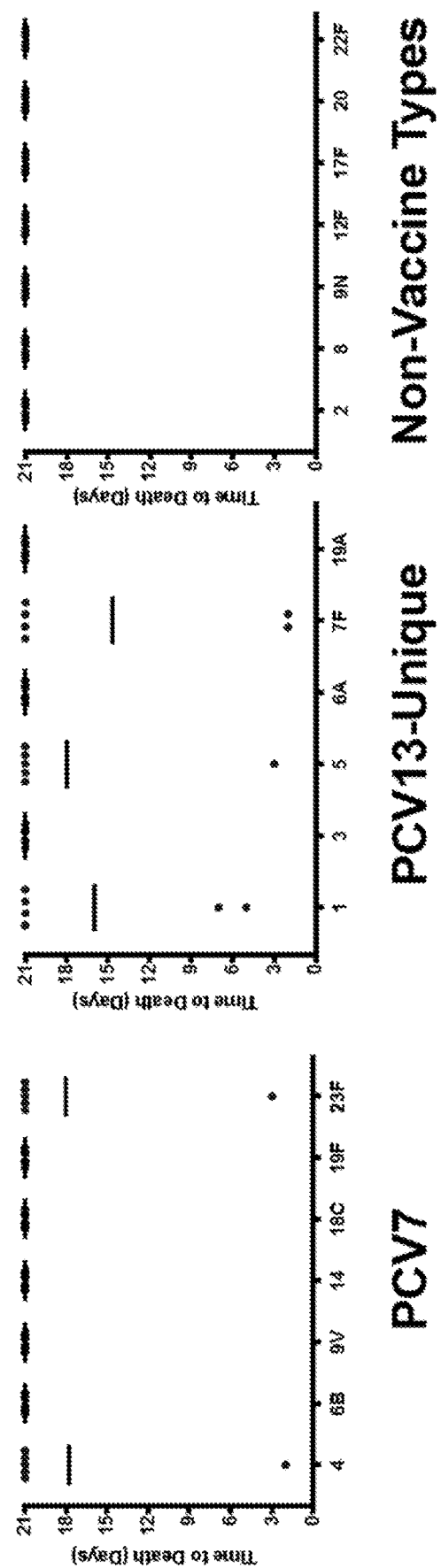
FIG. 8. Protective capabilities of LEPS immunizations when challenged with serotypes that span the current Prevnar 7 (PCV7) and 13 (PCV13) treatment options. Mice immunized with a LEPS formulation containing 20 polysaccharides (i.e., LEPS20) were evaluated in sepsis models and challenge strains (x-axis) are grouped into categories based upon inclusion in respective glycoconjugate vaccines. Specifically, the "PCV7" label includes bacterial serotypes covered by both Prevnar 7 and Prevnar 13; whereas, the "PCV13-Unique" grouping presents six additional serotypes covered by Prevnar 13. The "Non-Vaccine Types" label corresponds to serotypes not included in commercial glycoconjugate vaccines.
Figure 9:
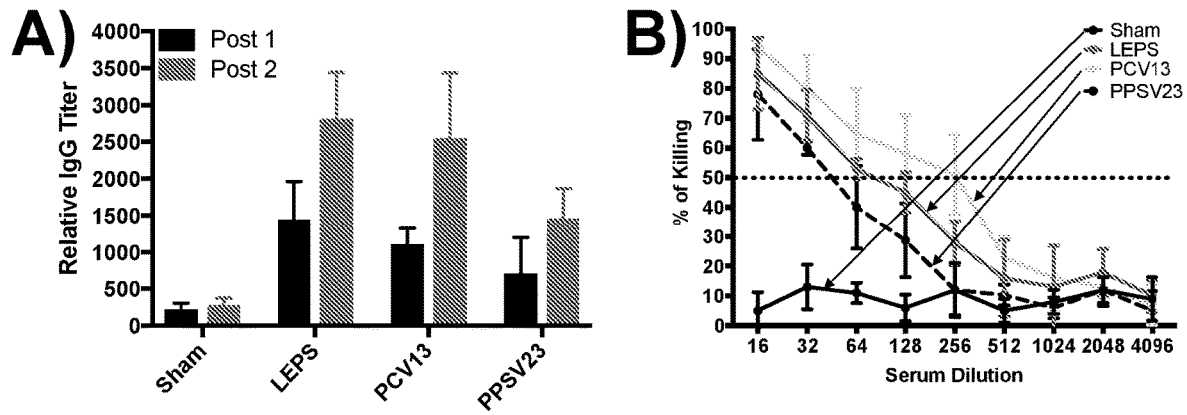
FIG. 9. LEPS vaccine strategy in rabbits. New Zealand White rabbits were immunized with LEPS particles containing *S. pneumoniae* serotype 19F CPS (day 0) and boosted (day 14) and peripheral blood samples analyzed for (A) total IgG titers at day 14 (Post 1; left bar) and 28 (Post 2; right bar) and (B) functional antibody activity (Post 2 samples) against serotype 19F via OPA assay.

Additional assays provided insight to the immune response afforded by the LEPS platform. Namely, FIG. 1D presents data from an opsonophagocytic activity (OPA) assay in which serum from immunized mice is added to the 19F *S. pneumoniae* serotype (recognized by current Prevnar and Pneumovax formulations) prior to co-culture with HL-60 human phagocytes. Bacterial killing is readily observed for all three vaccine formulations, with LEPS again performing at levels comparable to current standards. Table S1 (FIG. 15) presents a more thorough comparison of serotypes assessed via the OPA assay across the three vaccine systems. Similarly, FIG. 8 highlights effectiveness in protection against the serotypes covered by Prevnar 7 and 13 in addition to the seven non-vaccine serotypes included in the LEPS formulation. Nasal wash experiments indicate that the 19F *S. pneumoniae* serotype does not establish residence within the mouse nasopharynx due to the corresponding polysaccharide included in the three vaccine systems being compared in this case (FIG. 1E). Insight into immune response mechanism was provided by an anti-CD4+ T cell depletion assay in which antibody titers were significantly reduced, indicating antigen processing through a thymus-dependent pathway (FIG. 1F). Finally, antibody titers and OPA activity within rabbit subjects demonstrated consistent in vivo trends to those observed with mice subjects (FIG. 9).

Figure 2:
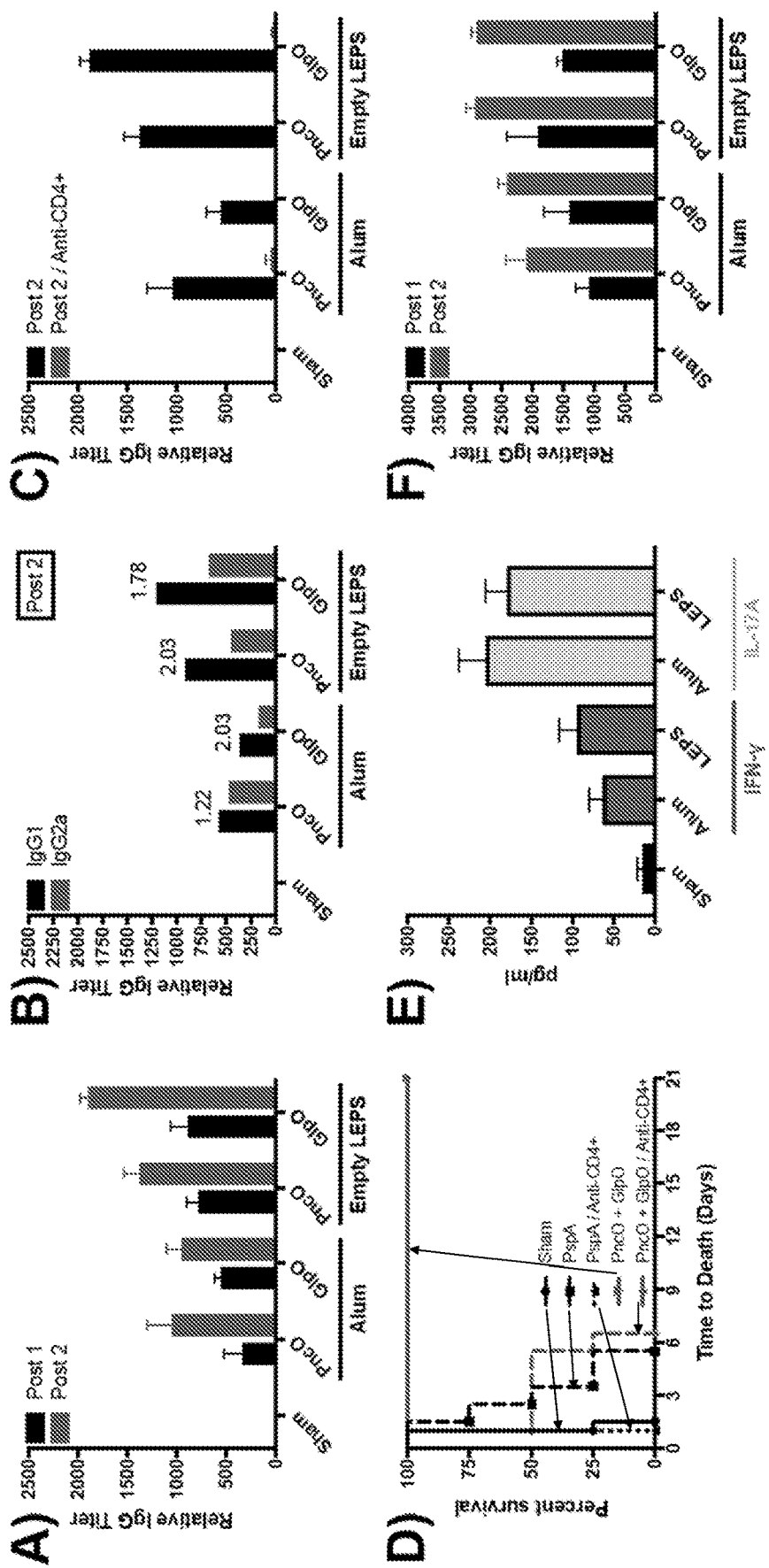
FIG. 2. Immune response assessment of the PncO and GlpO protein antigens. (A) Anti-PncO and anti-GlpO antibody titers in mice serum following initial (Post 1; left bar) and booster (Post 2; right bar) vaccination with either Alum adjuvant or empty LEPS. (B) IgG1 (Th2 corresponding; left bar) and IgG2a (Th1 corresponding; right bar) titers in mice serum following a booster vaccination; IgG1/IgG2a ratio is shown above the bars. (C) Anti-PncO and anti-GlpO antibody titers in mice serum without (left bar) or with (right bar) CD4+ T cell depletion. (D) Murine challenge-protection sepsis model post vaccination with either PspA (a commonly used pneumococcal protein antigen) (Li et al., Sci Adv 2, e1600264 (2016)) or PncO+GlpO with or without CD4+ cell depletion; S. pneumoniae serotype 19F was the challenge strain and four mice were used per formulation. (E) Titers of IFN-γ (Th1 corresponding) and IL-17A (Th17 corresponding) in mice serum following PncO+GlpO vaccination. (F) Anti-PncO and anti-GlpO antibody titers in rabbit serum following initial and booster vaccination.
Figure 5:
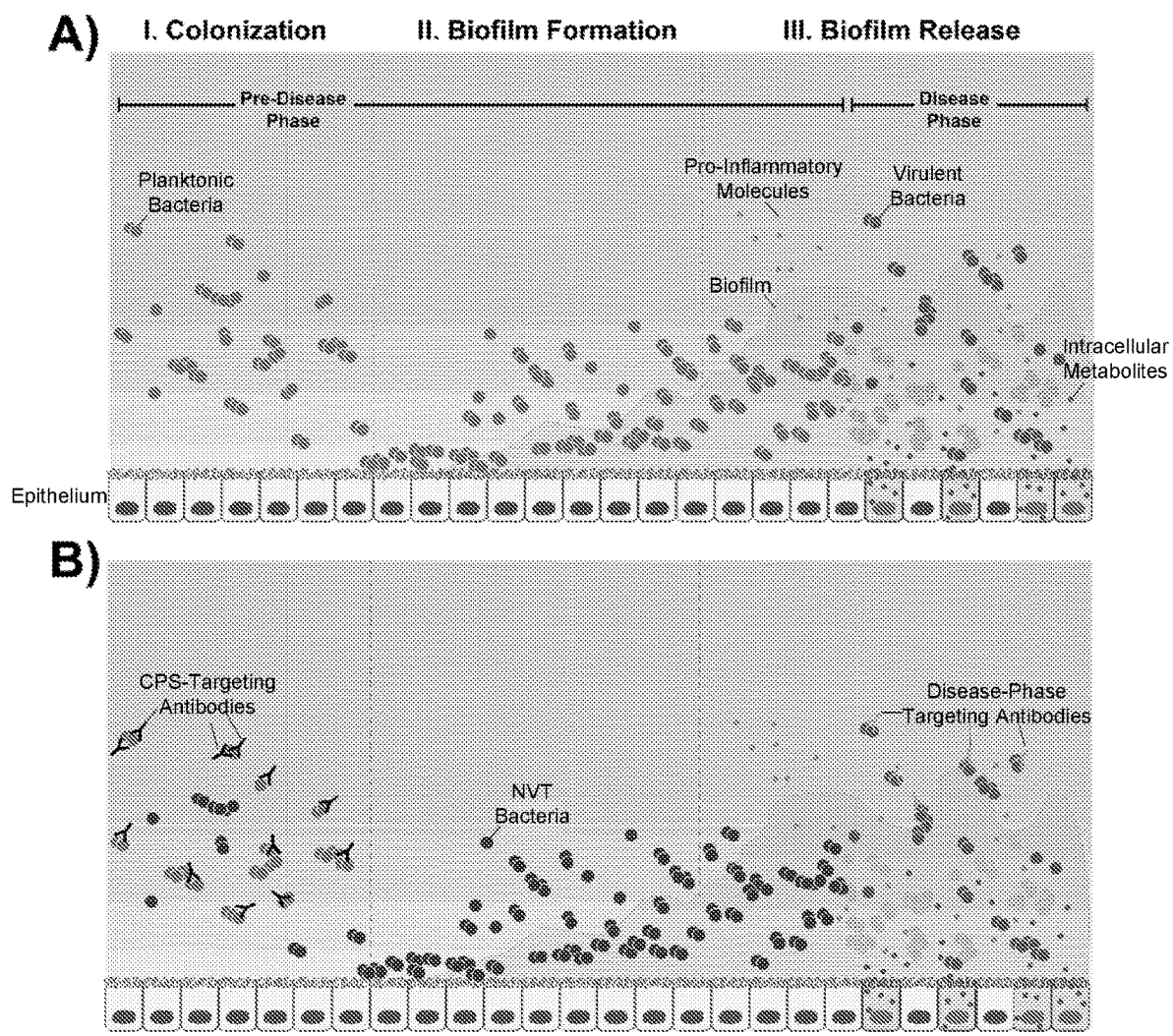
FIG. 5. Commensal disease progression model featuring pneumococcal disease. (A) *S. pneumoniae* colonization, biofilm establishment, environmental stimulation to virulence, and biofilm release and disease symptoms. (B) Immune targets that span current vaccine options (Prevnar and Pneumovax; capsular polysaccharide [CPS] targeting of specific serotypes) and the LEPS platform (addressing both colonization of currently-covered vaccine serotypes and biofilm release of nonvaccine-type [NVT] serotypes).
Figure 10:
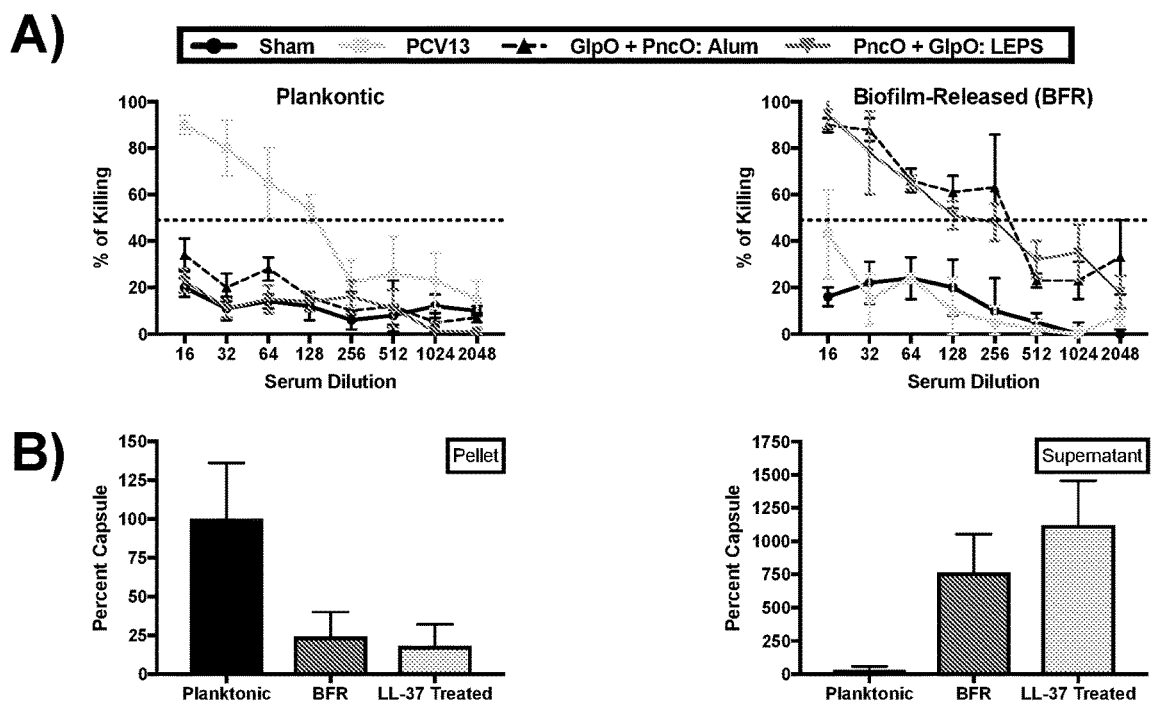
FIG. 10. OPA assay for GlpO and PncO directed against specific *S. pneumoniae* cell types. (A) OPA for planktonic (left) and biofilm-released (BFR) (right) serotype 19F bacteria mediated by serum from mice immunized with Prevnar 13 (PCV13), GlpO+PncO with Alum adjuvant, and GlpO+PncO with empty LEPS. (B) Capsular polysaccharide (CPS) content in the pellet (left) and supernatant (right) for planktonic bacteria, BFR bacteria, and planktonic bacteria treated with LL-37 to remove CPS; "Percent Capsule" values are relative to the planktonic samples in each sub-figure.
Figure 11:
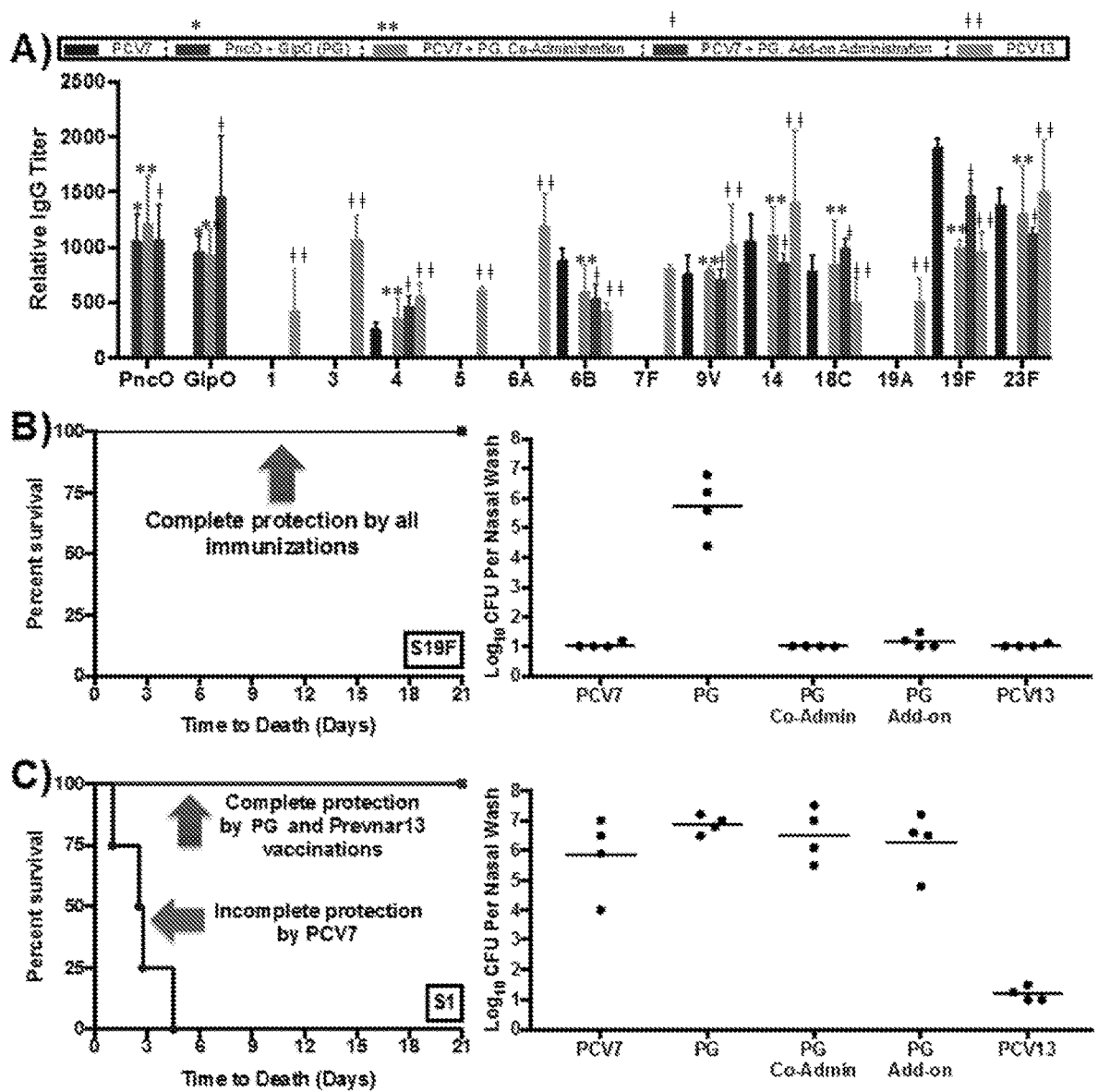
FIG. 11. Evaluation of immunogenicity of GlpO and PncO administered either jointly (co-administration) or as a booster (add-on) with Prevnar 7 (PCV7). (A) IgG titers against PncO, GlpO, and specific serotypes resulting from color-coded vaccination samples. (B) Mouse protection (left; sepsis challenge model) and bacterial burden (right; measured 5 days post-colonization) upon GlpO and PncO (PG) administration either jointly or as a booster with Prevnar 7. Mice were challenged with serotype 19F (covered by Prevnar 7 and Prevnar 13 [PCV13]) or 1 (not covered by Prevnar 7 but covered by Prevnar 13).

Expansive Protein Antigen Serotype Assessment and the Prospect of Universal Coverage The same liposomal technology that allowed an alternative pneumococcal disease vaccine has the interesting potential to address complementary aspects of commensal-based disease progression. Namely, the formulation offers the simultaneous encapsulation of polysaccharides (colonization immune targets) that serve as the basis for current vaccines in addition to the liposomal surface localization of protein antigens (GlpO and PncO; identified through an antigen discovery and validation model (Li et al., *Proc Natl Acad Sci USA* 113, 6898-6903 (2016)) that selectively target pneumococci virulence transition (FIG. 5). Before testing this possibility, the OPA assay enabled a more careful assessment of the GlpO and PncO protein antigens as a correlate-of-protection for future immunization experiments. In this case, however, the OPA assay assessed both colonization (planktonic cells containing surface CPS) and dispersion (biofilm-released cells displaying surface protein antigen targets) aspects of commensal disease progression in response to the corresponding polysaccharide or protein antigen component. The resulting insight contrasts traditional OPA assays that only assess planktonic CPS cellular targets and, hence, have an innate bias towards colonization prevention. As shown in Table S2 (FIG. 16) and FIG. 10, Prevnar 13, Pneumovax 23, and the GlpO/PncO protein antigens demonstrate specific activity for their respective cellular targets. Of note, the GlpO/PncO tandem is active for >70 biofilm-released serotypes of *S. pneumoniae*. This is the largest and most comprehensive assessment of advanced antigens for pneumococcal disease and, together with the high sequence conservation of the glpO/pncO genes across *S. pneumoniae* serotypes (Li et al., *Sci Adv* 2, e1600264 (2016)), emphasizes universal protection potential for any virulent-transitioned *S. pneumoniae* cell. The protein antigens were also tested more thoroughly for immune response mechanism (either within or separate from LEPS formulation), showing predominant Th2 response with contributing Th1 and Th17 activity in mice (FIG. 2A-E) and corresponding humoral response in rabbits (FIG. 2F). Supporting the complementary aspect of the antigen types, the PncO and GlpO proteins were tested in both a co-administration and add-on format with Prevnar 7, demonstrating protective capabilities by addressing commensal colonization, virulence transition, or both (FIG. 11).

A Comprehensive Vaccine Platform Through LEPS Technology

Figure 3:
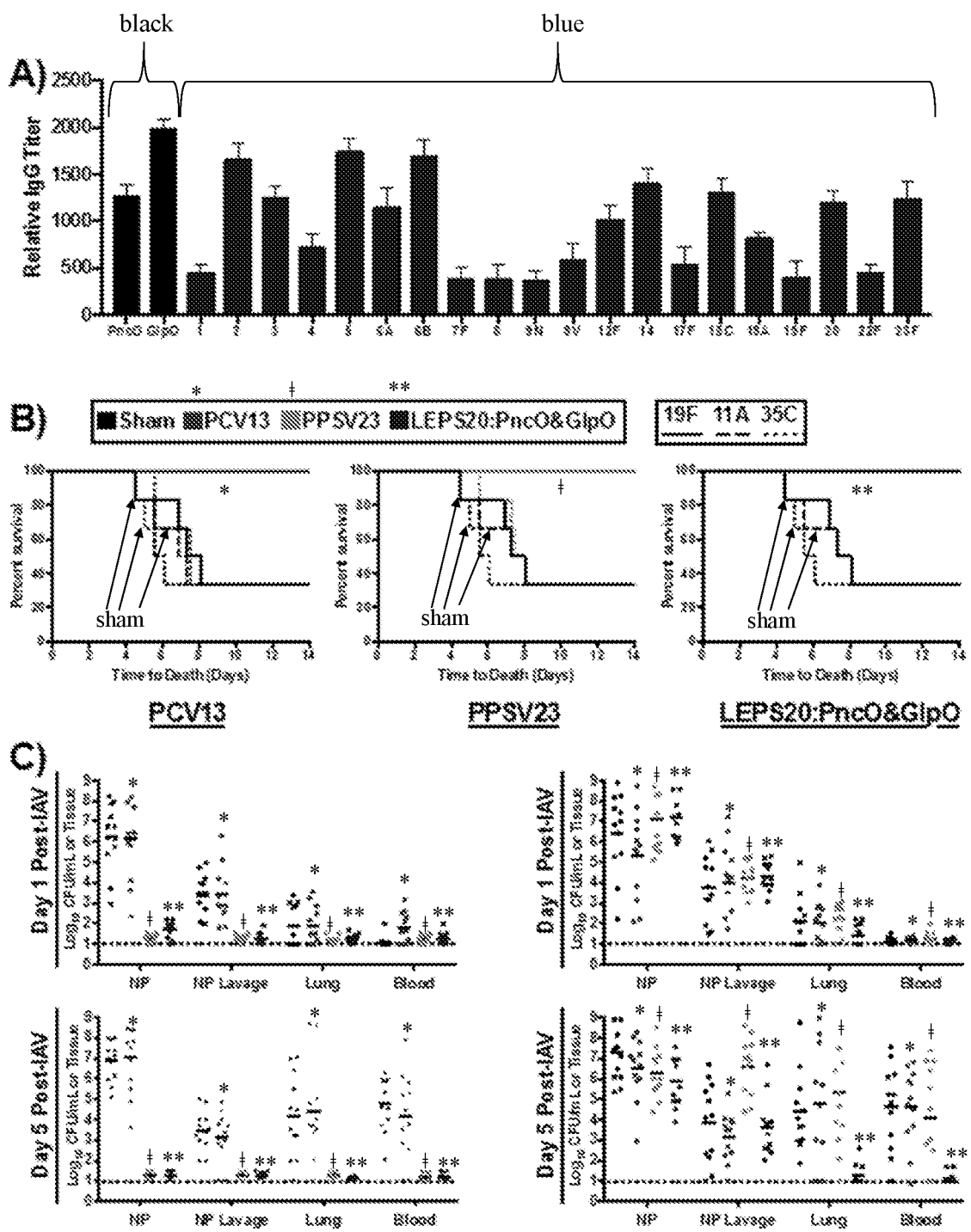
FIG. 3. Assessment of the full LEPS platform featuring CPS encapsulation across 20 serotypes and surface localization of GlpO and PncO. (A) IgG titers against PncO (1$^{st}$ bar from left), GlpO (2$^{nd}$ bar from left), and encapsulated CPS (remaining bars) from indicated *S. pneumoniae* serotypes in mice serum following vaccination. (B) Mouse challenge-protection data comparison between Prevnar 13 (PCV13), Pneumovax 23 (PPSV23), and the complete LEPS system (LEPS20:PncO&GlpO) using a colonization model and in vivo perturbation with influenza A administration to prompt pneumonia development. Survival is indicated across vaccination options when challenged with the indicated serotypes, which are partly covered by Prevnar 13 (19F) and Pneumovax (19F and 11A) and fully covered by LEPS20:PncO&GlpO. (C) Bacterial counts from the nasopharynx surface (NP), nasopharynx wash (lavage), lungs, and blood 1 and 5 days post-IAV administration when challenged with 11A (left) and 35C (right) serotypes.
Figure 12:
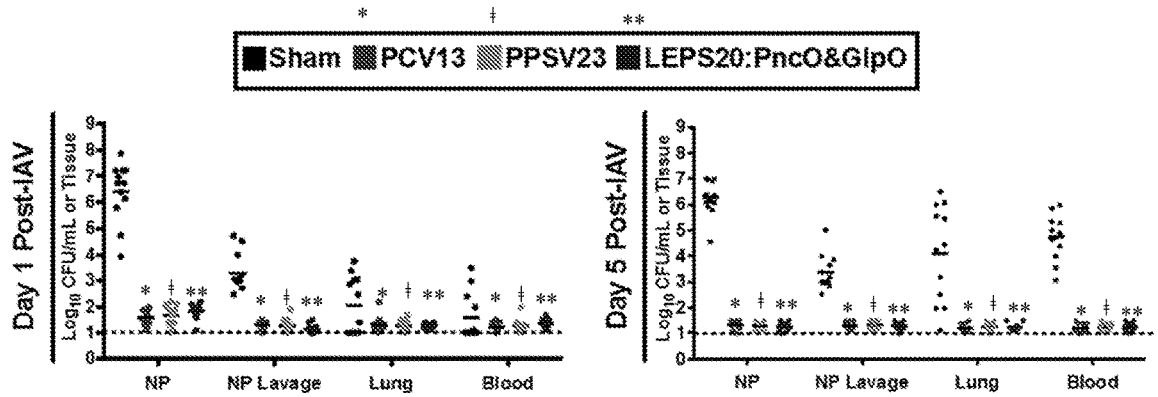
FIG. 12. Additional assessment of LEPS20:PncO&GlpO when using a murine IAV-induced pneumonia model with serotype 19F. Bacterial counts from the nasopharynx surface (NP), nasopharynx wash (lavage), lungs, and blood 1 and 5 days post-IAV administration. Prevnar 13 (PCV13); Pneumovax 23 (PPSV23).
Figure 13:
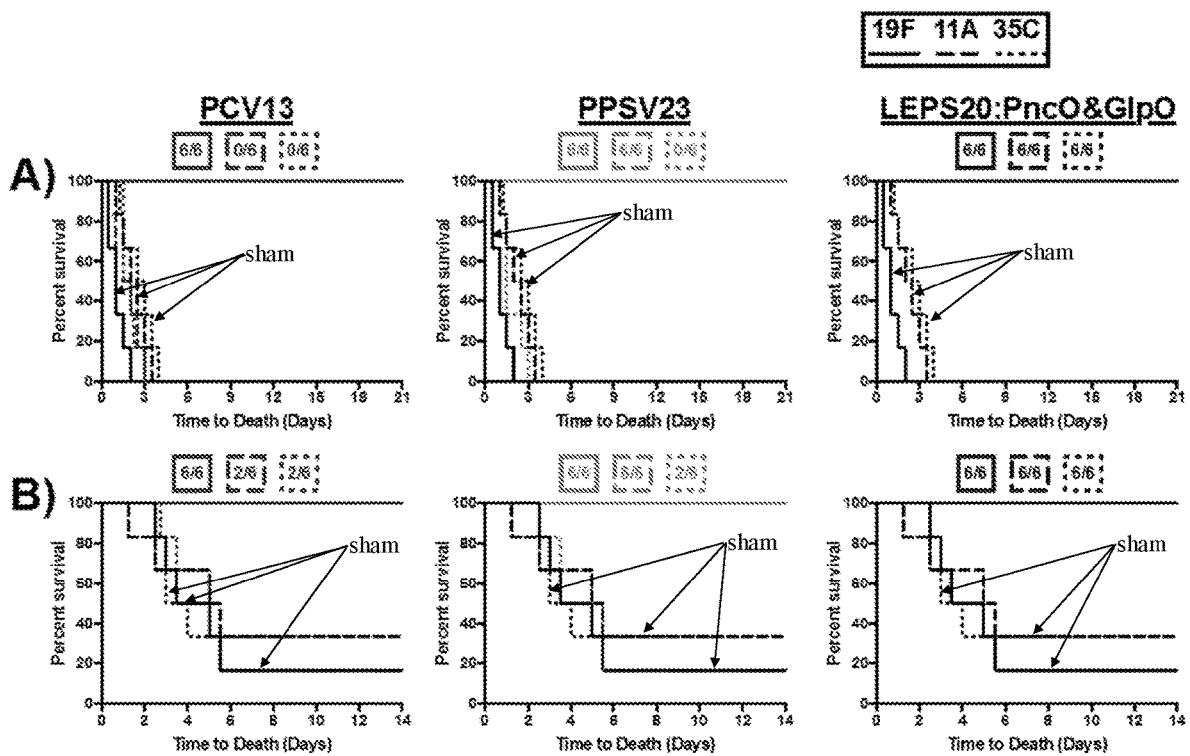
FIG. 13. Additional murine disease model assessment of LEPS20:PncO&GlpO. Mouse challenge-protection data comparison between Prevnar 13 (PCV13), Pneumovax 23 (PPSV23), and the complete LEPS system using (A) sepsis and (B) pneumonia disease models. Survival (animal numbers boxed) is indicated across vaccination options when challenged with the indicated serotypes, which are partly covered by Prevnar 13 (19F) and Pneumovax (19F and 11A) and fully covered by LEPS20:PncO&GlpO.

Next, coupling the PncO and GlpO protein antigens to the liposomal containment of polysaccharide resulted in the completed LEPS vehicle (LEPS20:PncO&GlpO; FIG. 3), thus, allowing for a final assessment of the commensal disease progression vaccination paradigm. From data within FIGS. 1 and 2, the complete LEPS vehicle was expected to possess ideal immune response characteristics (class switching, memory, broad T cell activation). Humoral response resulted for each of the antigen types within the completed vehicle (FIG. 3A) in addition to comprehensive and directed protection when tested within the in vivo influenza A virus (IAV)-prompted pneumonia model of pneumococcal disease transition. The challenge assays across strategic serotypes (19F [FIG. 12], 11A, and 35C) confirm the protective limits of Prevnar 13 and Pneumovax 23 and highlight the full protective capabilities of the complete LEPS system (FIG. 3B). Emphasizing antigen complementarity, the LEPS20: PncO&GlpO ormulation provides full protection even without the requisite CPS needed to prevent colonization by the 11A and 35C serotypes. The associated anatomical profiling further confirms the ability of the final LEPS formulation to inhibit disease dispersion of nonvaccine serotypes. Similar results accompany pneumonia and sepsis disease models (FIG. 13).

Figure 4:
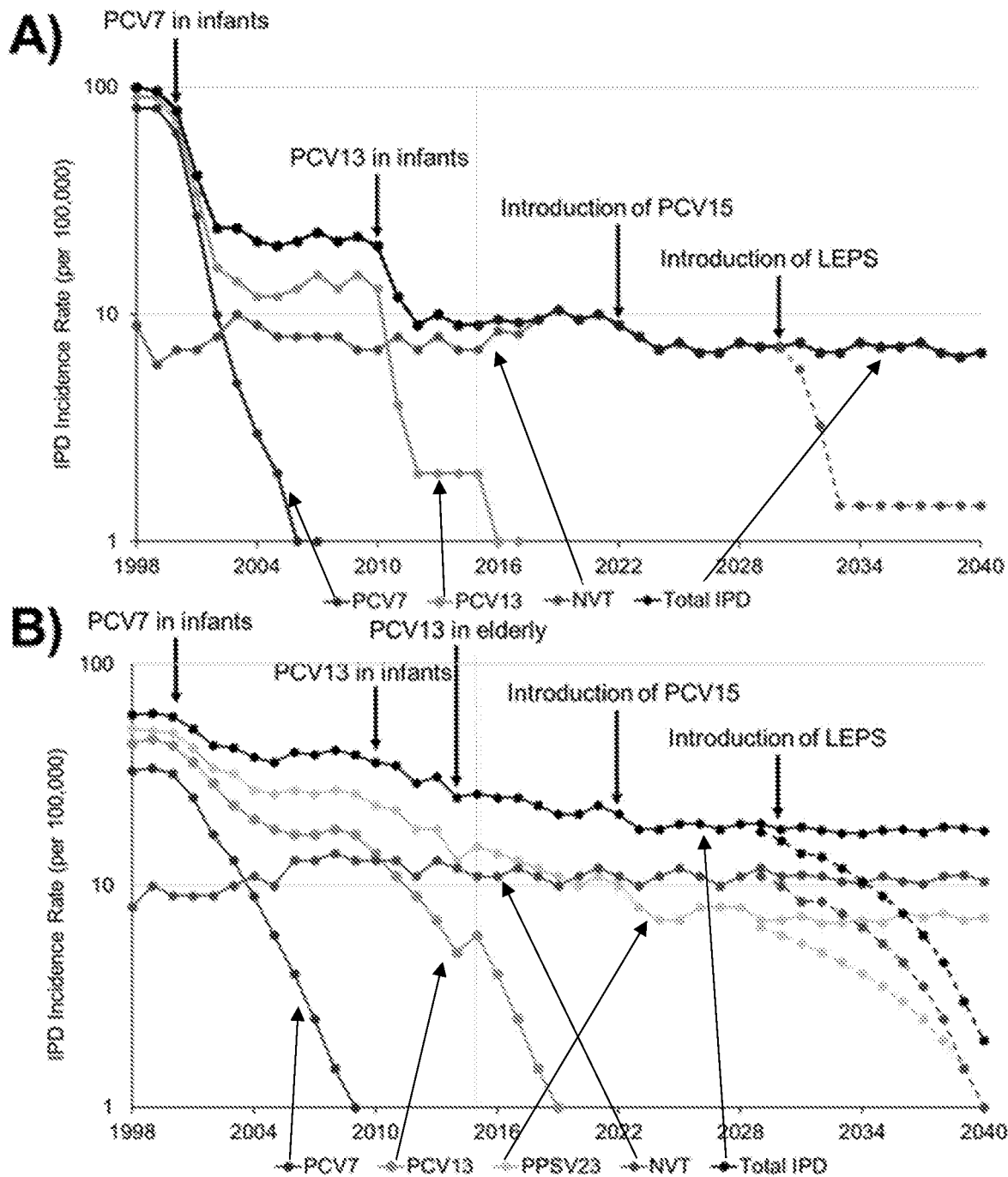
FIG. 4. Invasive pneumococcal disease (IPD) incidence rates in children (age<5; A) and the elderly (age≥65; B) from 1998 to 2040. The total incidence rate of IPD was segmented into disease caused by PCV7 (Prevnar 7), PCV13 (Prevnar 13), PPSV23 (Pneumovax), and nonvaccine-type (NVT) serotypes. NVT serotypes are defined as those not contained within PCV13 (A) or PPSV23 (B) vaccines. Incidence rates for PCV7 serotypes from 1998-2007 were obtained from studies published by Pilishvili et al., (*J Infect Dis* 201, 32-41 (2010)). Total incidence rates and incidence rates for PCV13 serotypes were obtained from the CDC's Active Bacterial Core (ABC) surveillance program for *S. pneumoniae* (https://www.cdc.gov/abcs/reports-findings/survreports/sp-neu-types.html). Incidence rates beyond 2007 (PCV7 serotypes) and 2015 (PCV13 serotypes) were predicted from trends observed in previous years. Reduction in total IPD following PCV15 (Prevnar 15) introduction was projected based on the serotype invasiveness (Brueggemann et al., *J Infect Dis* 190, 1203-1211 (2004); Sleeman et al., *J Infect Dis* 194, 682-688 (2006)) and prior trends for PCV7 and PCV13 with the rates stabilizing four years after introduction of the vaccine. Projections for IPD with (dotted lines) or without (solid lines) LEPS introduction were made beyond 2030. A reduction of IPD by 80% over four years (A) or 90% over 10 years (B) following introduction of LEPS was based on the 98% sequence coverage of the GlpO and PncO protein antigens (Li et al., *Proc Natl Acad Sci USA* 113, 6898-6903 (2016)) and activity demonstrated against 70 *S. pneumoniae* serotypes (FIG. 6).

Though the effectiveness of the LEPS vaccine was a key result, a broader implication is the dual potential for eliminating colonization of the most invasive serotypes of *S. pneumoniae* while simultaneously safeguarding against virulence transition of niche-replacement serotypes not covered by current vaccine formulations. This is possible because of the universal protection potential of the GlpO and PncO antigens (Table S2 (FIG. 16)), aided by sequence conservation across *S. pneumoniae* strains and the minimization of antigenic drift across multiple antigens. FIG. 4 provides a current and predicted timeline of invasive pneumococcal disease cases, which emphasizes the recalcitrance of nonvaccine serotypes and the potential of the LEPS formulation to address such concerns. Of note, the LEPS platform also provides a technically-feasible vision for universality through the prospect of encapsulating all known *S. pneumoniae* serotype polysaccharides (in addition to surface-displaying the GlpO and PncO protein antigens), an option that is economically infeasible with polysaccharide-protein coupling chemistry accompanying current glycoconjugate vaccine products. As such, the LEPS platform combines the best aspects of current vaccines while anticipating the basic tenets of commensal disease progression.

This disclosure provides that upon the co-localization of two complimentary antigens as a next-generation vaccine for pneumococcal disease. Without compromising the effectiveness of current vaccine designs, we introduce a modification that enables universality in vaccine response to disease. The resulting LEPS platform thus minimizes invasive serotype colonization while also safeguarding against virulence transition for all colonizing serotypes. As a result, the full disease progression pathway has guided the development of a vaccine that offers a comprehensive answer to the challenging aspects of addressing pneumococcal disease. More broadly, the concept outlined in this study seeks to balance benefits and drawbacks to microbial commensalism with an approach adjustable to eliminate or retain residence as a function of maximum benefit to the host.

Materials and Methods

Experimental Design. Complementary antigens derived from the understanding and analysis of commensal-based disease progression were co-localized using a liposomal carrier platform in the context of pneumococcal disease vaccination. Forms of assessment included liposomal vector characterization; tissue-specific disease progression; antibody, cytokine, and T cell depletion analysis; end-point and time-course challenge-protection assays; comprehensive opsonophagocytic activity assays; and tests conducted in mouse and rabbit models. Data uniformly supports a potent vaccination strategy capable of directing immune responses across the stages of commensal-based disease with the potential for universal coverage in the case of pneumococcal disease.

Ethics Statement. This study was carried out in strict accordance with the recommendations in the Guide for the Care and Use of Laboratory Animals of the National Institutes of Health. The protocols were approved by the Institutional Animal Care and Use Committee at the University at Buffalo. All bacterial inoculations and treatments were performed under conditions designed to minimize any potential suffering of the animals.

Reagents. Bacterial and cell culture media (including chemically defined bacterial growth medium [CDM]) and reagents were purchased from Fisher Chemical and Sigma-Aldrich. Sheep blood was purchased from Hemostat Laboratories. Lipids DOPG-Na and DSPE-PEG2000 were obtained from NOF; DOGS-NTA-Ni was purchased from Avanti Polar Lipids; DOPC, cholesterol, and alum (as aluminum phosphate), and polysaccharides were purchased from Sigma-Aldrich. LL-37 was purchased from InvivoGen. Prevnar 7 and 13 and Pneumovax 23 vaccines were obtained from Pfizer and Merck, respectively.

Antigen Preparation. All proteins (CRM197, green florescent protein [GFP], PspA, GlpO, and PncO) were recombinantly produced with polyhistidine tags through *E. coli*. Plasmids containing the genes for GFP, CRM197, and PspA were obtained through collaborative exchange (Li et al., *Sci Adv* 2, e1600264 (2016); Stefan et al., *J Biotechnol* 156, 245-252 (2011)). Remaining genes were PCR-amplified from *S. pneumoniae* genomic DNA and cloned into separate pET21c vectors using restriction sites SacI/XhoI (glpO) and NdeI/XhoI (pncO) introduced to the amplified products by the PCR primers (Li et al., *Proc Natl Acad Sci USA* 113, 6898-6903 (2016)). After plasmids were confirmed by restriction digestion and colony PCR, final constructs were chemically transformed into *E. coli* BL21(DE3) to confirm individual expression via induction of 3 mL lysogeny broth (LB) cultures at $OD_{600\,nm}$ values of 0.4-0.6 using isopropyl β-D-1-thiogalactopyranoside (IPTG; 1 mM) prior to analysis by SDS-PAGE. Confirmed expression prompted scaled 1 L cultures for expression and protein purification through disruption of cells using French press and passing cell lysate over a fast protein liquid chromatography column (GE Healthcare HisTrap HP, 1×1 mL). Final protein products were quantified using the Pierce™ Micro BCA™ Protein Assay.

Figure 14:
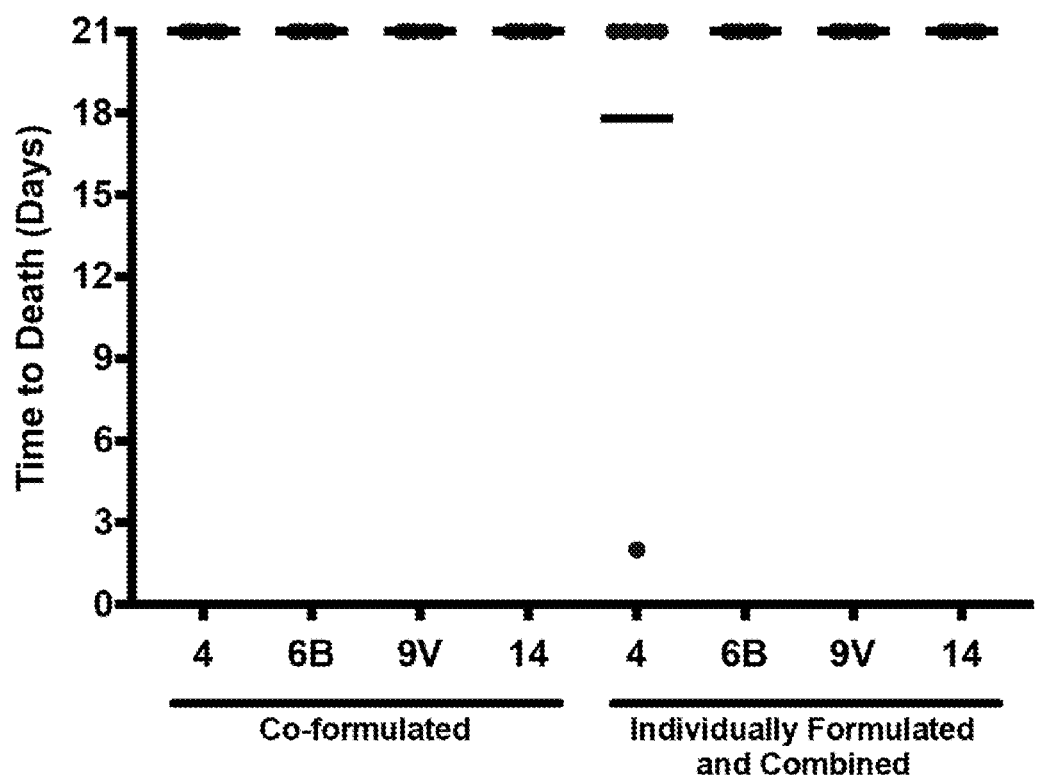
FIG. 14. Alternative LEPS formulation procedures and comparison within murine challenge-protection assays. Polysaccharides from *S. pneumoniae* serotypes 4, 6B, 9V, and 14 were either mixed and co-formulated during liposomal preparation or individually formulated within liposomal particles that were then combined prior to mouse vaccination. A sepsis disease model was then used to challenge the mice subjects with the individual serotypes (x-axis).

LEPS Preparation and Characterization. Proteins and polysaccharide components were co-localized through a liposomal delivery system. LEPS liposomal carriers were comprised of DOPC:DOPG:DOGS-NTA-Ni:cholesterol:DSPE-PEG2000 at a molar ratio of 3:3:1:4:0.1 to a total lipid mass of 500 μg. After dissolving lipids in chloroform, the solution was sonicated for 1 minute using a Branson 450D Sonifier (at 20% amplitude using a tapered tip) and then evaporated using a rotary evaporator to form a film. Lipids were then rehydrated with phosphate buffered saline (PBS) containing the polysaccharide antigens to form liposomes, which were then passed 10-12 times through a handheld extruder (Avanti Polar Lipids) with a pore size of 200 nm. On ice, the background liposome solution was passed twice through a 50 nm pore size filter and replaced each time with PBS. Next, proteins were incubated with liposomes for 30 minutes at 4° C. with surface attachment mediated via polyhistidine tag-Ni chelation. CRM197 was included in the LEPS formulations used for FIG. 1; FIG. 8; FIG. 9; FIG. 14; and Table 51 (FIG. 15); CRM197 was not included (replaced by GlpO/PncO) in the LEPS formulations used for FIG. 2; FIG. 3; FIG. 10; FIG. 12; and FIG. 13. At this stage, any unbound protein and polysaccharide was separated from the final LEPS construct via overnight dialysis (100 kDa MWCO) at 4° C. Throughout the study, final formulations used during vaccinations were comprised of mixtures of LEPS particles containing individual polysaccharides. For example, the final 20 valent CPS LEPS formulation resulted from mixing 20 individually-prepared samples. Alternatively, a co-formulation approach was also tested (with a limited number of serotype polysaccharides) and compared to the mixing approach described directly above with no differences in final vaccine protection (FIG. 14). All final LEPS formulations were prepared to deliver the same amount of polysaccharide content (and CRM197 protein, as needed) utilized within Prevnar and Pneumovax formulations, which were diluted 1:10 in PBS prior to immunizations.

Figure 7:
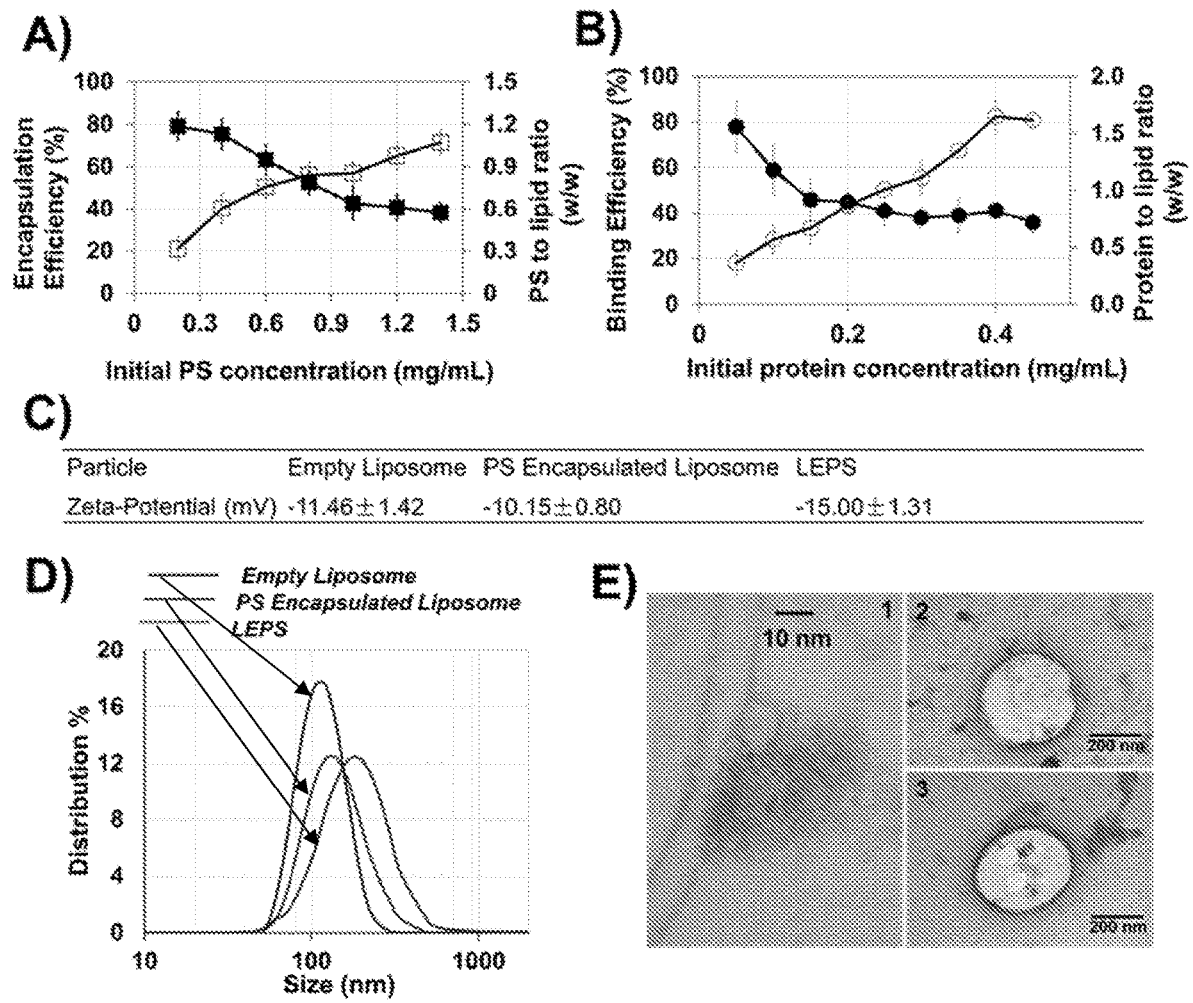
FIG. 7. LEPS characterization. Polysaccharide (PS) encapsulation efficiency (A; solid squares) or protein surface binding efficiency (B; solid circles) vs. initial concentration. Particle surface charge evaluation (C) and size distribution (D). (E) LEPS particle image by transmission electron microscopy; 1: LEPS surface; 2: PS Encapsulated Liposome; 3: LEPS.

Characterization of the LEPS particles began by analyzing polysaccharide encapsulation and surface protein binding efficiency. Quantification was completed over a range of polysaccharide (using 19F) or protein (using GFP) to lipid ratios to identify the crossing point of efficiency (FIG. 7). For polysaccharide evaluation, concentrated sulfuric acid (150 μL) and 30 μL phenol (5% w/v) were added to 50 μL of liposome solution followed by incubation at 80° C. for 30 min and 22° C. for 30 min prior to colorimetric analysis at 495 nm. Protein content was measured via fluorescence analysis at an excitation wavelength of 359 nm and an emission wavelength of 508 nm. Both analyses were conducted using a Synergy 4 Multi-Mode Microplate Reader (BioTek Instruments, Inc.) and measured values were compared to standards (using either glucose or GFP) and ratioed to initial amounts of polysaccharide and protein introduced to the LEPS production process. Dynamic light scattering (DLS) on a Zetasizer nano-Z S90 (Malvern, Inc.) was used to evaluate the particle diameter and zeta potential of liposomes at 25° C. All experiments were conducted using a 4 mW 633 nm HeNe laser as the light source at a fixed measuring angle of 90° to the incident laser beam. Images of the LEPS particles were obtained through JEOL JSM-CXII transmission electron microscopy analysis at 100 kV with samples prepared by dip coating a 200 mesh formvar and carbon coated grid (FCF-200-Cu-TB, Electron Microscopy Sciences), followed by negative staining using a 1% solution of uranyl acetate.

Vaccine Immunization. Outbred 6-week-old female CD-1 mice (Harlan Laboratories) were used in immunization experiments. Mice were immunized by subcutaneous injection (200 μL); background solution for formulations was PBS ("sham" negative controls were background solutions administered without antigen components). Final protein antigen levels were 12.5 μg in either naked or liposomal formulations (GlpO, PncO, CRM197, and PspA). When combined, PncO and GlpO were administered at 6.25 μg each. Unless indicated otherwise, alum adjuvant was added to protein samples according to manufacturer instructions. After 14 days, mice were boosted with the same formulations; serum samples were collected on days 14 and day 28 by retro-orbital bleeding for antibody and OPA analyses. Four-month old New Zealand White rabbits (Cocalico Biologicals) were immunized through intramuscular administration of 500 μL of respective samples at days 0 and 14; peripheral blood samples were collected on days 14 and 28 for antibody and OPA analyses.

Bacterial Preparation and Biofilm Release. Bacterial strains used in this study were initially grown on Todd-Hewitt agar plates supplemented with 0.5% yeast extract and 5% sheep blood and incubated overnight at 37° C. Single colonies were used to inoculate 5 mL Todd-Hewitt broth containing 0.5% yeast extract and incubated at 37° C. to an $OD_{600}$ of 0.6. At this point, bacteria were collected by centrifugation, washed once with and resuspended in PBS, and quantified by $OD_{600}$ measurement for experiments requiring planktonic cells. Planktonic cells were introduced to the in vitro biofilm model and were utilized within all OPA assays (unless specifically indicated otherwise), mouse colonization analyses, and in vivo influenza-induced pneumonia models.

To establish biofilm conditions, NCI-H292 epithelial cells (CRL-1849; ATCC) were first cultured in RPMI-1640 medium with the addition of fetal bovine serum in T75 flasks at 37° C. and 5% $CO_2$. After reaching 100% confluency, H292 cells were prefixed in 4% buffered paraformaldehyde at 34° C. for 48 hours followed by three washes with PBS. CDM-grown pneumococci were then seeded onto fixed H292 cells with change of media occurring every 12 hours. Formed biofilms were exposed to heat (38.5° C.) for 4 hours and released cells were then collected by centrifugation, washed once with and resuspended in PBS, and quantified by $OD_{600}$ measurement. Experiments utilizing biofilm-released cells included in vivo sepsis and pneumonia models.

Challenge Models. Mice were challenged with $1\times10^4$ (sepsis model) or $1\times10^6$ (pneumonia model) colony forming units (CFU) of pneumococci strains through intraperitoneal or intranasal (with isoflurane) administration, respectively. To induce colonization, mice were administered $1\times10^6$ CFU bacteria intranasally without isoflurane. To prompt influenza-induced pneumonia, pneumococci colonization was followed by intranasal inoculation with 40 plaque forming units of IAV (strain A/PR/8/34 [H1N1; ATCC VR-95]; titers determined by plaque assays). Mice were monitored every four hours for signs of morbidity (huddling, ruffled fur, lethargy, and abdominal surface temperature). Mice found to be moribund were euthanized via $CO_2$ asphyxiation and cervical dislocation.

Antibody Analysis. Antigen antibody titer analysis was conducted as described previously (Li et al., *Sci Adv* 2, e1600264 (2016)) with the method extended to include 20 polysaccharides from associated serotypes and the GlpO and PncO protein antigens. Thus, an analysis was extended to all antigens utilized within the study. Cytokine measurements were accomplished using IFN-γ and IL-17A ELISA kits (R&D Systems).

Tissue Bacterial Count. At 5 days post-colonization, samples were analyzed as presented in FIG. 1E and S7B&C. Following influenza-induced pneumonia, mice were analyzed at 1- and 5-days post IAV administration, as indicated, or upon becoming moribund and a combination of nasopharynx tissue, nasopharyngeal lavage fluid, lung, and blood samples was collected and bacterial burden determined as described previously (Tyx et al., *J Bacteriol* 193, 3512-3524 (2011)). Briefly, tissue and organ homogenate, lavage fluid, and blood were homogenized to ensure dissociation of bacterial aggregates and then serially diluted on tryptic soy and 5% blood agar plates prior to enumeration.

CD4$^+$ Depletion. For in vivo CD4$^+$ T cell depletion, 0.5 mg of anti-CD4$^+$ monoclonal antibody (Invitrogen) was injected intraperitoneally into mice for three consecutive days. After day six, a T cell depletion of ≥95% was confirmed using flow cytometry, and these mice subjects were then utilized in the indicated experiments.

OPA Analysis. Extending upon a previous protocol (Romero-Steiner et al., *Clinical and Vaccine Immunology: CVI* 13, 165-169 (2006)), human HL-60 cells were differentiated with dimethlyformamide to quantify antibody-mediated opsonophagocytosis and killing of *S. pneumoniae* exposed to dilutions of sera collected from immunized mice subjects to identify the 50% killing endpoint (quantified by CFU counts). Incubation of HL-60 and pneumococci was for 75 minutes.

Statistical Analysis. Comparisons were analyzed for statistical significance using a two-tailed Student t test for unpaired data through the GraphPad Prism software (version 6.0 h.283; GraphPad Software Inc., La Jolla, Calif.). All data resulted from a minimum of three samples with animal experiments using between four to twelve subjects.

EXAMPLE 2

In this example, we developed another embodiment of the LEPS formulation that addresses potential safety concerns and establishes a desirable pneumococcal vaccine. Safety concerns were addressed by evaluating the potential off-target immunogenicity associated with GlpO and assessing alternative protein-liposome attachment strategies to eliminate the dependence on his-tagged proteins (and eliminate the potential introduction of a neoantigen). In so doing, we removed GlpO from the formulation while retaining biofilm breakthrough virulent targeting through the dose-escalation of PncO and expanding the vaccine to include 24 CPSs. We then assessed a comprehensive LEPS design, using a single-dose escalation study. These studies represent a significant step in the development of a universal pneumococcal vaccine.

Results

Risk Assessment for Off-Target Immunogenicity Associated with GlpO

Figures 17, 18:
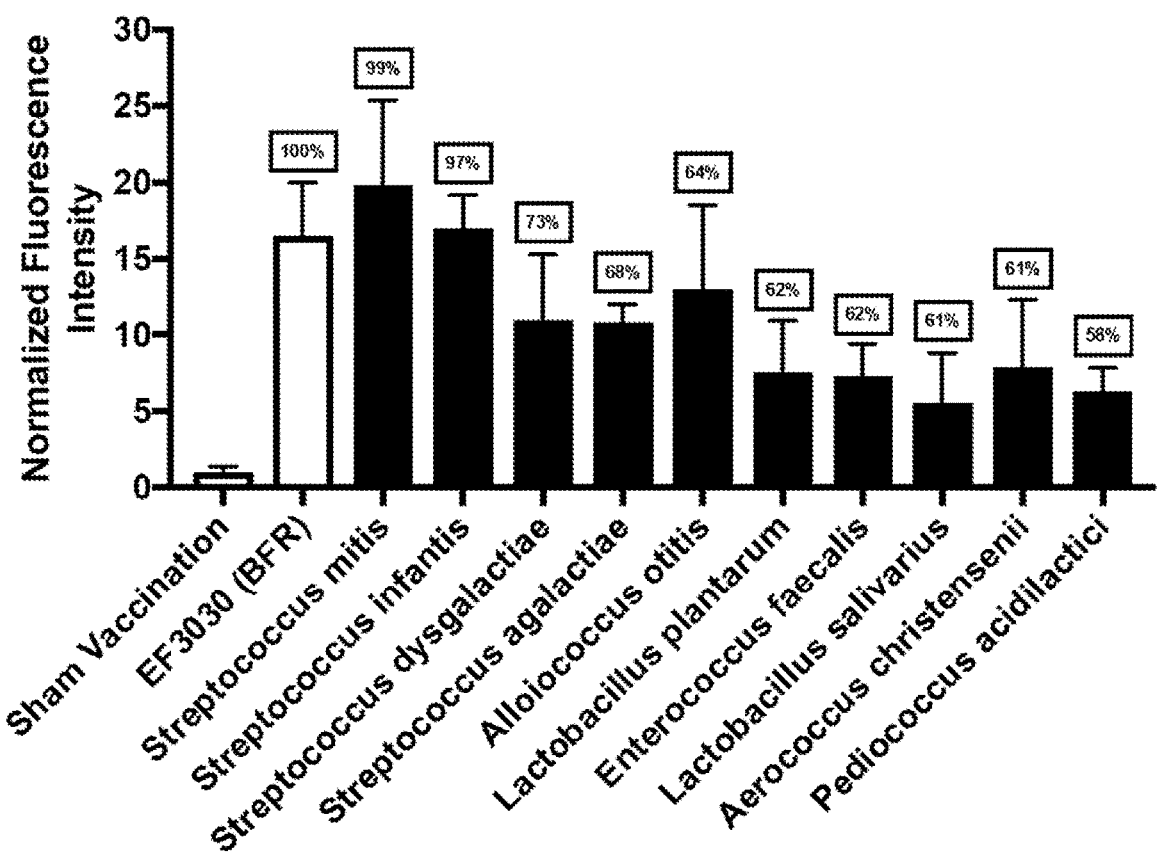
FIG. 17 (Table S3). GlpO and PncO summary.
FIG. 18: Vaccination with GlpO demonstrates a risk for potential off-target immunogenicity. A) Normalized fluorescence intensity relative to sham vaccination for each respective bacterial species (e.g., sham vaccination readings of one represent different absolute fluorescent readings for each bacteria); boxed numbers represent homology shared with predicted protein epitopes of GlpO. B) OPA assay results for BFR EF3030, *Streptococcus agalactiae, Lactobacillus salivarius, Lactobacillus platarum*, and *Pediococcus acidilactici*. The dashed line represents 50% killing of bacteria. Error bars represent the standard deviation of four technical replicates.
Figure 18:
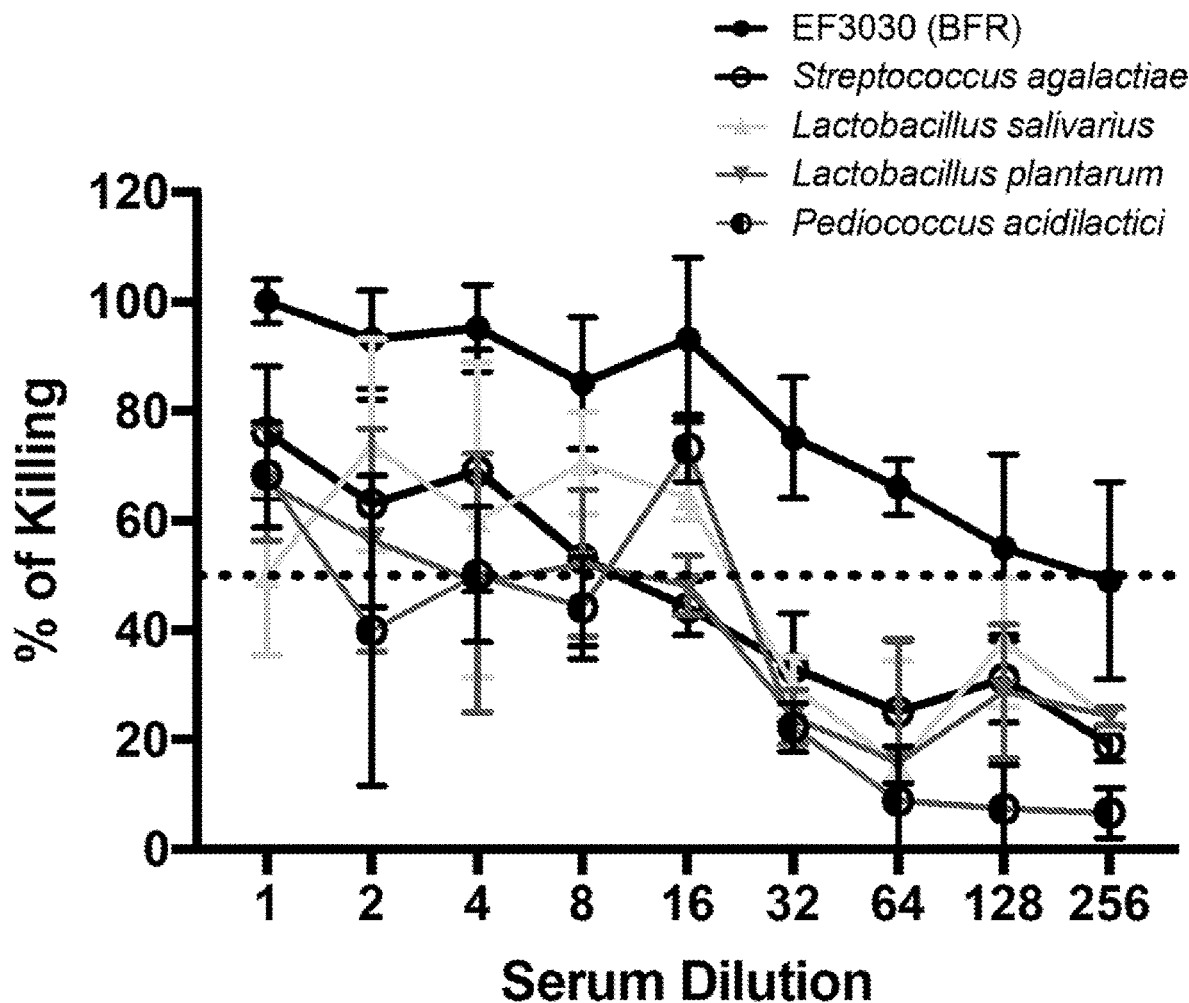

The *S. pneumoniae* GlpO and PncO protein antigens risk immune reactivity to homologous targets within native microflora. Though no negative toxicological scoring was observed within initial immunization studies, a sequence homology search was conducted for the GlpO and PncO proteins against targets in human commensal bacteria using a 50% BLAST homology screen. While no hits were identified for PncO, a substantial number of microflora protein targets were found to possess >50% homology to GlpO (Table S4 (FIG. 27)). From the subset of bacteria identified, ten species, representing diverse homology and physiological locations, were selected for further analysis (FIG. 18).

Figure 24:
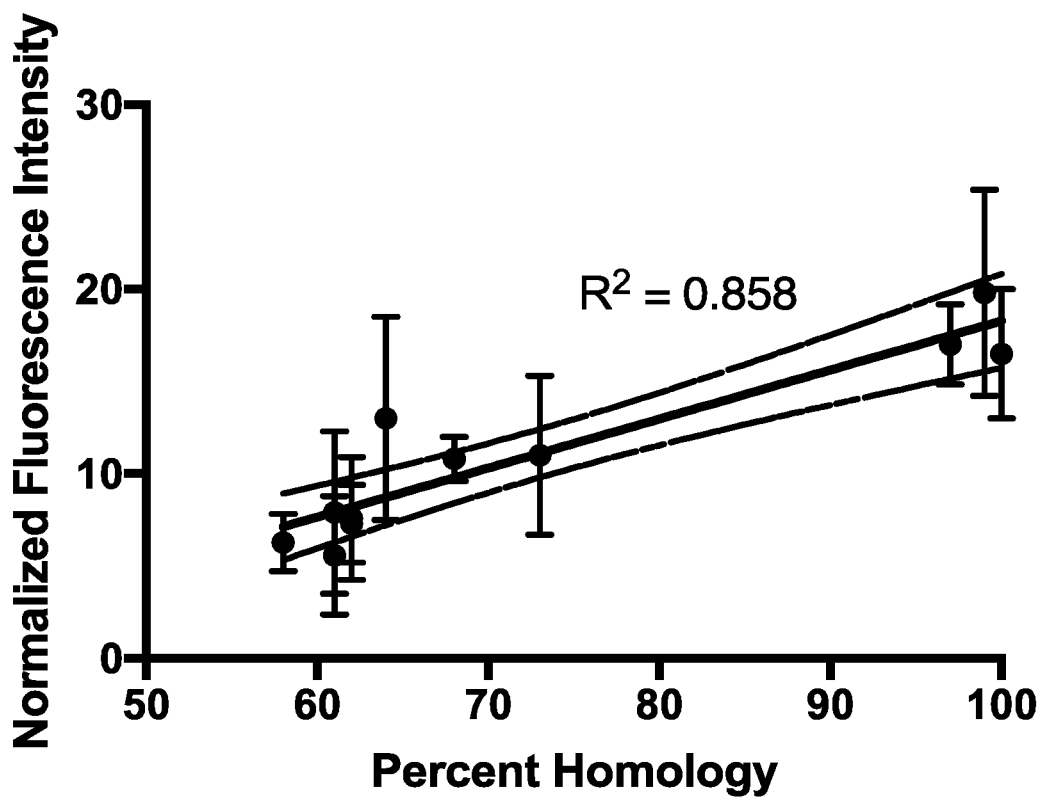
FIG. 24: Correlation between immunofluorescence assay results and bacterial homology with GlpO. Dotted lines represent the 95% confidence interval.

Serum from GlpO-vaccinated mice was then tested within an immunofluorescence assay to determine whether antibodies against *S. pneumoniae* GlpO demonstrated off-target bacterial binding. Strong antibody binding towards tested bacterial species was observed relative to a sham vaccination (FIG. 18A). In addition, immunofluorescence for several species was comparable to that obtained for the *S. pneumoniae* EF3030 (19F) strain, which is a direct target of the GlpO vaccine. When immunofluorescence was evaluated in the context of protein homology (FIG. 24), a significant positive correlation ($R^2=0.858$) was observed, indicating that the observed strength of binding is related to sequence homology. Given the observed off-target antibody binding, an OPA assay was performed using four representative species to determine whether the resulting antibody binding possessed neutralization activity. As shown in FIG. 18B, significant killing activity was observed for each bacterial species compared to BFR EF3030. Taken together, these results suggest that vaccination with GlpO could impact the human microbiome.

Protein Antigen Dose-Escalation in LEPS(20V) Formulation

Figure 19:
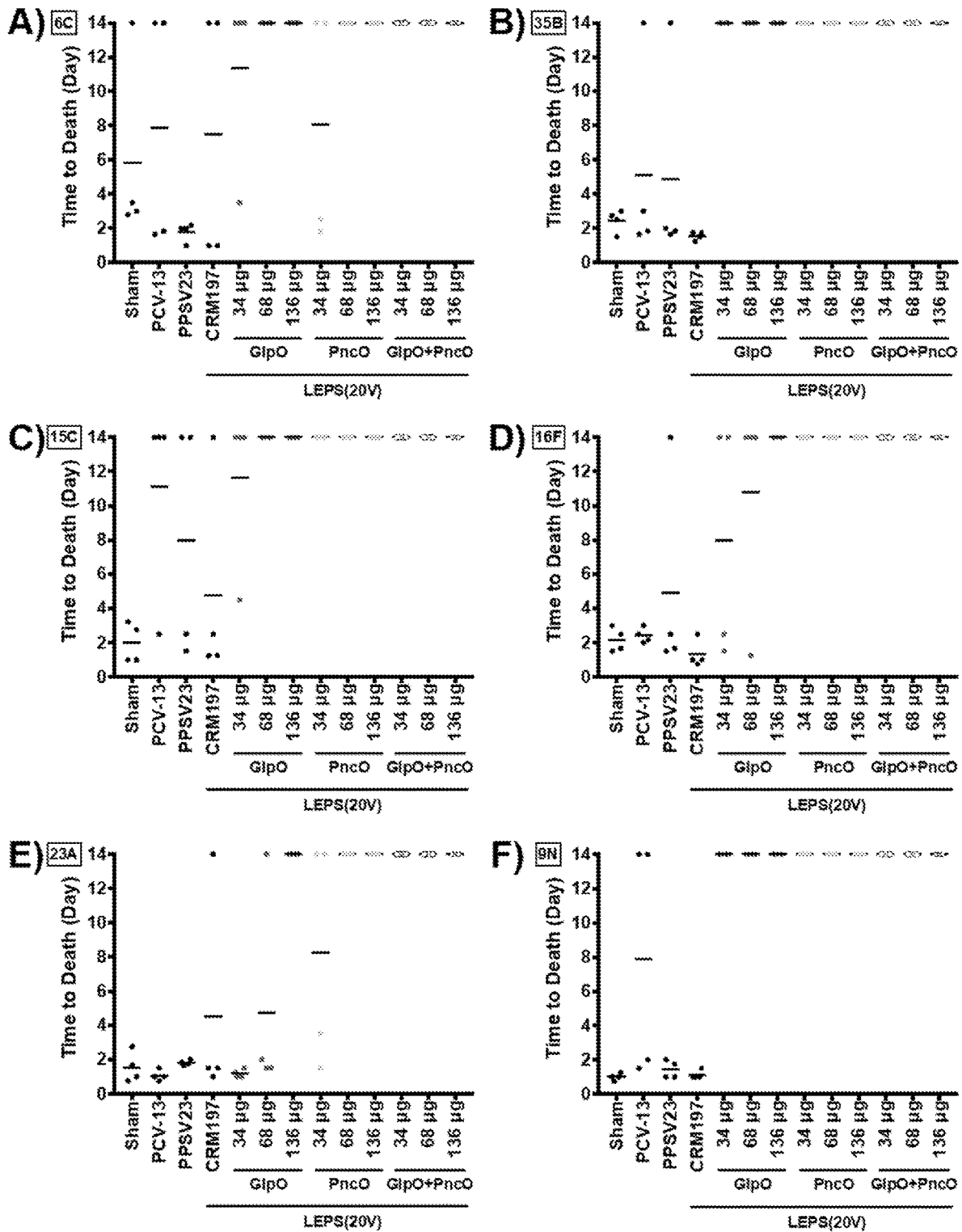
FIG. 19: Time to death in BFR pneumonia challenge model. Serotypes tested included 6C (A), 35B (B), 15C (C), 16F (D), 23A (E), and 9N (F). Four CD-1 mice were vaccinated with either a sham control, PCV13, PPSV23, and LEPS(20V) with CRM197, GlpO, PncO, or GlpO+PncO. Doses represent the micrograms of each protein (34, 68, or 136 μg).

In an effort to establish dose limits and assess individual effectiveness for protein antigens, immunogenicity and OPA assessment of the 20-valent LEPS (LEPS(20V)) vaccine formulation with varying doses (34, 68, or 136 μg) of GlpO and PncO was conducted. Vaccine efficacy was determined using a BFR pneumonia challenge model spanning six vaccine and NVT serotypes (6C, 35B, 15C, 16F, 23A, and 9N). As shown in FIG. 19, vaccination with GlpO, PncO, and GlpO+PncO substantially improved survival for all tested serotypes compared to Prevnar 13® (PCV13) and Pneumovax 23® (PPSV23). In addition, vaccination with GlpO and/or PncO in LEPS(20V) improved survival across all serotypes compared to LEPS(20V) formulated with CRM197. This is indicative that protection against NVT bacteria (i.e., the CPS are not included in LEPS) arises due to inclusion of the pneumococcal breakthrough virulence proteins. Although incomplete protection was observed for GlpO or PncO for the 6C, 15C, 16F and 23A serotypes at the initial dose of 34 μg, we observed that increasing the dose was able to restore 100% protection comparable to the vaccine formulation combining the proteins.

Figure 20:
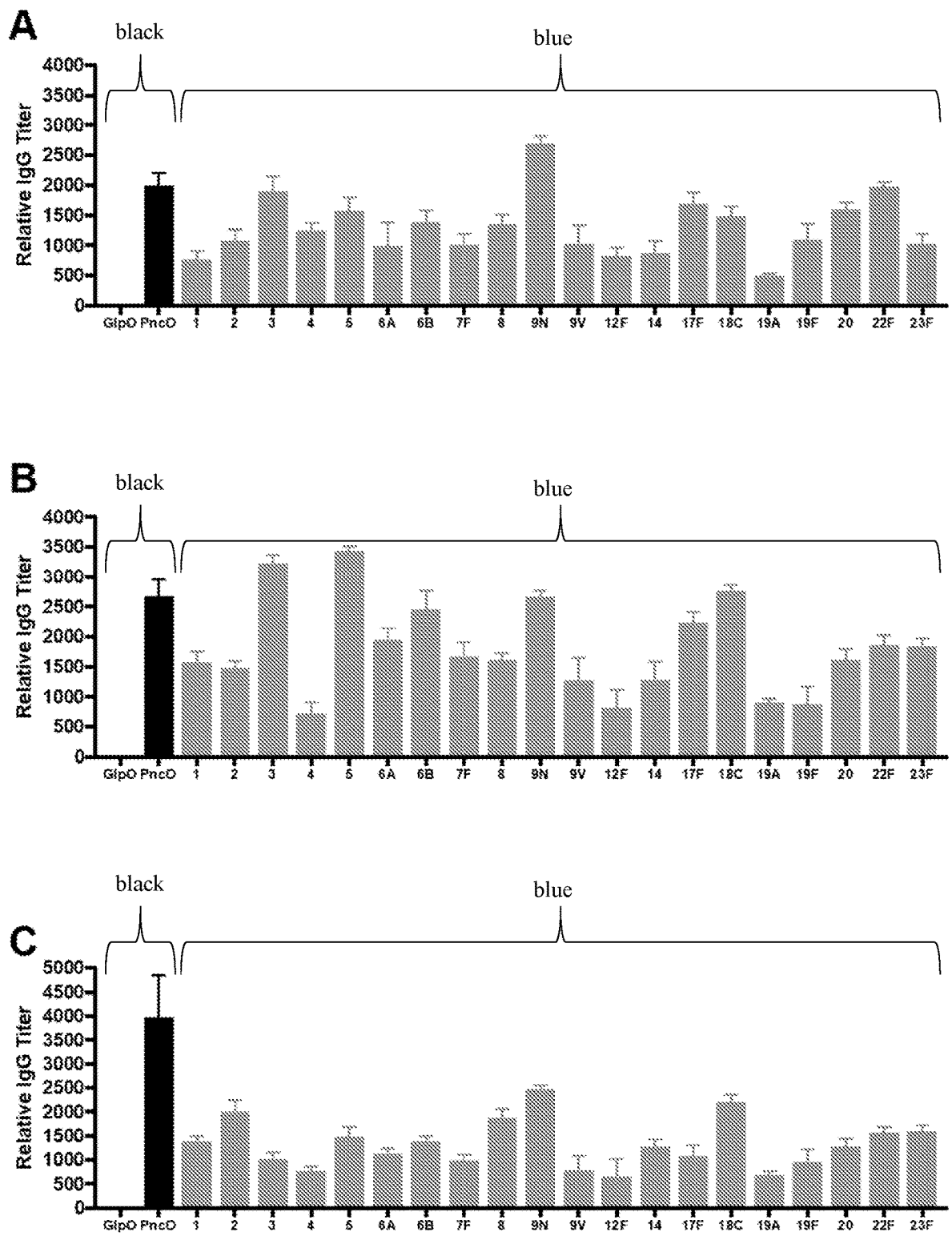
FIG. 20: Relative antibody titers for protein (black) and CPS (blue) antigens in LEPS(20V):PncO dose escalation study. CD-1 mice were vaccinated subcutaneously with LEPS(20V):PncO at 34 (A), 68 (B), and 136 μg (C) of PncO. Error bars represent the standard deviation of four biological replicates.
Figure 28:
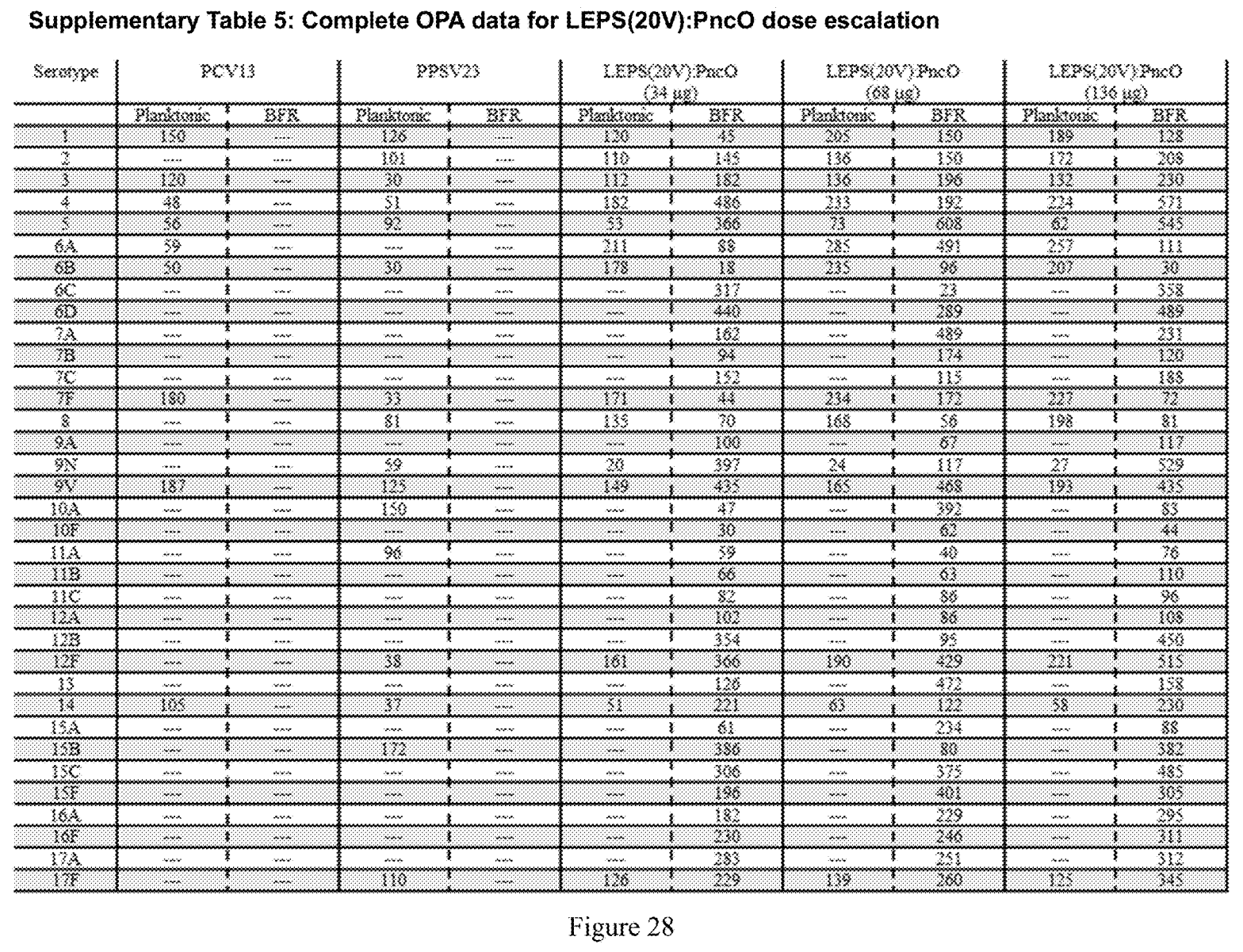
Figure 29:
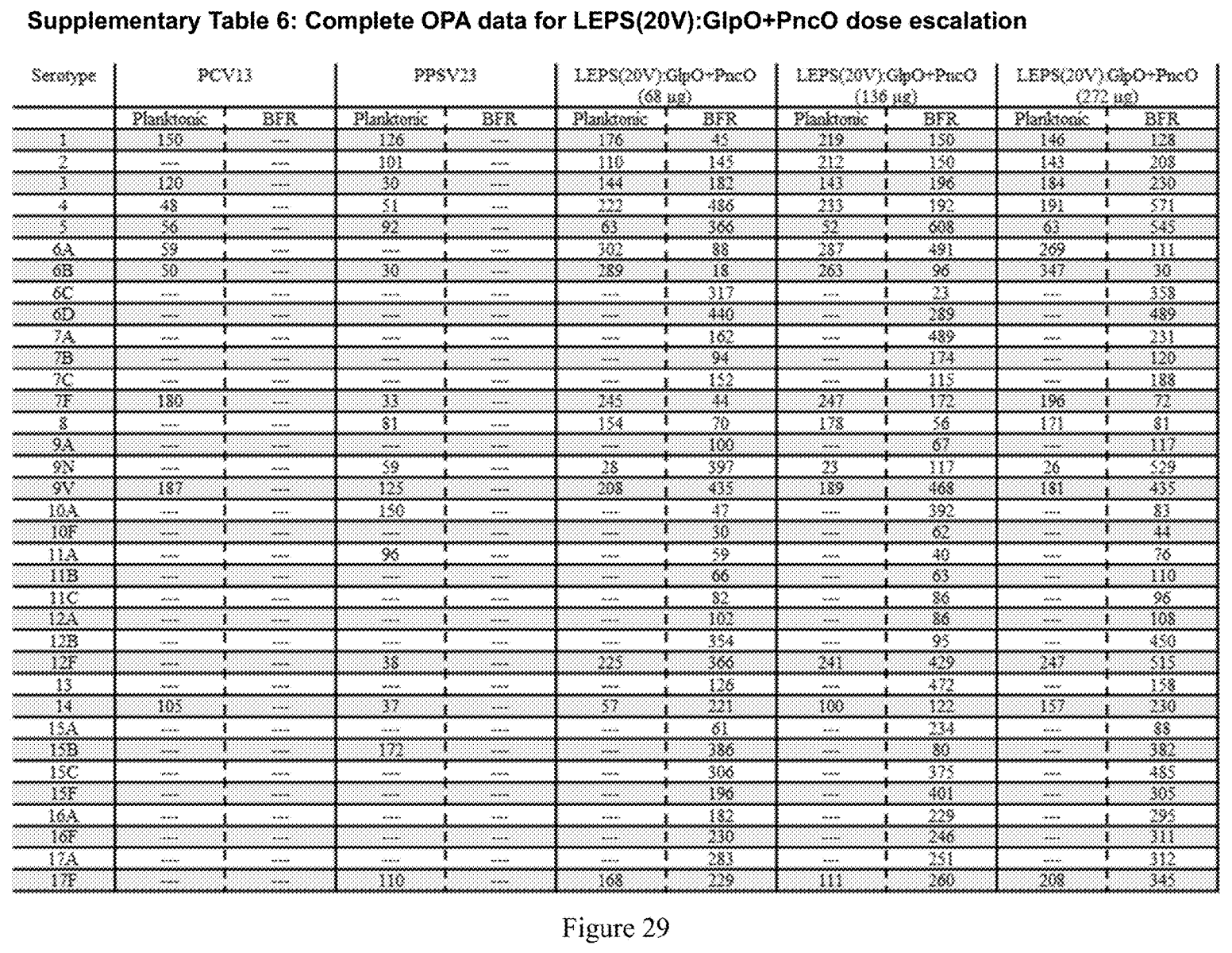
Figure 29:
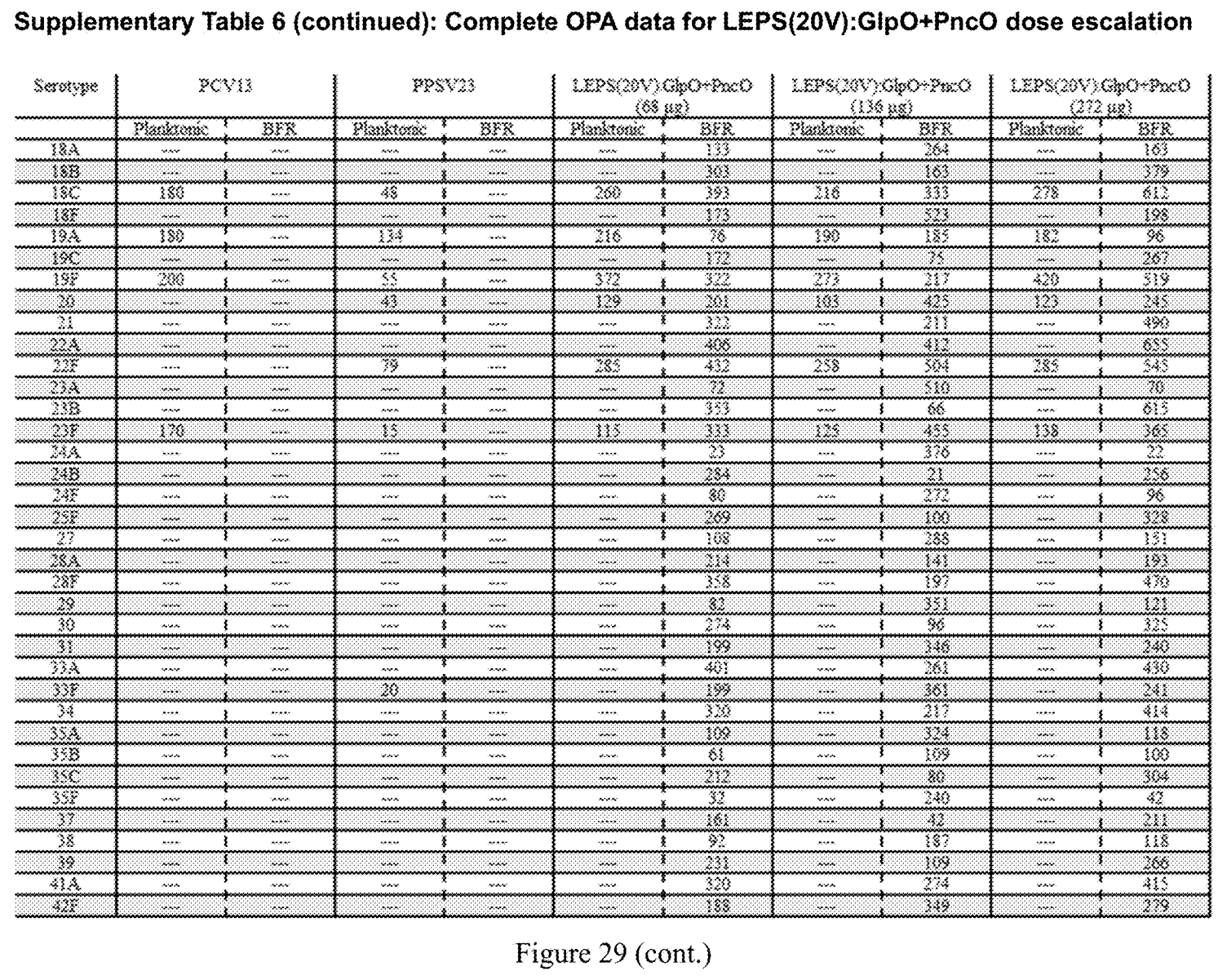

To evaluate immunogenicity, we measured the production and neutralization activity of the antibodies resulting from vaccination. When quantifying antibody titers across the doses for GlpO (FIG. 25), PncO (FIG. 3A-C), and GlpO+PncO (FIG. 26), significant production of antibodies across all CPS and protein antigens was observed. Interestingly, it was found that the relative antibody titers targeting the CPS increased as the protein dose increased from 34 to 68 μg (FIG. 20). However, there was a significant decrease in CPS antibodies when the dose was increased from 68 to 136 μg (FIG. 20). The neutralization activity of these antibodies with OPA assays was then measured using either planktonic or BFR bacteria (Tables 5, 6 (FIGS. 28 and 29 respectively)). Consistent with the observations for antibody titer, the 50% killing dilution for planktonic bacteria decreased when the protein dose was increased to 136 μg. Conversely, the 50% killing dilution for BFR bacteria generally increased with the protein dose. Taken together, these studies indicate that dose escalation of either GlpO or PncO in isolation can serve as an alternative to co-formulation.

PncO Dose Escalation in IAV Pneumonia Challenge Model

Figure 21:
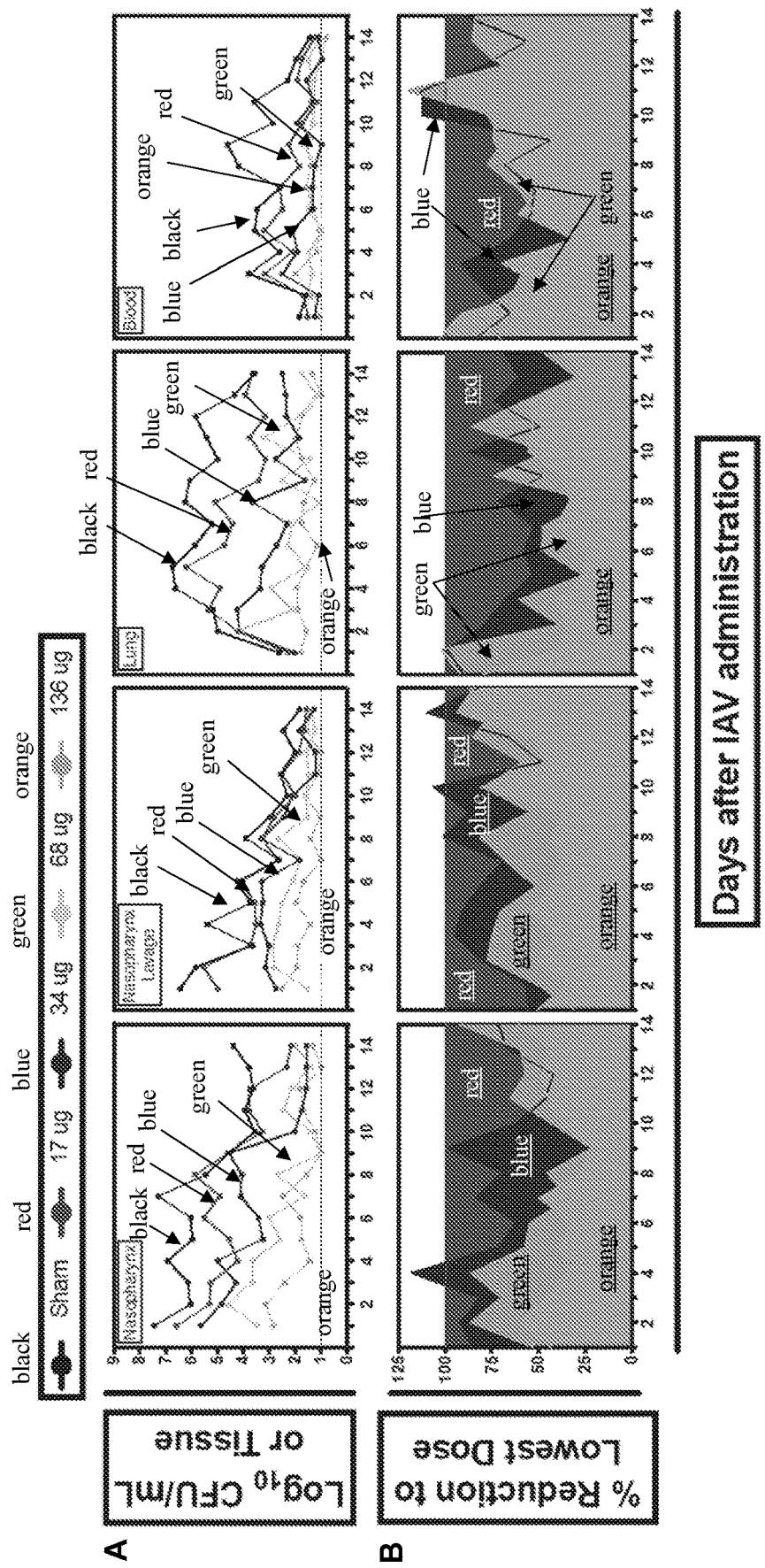
FIG. 21: IAV pneumonia challenge for PncO dose escalation. A) Bacterial load in various physiological locations (nasopharynx, nasopharynx lavage, lung, and blood. B) Effect vaccination on bacterial burden relative to 17 μg dose across physiological location. PncO doses included 17 (red), 34 (blue), 68 (green), and 136 μg (orange) as well as a sham control (black).

Due to concerns with GlpO's off target immunogenicity, we sought additional confirmation of PncO's efficacy as a stand-alone protein using an influenza A virus (IAV) pneumonia challenge model (which mimics in vivo biofilm release of virulent pneumococci). Mice colonized with conditioned EF3030 (19F) Streptococcus pneumoniae were inoculated with IAV to promote bacterial dissemination from the nasopharynx biofilm into the blood and lungs. As shown in FIG. 21, increasing the dose of PncO decreased the bacterial load across each location. Interestingly, vaccination with PncO led to decreased colonization of the nasopharynx following IAV infection. This is likely due to upregulation of PncO caused by the initial conditioning of the bacteria to enhance colonization. Regardless, this study further demonstrates that increasing the dose of PncO beyond our initial dose of 34 µg significantly deters S. pneumoniae propagation and dissemination.

Building a 24-Valent LEPS Vaccine

Figure 22:
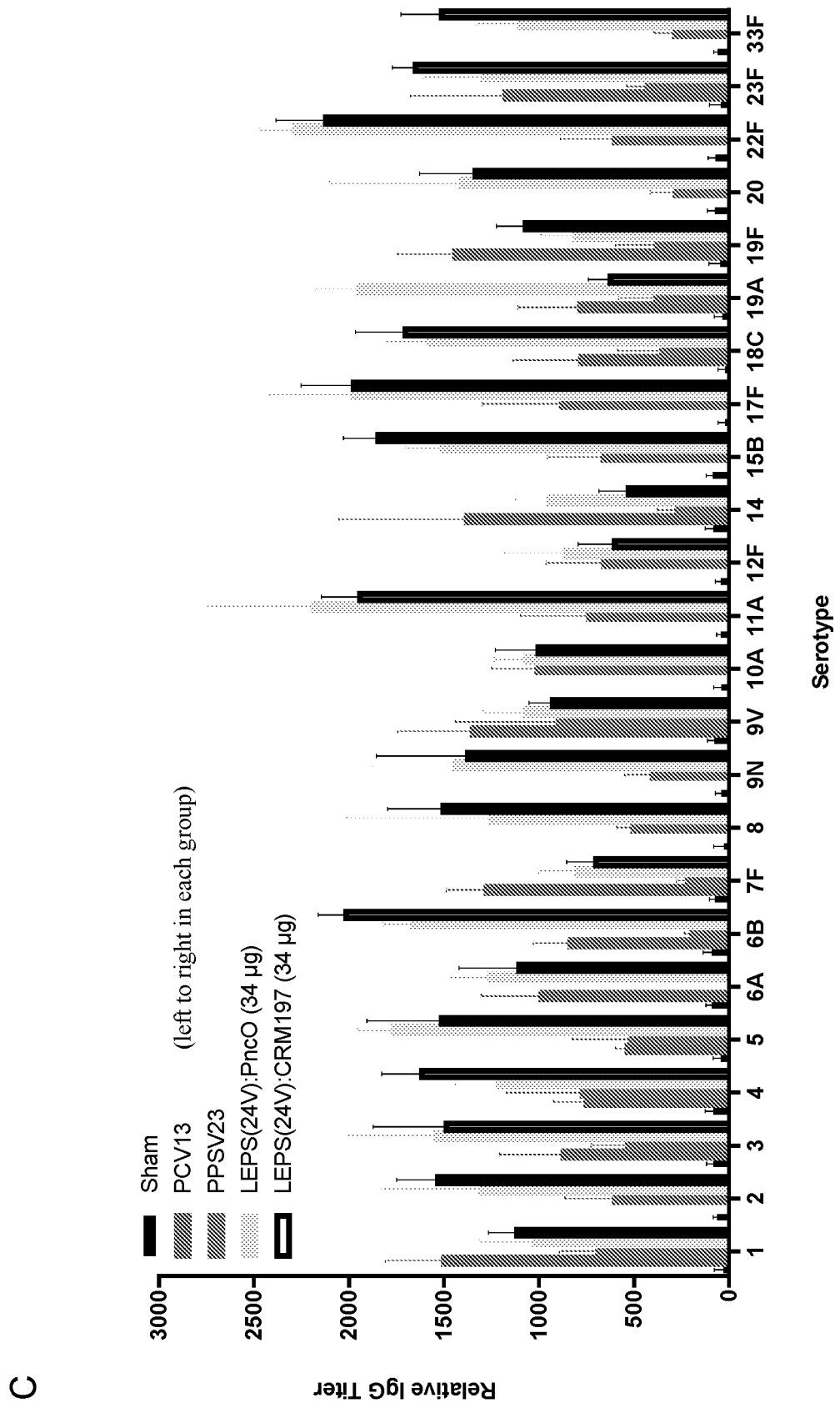
FIG. 22: Expansion of LEPS vaccine to include 10A, 11A, 15B, 33F CPS. A) Relative antibody titers for each CPS post dose 1 (left bar) and post dose 2 (right bar). B) Composition of CPS antibody pool segmented by IgG, IgM, IgA, and IgE post vaccination. C) Relative antibody titers for all 24 CPS included in LEPS(24V) formulation resulting from sham, PCV13, PPSV23, LEPS(24V):PncO, and LEPS (24V)CRM197. Error bars represent the standard deviation of four biological replicates.

To demonstrate the generalizability of the LEPS vaccine platform, we evaluated immunogenicity and OPA levels of four new serotype CPSs introduced into the 20-valent formulation. In particular, the 10A, 11A, 15B, 33F serotypes were selected to encompass all of the serotypes included in currently-used vaccines. Immunogenicity was initially evaluated for each CPS separately as shown in FIG. 21. Potent antibody production and IgM to IgG class shifting was achieved with each CPS (FIGS. 22 A & B). These results suggest further support that the LEPS encapsulation process is generalizable to any pneumococcal CPS.

Following the initial studies evaluating new CPS antigens individually, we combined all four new formulations with our LEPS20V vaccine to create a new 24-valent vaccine (LEPS(24V)). Furthermore, to evaluate the potential loss of immunogenicity resulting from inclusion of the additional CPS, the relative antibody titers across all 24 serotypes was evaluated. As shown in FIG. 22C, LEPS(24V) formulated with either PncO or CRM197 produced significant titers of CPS antibody for all serotypes. Moreover, the measured antibody titers were generally comparable to those obtained for commercially-available vaccines. In addition, an OPA assay was used to measure the neutralization activity of serum obtained from mice vaccinated with the LEPS(24V) formulation. As shown in Table S7 (FIG. 30), both the CRM197 and PncO formulations were able to obtain OPA titers comparable to PCV13 across all shared and unshared serotypes. Taken together, these results indicate that the LEPS formulation strategy is a generalizable and scalable process for assembling a CPS-based vaccine against S. pneumoniae.

Developing Alternative Protein-Liposome Attachment Strategies

A feature of the LEPS platform is the non-covalent surface localization of proteins. As an example, we used his-tagged proteins and lipids containing nickel-NTA. However, though we have not observed any adverse reactions during immunization studies to date, to address any potential toxicity and/or adverse immunogenicity concerns associated with using nickel and his-tagged chelation components, we assessed alternative non-covalent attachment methods for carrier or antigen proteins. Initial alterations included variations in the chelation metal (nickel [$Ni^{2+}$] vs. cobalt [$Co^{2+}$]) or metal scaffold (NTA vs. porphyrin). In addition, two biotin-streptavidin systems were evaluated with both featuring a biotinylated lipid (DSPE-PEG-Biotin) incorporated into the liposome. In one system, denoted "BSB", biotin-containing liposomes were incubated with streptavidin and biotinylated CRM197 to create a biotin-streptavidin-biotin linkage. In the alternative system, biotinylated liposomes were incubated with streptavidin-linked PspA to form a biotin-streptavidin linkage (BS).

Figure 23:
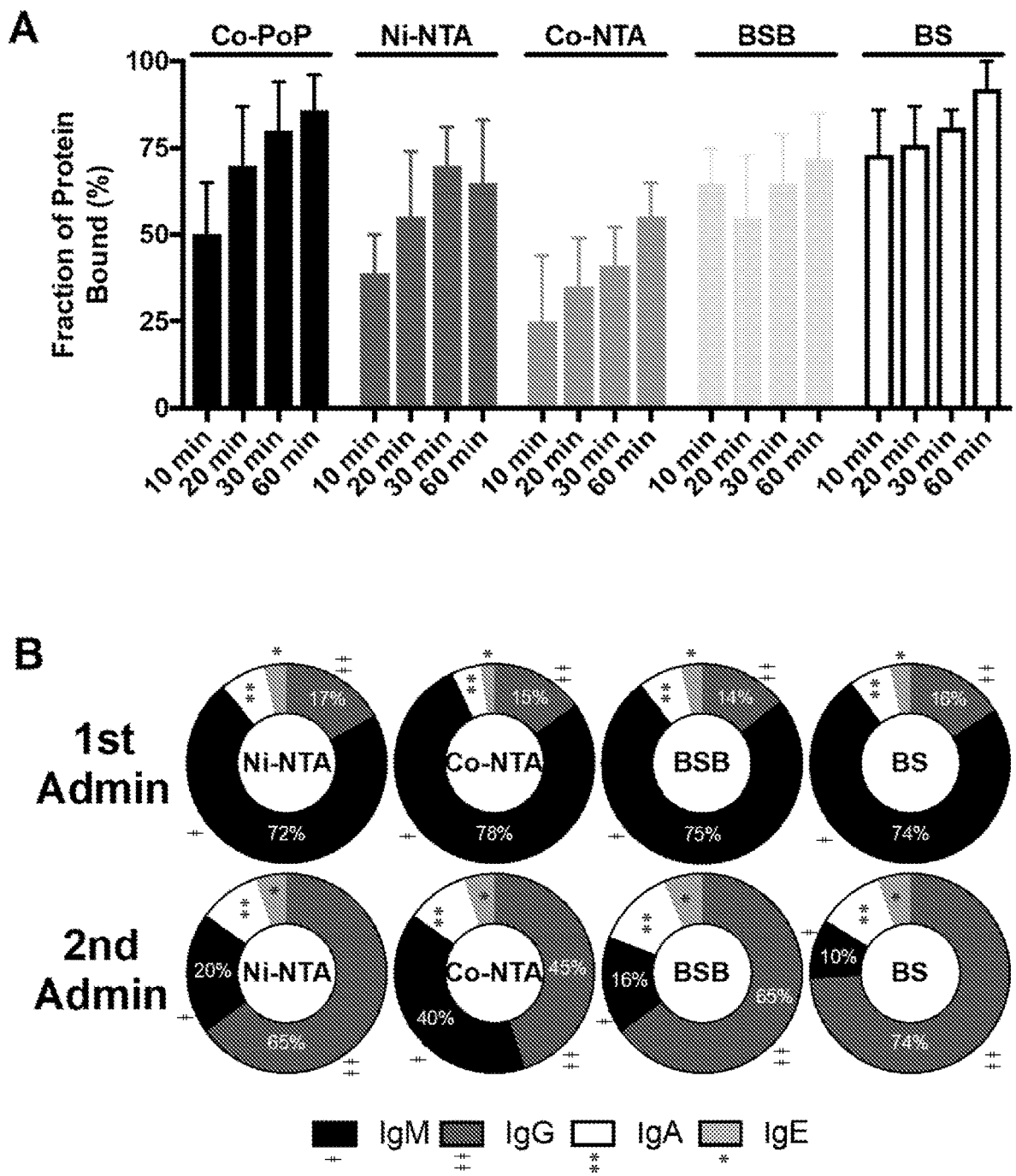
FIG. 23: Characterization of alternative protein-liposome attachment strategies. A) Fraction of protein bound to liposomes as measured by an EMSA assay using Co-PoP, Ni-NTA, Co-NTA, BSB, and BS liposomes. Incubations were conducted for 10, 20, 30, or 60 minutes. Error bars represent the standard deviation of three technical replicates. B) Composition of CPS antibody pool segmented by IgG, IgM, IgA, and IgE post vaccination. C) Relative antibody titer for alternative protein-liposome attachment formulations relative to PCV13 and PPSV23 following the first (left col) and second (right col) administrations. Error bars represent the standard deviation of four biological replicates. D) OPA assay using alternative protein-liposome attachment formulations; dashed line represents 50% killing of bacteria. Vaccinations include a sham, PCV13, PPSV23 as well as Ni-NTA, Co-NTA, BSB, and BS liposomes. Error bars represent the standard deviation of four technical replicates.
Figure 23:
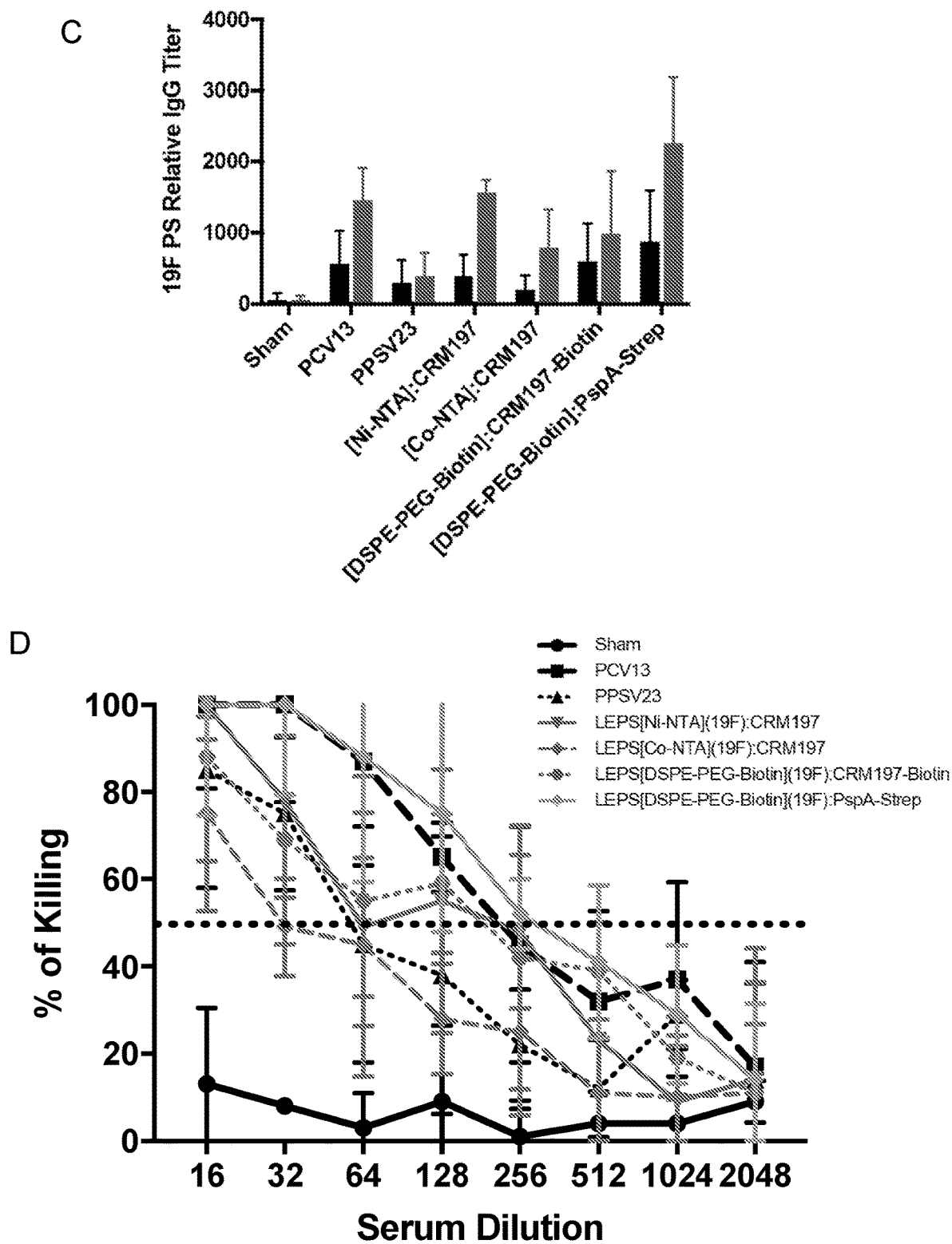

Initially, an electrophoretic mobility shift assay (EMSA) was utilized to measure binding efficiency by determining the fraction of protein bound to the surface of the liposomes. As shown in FIG. 23A, all liposomal variants provided at least 50% protein binding over time and both the BS and BSB strategies demonstrating comparable or enhanced binding relative to metal chelation options across all incubation times. Interestingly, when these formulations were utilized to deliver the 19F CPS, binding efficiency served as a general proxy for immunogenicity. Following immunization of mice, the degree of CPS antibody class shifting (FIG. 23B) and titer (FIG. 23C) correlated with protein binding efficiency for each formulation. Specifically, the BS formulation significantly outperformed Co-NTA in both antibody titer and antibody class shifting. Furthermore, these trends were observed for neutralization activity as measured by an OPA assay (FIG. 23D). Finally, all formulations were characterized using dynamic light scattering to determine liposome size distribution and surface charge. As shown in Table S8 (FIG. 31), properties across liposomal formulations were similar. However, the inclusion of proteins and polysaccharides increased liposome size and the inclusion of proteins resulted in an increased negative charge at the liposome surface. Taken together, these results highlight the flexibility of the LEPS platform to retain efficacy across formulation variations designed to facilitate clinical translation and utility.

Single-Dose Assessment of LEPS Acute Toxicity

To assess the toxicity of the LEPS vaccine, we performed a single-dose escalation study in CD-1 mice to evaluate acute toxicity and identity a maximum tolerated dose (MTD). In these studies, animals were vaccinated with our therapeutic dose (34 µg of protein and 2.2 µg of each CPS) as well as 5 and 10× doses. As shown in Table 1, both male and female mice tolerated up to 10× the therapeutic doses of the proteins and CPS in LEPS. In addition, hematological effects) associated with vaccination were evaluated by measuring metabolite and leukocyte concentrations in blood (Tables 9, 10 (FIGS. 32 and 33 respectively)).

As shown in Table 9 (FIG. 32), the levels of various chemicals in the blood were mostly similar across all doses. Although the concentration of sodium was statistically different across different groups, there was no discernable pattern in its concentration. Similarly, it was observed that concentration of different leukocytes was similarly across all groups (Table S10 (FIG. 33)). In these studies, a slight increase in lymphocytes associated with increasing vaccine doses was observed, suggesting a potential immune response; however, the differences were not statistically different. Although mild reactogenecity occurred upon vaccination, it was limited to initial soreness and irritation that did not cause prolonged distress. Taken together, these results demonstrate that the LEPS vaccine does not demonstrate pronounced acute toxicity in animals.

Discussion:

Although potent vaccines against S. pneumoniae have been developed, incomplete serotype coverage and the potential for breakthrough disease result in a substantial global healthcare burden. This example demonstrates the use of the present LEPS system to meet the challenges of additional serotypes by expanding coverage to 24 serotypes, consolidating to one surface-attached protein antigen (PncO), identifying a suitable amount of protein per dose (e.g., 68 µg) and identifying an alternative attachment strategy. Taken together, these results serve to advance the clinical-readiness of the LEPS system by clarifying the clinical development plan, simplifying manufacturing, and addressing safety concerns.

For example, in this example, we used a GlpO-free vaccine formulation and increased the PncO dose. In addition, we demonstrate that the LEPS vaccine can be functionally assembled through alternative noncovalent protein surface attachment approaches.

Interestingly, we observed a peculiar effect associated with both the increase in protein concentration in vaccination and the binding affinity of alternative protein-to-liposome attachment strategies. Specifically, we observed that increasing the PncO dose from 34 µg to 68 µg improved relative antibody titers for all 20 CPS (Table 11 (FIG. 34)) and improved OPA assay results for 14/20 serotypes (Table S12 (FIG. 35)). This was observed despite the fact that the CPS content remained constant. However, further doubling the PncO content to 136 µg decreased both relative antibody titers and OPA assay performance (Tables S11, S12 (FIGS. 34 and 35 respectively)). Intermediate protein concentrations, effectively increasing the concentration of protein at the surface, may also provide effective provoking of immune response.

Materials and Methods

Bacterial and Cellular Strains to be Used in Study (All Inclusive)

S. pneumoniae strains in this study included the >70 serotypes and S. pneumoniae EF3030 (serotype 19F) as a control in OPA and immunofluorescence studies. Bacterial species listed in Supplementary Table 1 were used in microflora studies which included OPA and immunofluorescence assays. NCI-H292 epithelial cells (CRL1849, American Type Culture Collection (ATCC)) were utilized to support biofilm growth. Human HL60 cells were differentiated for use in the standard and modified OPA studies.

Homology Search Description

Conservation of glpO homologs in commensal bacteria species (Supplementary Table 1) was calculated by accounting for gap and mismatches in commensal bacteria amino acid sequences, available in BLAST (blast.ncbi.nlm.nih.gov). Surface accessibility was established using the InterPro database (ebi.ac.uk/interpro) and epitope regions were predicted with the bepipred linear epitope prediction method using IEDB Analysis Resource (tools.immuneepitope.org/bcell). The reference glpO sequence used for this study was S. pneumoniae D39 (accession CP000410.1).

Bacterial Growth and Seeding

The S. pneumoniae strains used in this study were initially grown on Todd-Hewitt agar plates supplemented with 0.5% yeast extract and 5% (vol vol$^{-1}$) sheep blood and were incubated overnight at 37° C. Single colonies were transferred to 5 mL of Todd-Hewitt broth containing 0.5% yeast extract and were incubated at 37° C. to an $OD_{600}$ of 0.6. Bacteria were then diluted 1:10 in chemically defined medium (CDM) to an $OD_{600}$ of approximately 0.5 mL, which was then added to each well of a 24-well plate containing a layer of fixed H292 cells. Alternatively, cultured planktonic S. pneumoniae were collected by centrifugation, washed once with and resuspended in PBS, and quantified by $OD_{600}$ measurement for experiments requiring planktonic cells.

H292 Cell Growth and Fixation

NCI-H292 epithelial cells were first cultured in RPMI 1640 with the addition of fetal bovine serum (FBS) in T75 flasks at 37° C. and 5% $CO_2$. Upon reaching 100% confluency, media was removed and cells were incubated with Trypsin-EDTA solution until the cell layer was dispersed. Cells were then collected via centrifugation and diluted 1:8 in RPMI 1640 with FBS and transferred to 24-well plates and grown as described above until reaching 100% confluency. After reaching 100% confluency, H292 cells washed three times with PBS, prefixed in 4% buffered paraformaldehyde at 34° C. for 48 hours, and washed three times with PBS.

Biofilm Growth and Release

CDM-grown pneumococci were seeded onto fixed H292 cells as described above and incubated at 37° C. for 48 hours unless otherwise specified. Throughout the biofilm growth phase, medium was changed every 12 hours. To promote biofilm-release of pneumococci, biofilms were exposed to heat (38.5° C.) for 4 hours unless otherwise specified. All releases were conducted at the same time to reduce variability. Released cells were then collected by centrifugation, washed once with and resuspended in PBS, and quantified by $OD_{600}$ measurement. These biofilm-released cells were then used in the pneumococcal disease pneumonia and sepsis models.

Protein Production and Purification

All proteins [CRM197, GlpO, PncO, PspA] were recombinantly produced with polyhistidine or streptavididin tags using Escherichia coli (BL21(DE3)). Bacterial strains were initially inoculated into 3 mL of lysogeny broth and grown overnight. Bacteria were then transferred into 1 L of lysogeny broth and grown until an $OD_{600}$ of 0.4 to 0.6 was reached. Protein production was subsequently induced using 1 mM isopropyl β-D-1-thiogalactopyranoside (IPTG) and cultures were incubated overnight at 22° C. Protein purification proceeded through disruption of cells using a French press and by passing cell lysate over a fast protein liquid chromatography column (GE Healthcare HisTrap HP, 1×1 ml and XXXX). Final protein products were quantified using the Pierce Micro BCA Protein Assay kit.

LEPS Formulation and Assembly

LEPS vectors were formulated as follows. LEPS carriers, which had a total lipid mass of 500 µg, were composed of DOPC/DOPG/DOGS-NTA-Ni/cholesterol/DSPE-PEG2000 at a molar ratio of 3:3:1:4:0.1 unless otherwise specified. Lipids were dissolved in chloroform, sonicated for one minute, and then evaporated to form a film using a rotary evaporator. This film was rehydrated using a phosphate-buffered saline (PBS) containing a single capsular polysaccharide antigen to form the liposomal carrier. These particles were then passed through a handheld extruder (10-12 times) with a pore size of 200 nm. Twenty (or twenty-four) individually prepared LEPS samples, each containing a different CPS, were incubated with protein antigens (CRM197, GlpO, PncO, or PspA) containing a polyhistidine or strep tag for 30 min at 4° C. to facilitate surface binding via polyhistidine tag-Ni chelation. Unbound proteins or unencapsulated CPs were removed via overnight dialysis in PBS at 4° C. All samples were then combined to form the final 20- or 24-valent LEPS variants. The 20 valent formulation contained 20-valent: 1, 2, 3, 4, 5, 6A, 6B, 7F, 8, 9N, 9V, 12F, 14, 17F, 18C, 19A, 19F, 20, 22F, and 23F. The 24 valent formulation contained 1, 2, 3, 4, 5, 6A, 6B, 7F, 8, 9N, 9V, 10A, 11A, 12F, 14, 15B, 17F, 18C, 19A, 19F, 20, 22F, 23F, and 33F.

Alternatively, the liposomes formulated to facilitate biotin-streptavidin linkages were composed of DOPC/DOPG/DOGS-NTA-Ni/cholesterol/DSPE-PEG-Biotin at a molar ratio of 3:3:1:4:0.1. Liposomal particles were assembled as described above using either streptavidin and biotinylated protein or streptavidin-conjugated protein. These incubations were carried out for various durations and binding the fraction of protein bound was determined using an EMSA assay. For subsequent studies with alternative liposomes, particles assembled using a 30-minute incubation were used.

Electrophoretic Mobility Shift Assay

EMSA experiments were performed with 2.5 µg protein incubated with 50 µg liposomes followed by electrophoresis in a 0.75% agarose gel with 50 V applied for 90 minutes and imaging with an IVIS Lumina II system with the indicated excitation and emission filters. For EMSA serum stability test, 3 µg protein was pre-incubated with 60 µg liposome in 40 µL PBS. After 24 h incubation, 40 µL fetal bovine serum (FBS, VWR #82013-602) was added and incubated for another 8 h. For imidazole displacement experiments, 1 µg of reporter protein was bound to 20 µg liposomes in PBS. Imidazole was then titrated and binding was assessed with fluorescence. For serum stability, 1 µg of reporter protein was bound to 20 µg liposomes in 100 µL PBS and then an equal volume of FBS was added and binding was monitored with fluorescence. Peptide binding was assessed with RGD-His FAM fluorophore quenching following incubation of 500 ng peptide with 20 µg liposomes.

Animal Immunization and Collection of Serum

Outbred 6-week-old male and female CD-1 mice were used in immunization experiments. Mice were immunized via subcutaneous injection (200 µL). However, during toxicological assessments, mice were immunized intramuscularly. The background solution used for the formulations was PBS ("sham" negative controls were background solutions administered without antigen components). Final protein antigen concentrations were escalated with the following concentrations: 34, 68, and 136 µg. When combined, GlpO and PncO were administered at concentrations of 68, 136, and 272 µg. As positive controls, mice were also immunized with PCV13 or PPSV23 as described previously (REF). On day 14 post-immunization, mice were boosted with the same formulations. On day 14 and day 28 post-immunization, serum samples were collected from the mice via retro-orbital bleeding for antibody and OPA analysis.

Measurement of Antibody Titers and Classes

Antigen antibody titer analysis was conducted as described previously (Li, Y. et al. Science Advances 2, doi:10.1126/sciadv.1600264 (2016), with the method extended to include 20 polysaccharides from associated serotypes and the GlpO nd PncO protein antigens. Thus, an analysis was extended to all antigens used in the study.

Standard OPA assay

Extending upon a previous protocol (Romero-Steiner, S. et al. Clinical and Vaccine Immunology 13, 165-169, doi: 10.1128/CVi.13.2.165-169.2006), human HL60 cells were differentiated with dimethlyformamide to quantify antibody-mediated opsonophagocytosis and killing of S. pneumoniae exposed to dilutions of sera collected from immunized mice subjects to identify the 50% killing end point (quantified by CFU counts). HL60 cells and pneumococci were incubated for 75 min.

BFR-Modified OPA Assay

The standard OPA assay was modified to quantify antibody-mediated opsonophagocytosis and killing of BFR S. pneumoniae. This was done by replacing the planktonic S. pneumoniae with BFR bacteria, which were then exposed to dilutions of sera collected from immunized mice subjects to identify the 50% killing end-point (quantified by CFU counts). HL60 cells and pneumococci were incubated for 75 min.

OPA Assay Using Microflora Bacteria

Using the standard OPA assay described above, the antibody-mediated opsonophagocytosis and killing of the commensal bacteria (shown in FIG. 18A), or S. pneumoniae EF303 (positive control), when exposed to dilutions of sera collected from mice subjects immunized with GlpO. This was done to identify the 50% killing end-point (quantified by CFU counts). HL60 cells and bacterial cells were incubated for 75 min.

Pneumococcal Challenge Models (BFR Pneumonia, IAV Pneumonia)

BFR pneumonia: Mice were challenged with $1\times10^6$ (pneumonia model) CFU of pneumococci strains through intranasal (with isoflurane) administration. Mice were monitored every four hours for signs of morbidity (huddling, ruffled fur, lethargy, and abdominal surface temperature). Mice found to be moribund were euthanized via $CO_2$ asphyxiation and cervical dislocation.

IAV pneumonia: To induce colonization, mice were administered with $1\times10^6$ CFU of mouse passaged S. pneumoniae EF3030 intranasally, without isoflurane. To mimic influenza-induced pneumonia, pneumococci colonization was followed by intranasal inoculation with 40 plaque-forming units of IAV. The mouse-adapted IAV strain A/PR/8/34 (H1N1) (ATCC VR-95) was used, and titers were determined by plaque assays. Mice were monitored every four hours for signs of morbidity (huddling, ruffled fur, lethargy, and abdominal surface temperature). Mice found to be moribund were euthanized via $CO_2$ asphyxiation and cervical dislocation.

Bacterial Load Assessment

At predefined time points (24 and 48 hours after infection for intraperitoneal and intranasal challenges, respectively) or upon becoming moribund, mice were euthanized (as described previously), and a combination of nasopharynx tissue, nasopharyngeal lavage fluid, lung, liver, spleen, and blood samples was collected and assessed for bacterial burden. Tissue and organ samples, lavage fluid, and blood were homogenized (on a setting of 10 for 30 s or until homogenized completely; Tissue-Tearor, BioSpec Products Inc.) to ensure dissociation of bacterial aggregates and then were serially diluted on tryptic soy and 5% blood agar plates before enumeration.

Immunofluorescence Assay

Serum from GlpO-vaccinated mice was diluted at ratios of 1:10, 1:100, and 1:1000 and were incubated in 96 well plates with the bacterial strains utilized in the study to quantify off-target GlpO effects (Table S4 (FIG. 27)) with $10^5$ bacterial cells per well at 25° C. for one hour. The plate was then blocked with 3% bovine serum albumin in for 1 hour at 25° C. After binding, unbound antibodies were removed by washing with PBS and cells were then incubated with the secondary antibody (anti-mouse IgG) conjugated with alkaline phosphatase for one hour at 25° C. Unbound antibody was removed through PBS washes and p-nitrophenylphosphate was added to develop the signal and the reaction was quenched using 0.75 M NaOH. The signal was detected using a plate reader spectrophotometer at an absorbance of 405 nm.

Toxicology Study Design and Conduct

Outbred 6-week male and female CD-1 mice were obtained from Charles River. Mice were injected intramuscularly with LEPS(20V):CRM197 or alum:PncO where both CRM and PncO were formulated at 1, 5, and 10× of the initial dose (34 μg). Both before and two days after dose administration, blood samples were taken to hematological assessment. For two weeks after immunization, mice were monitored for weight and behavioral changes. Mice were sacrificed 14 days after immunization via $CO_2$ asphyxiation followed by cervical dislocation and vital organs were harvested and weighed.

Hematological Assessment of Blood Chemistry and Cells

Outbred 6-week male and female CD-1 mice were obtained from Charles River. Mice were injected with LEPS (20V):CRM197 or alum:PncO where both CRM197 and PncO were administered at 1, 5, and 10× of the initial dose (12.5 μg). Blood samples were collected via retro orbital bleeding approximately 6 hours before and 2 days after immunization. The blood samples were subjected to MASCOT hematology profiling (Drew Scientific) according to the manufacturer protocol.

While the disclosure has been described through various embodiments, routine modifications will be apparent to those skilled in the art, and such modifications are intended to be within the scope of the disclosure.

TABLE 1

Body and organ weights of mice post vaccination

| Animal | Sham | Alum:PncO | | | LEPS(20V):CRM197 | | |
|---|---|---|---|---|---|---|---|
| Terminal Weight | — | 1X | 5X | 10X | 1X | 5X | 10X |
| Male CD-1 Mice (N = 5) | | | | | | | |
| Body Weight (g) | 30.3 ± 3.1 | 30.6 ± 2.1 | 29.7 ± 2.3 | 31.8 ± 2.4 | 31.5 ± 2.9 | 30.3 ± 1.8 | 31.5 ± 2.5 |
| Brain Weight (mg) | 472.0 ± 26 | 426.6 ± 20 | 472.0 ± 25 | 463.4 ± 26 | 467.8 ± 16 | 472.6 ± 19 | 468.6 ± 20 |
| Lung Weight (mg) | 180.0 ± 15 | 185.4 ± 23 | 174.6 ± 25 | 174.6 ± 6 | 171.0 ± 17 | 185.4 ± 18 | 171.0 ± 15 |
| Heart Weight (mg) | 175.0 ± 23 | 169.8 ± 15 | 180.3 ± 28 | 166.2 ± 17 | 171.5 ± 15 | 173.3 ± 26 | 182.0 ± 21 |
| Liver Weight (g) | 1.8 ± 0.23 | 1.8 ± 0.22 | 1.8 ± 0.18 | 1.8 ± 0.25 | 1.7 ± 0.17 | 1.9 ± 0.15 | 1.7 ± 0.3 |
| Kidney Weight (mg) | 440.0 ± 62 | 422.4 ± 30 | 421.3 ± 41 | 453.3 ± 20 | 465.1 ± 32 | 453.2 ± 31 | 449.7 ± 22 |
| Female CD-1 Mice (N = 5) | | | | | | | |
| Body Weight (g) | 26.0 ± 1.5 | 27.0 ± 2.8 | 25.7 ± 2.8 | 26.3 ± 1.7 | 26.3 ± 2.3 | 26.7 ± 2.5 | 26.5 ± 2.1 |
| Brain Weight (mg) | 460.0 ± 20 | 469.2 ± 28 | 433.4 ± 17 | 446.2 ± 30 | 461.1 ± 17 | 473.8 ± 16 | 455.4 ± 17 |
| Lung Weight (mg) | 170.0 ± 21 | 176.8 ± 25 | 161.5 ± 20 | 173.4 ± 25 | 178.5 ± 23 | 161.5 ± 30 | 173.4 ± 16 |
| Heart Weight (mg) | 150.0 ± 20 | 156.0 ± 25 | 154.5 ± 27 | 157.5 ± 29 | 144.0 ± 30 | 148.5 ± 29 | 145.5 ± 19 |
| Liver Weight (g) | 1.3 ± 0.11 | 1.3 ± 0.29 | 1.3 ± 0.26 | 1.3 ± 0.15 | 1.2 ± 0.16 | 1.3 ± 0.23 | 1.3 ± 0.18 |
| Kidney Weight (mg) | 280.0 ± 33 | 282.8 ± 55 | 282.8 ± 28 | 280.0 ± 51 | 294.0 ± 27 | 294.0 ± 37 | 282.2 ± 53 |

What is claimed is:

1. A vaccine composition comprising liposomes, wherein at least some of the liposomes in the composition encapsulate capsular polysaccharides from one or more serotypes of *Streptococcus pneumoniae* and have one or more proteins attached to the surface via non-covalent attachment such that at least some portion of the protein is displayed on the surface to the exterior of the liposomes.

2. A vaccine composition comprising a plurality of sets of liposomes, wherein each liposome within a set encapsulates the same serotype which is different from the serotypes of other sets, and wherein at least some of the liposomes in the composition have one or more proteins attached to the surface via non-covalent attachment such that at least some portion of the protein is displayed on the surface to the exterior of the liposomes.

3. The vaccine composition of claim 1, wherein the serotypes are selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F.

4. The vaccine composition of claim 1, wherein the serotypes are selected from the group consisting of 1, 2, 3, 4, 5, 6A, 6B, 7F, 8, 9N, 9V, 12F, 14, 17F, 18C, 19A, 19F, 20, 22F, and 23F.

5. The vaccine composition of claim 1, wherein at least a plurality of liposomes encapsulate a first type of capsular polysaccharide, and at least a plurality of liposomes encapsulate a second type of capsular polysaccharide.

6. The vaccine composition of claim 1, wherein the protein is CRM197.

7. The vaccine composition of claim 1, wherein the protein is PnCo.

8. The vaccine composition of claim 7, wherein PncO is the only protein non-covalently attached to the liposome.

9. The vaccine composition of claim 7, wherein PncO is attached to the liposome via streptavidin-biotin linkage.

10. The vaccine composition of claim 1, wherein the protein comprises a poly histidine tag and the protein non-covalently attaches to the liposome via a metal present in the liposomal bilayer.

11. A method of immunizing an individual against *Streptococcus pneumoniae* comprising administering to the individual the vaccine composition of claim 1.

12. The method of claim 11, wherein the vaccine composition comprises a plurality of sets of liposomes, each set of liposomes encapsulating the same type of serotype, which is different from the serotype encapsulated in another set of liposomes, wherein at least some of the liposomes in the composition have one or more proteins attached to the surface via non-covalent attachment such that at least some portion of the protein is displayed on the surface to the exterior of the liposomes.

13. The method of claim 12, wherein the composition comprises at least 20 sets of liposomes and 20 sets of liposomes collectively encapsulate the following serotypes: 1, 2, 3, 4, 5, 6A, 6B, 7F, 8, 9N, 9V, 12F, 14, 17F, 18C, 19A, 19F, 20, 22F, and 23F.

14. The method of claim 12, wherein the composition comprises at least 24 sets of liposomes and 24 sets of liposomes collectively encapsulate the following serotypes: 1, 2, 3, 4, 5, 6A, 6B, 7F, 8, 9N, 9V, 10A, 11A, 12F, 14, 15B, 17F, 18C, 19A, 19F, 20, 22F, 23F, and 33F.

15. The method of claim 11, wherein the protein is CRM197.

16. The method of claim 11, wherein the protein is PnCo.

17. The method of claim 16, wherein the PncO is non-covalently attached to the liposome via streptavidin-biotin linkage.

18. A method of making a vaccine composition of claim 2 comprising separately preparing a plurality of sets of liposomes, the liposomes in each set encapsulating a unique capsular polysaccharide, and then mixing the plurality of sets of liposomes to obtain the vaccine composition, and further comprising non-covalently attaching a protein to the surface of at least some of the liposome such that at least a portion of the protein is exposed to the exterior of the liposomes.

19. The method of claim 18, wherein at least some of the sets of liposomes encapsulate capsular polysaccharides selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F of *S. pneumoniae*.

20. The method of claim 18, wherein the protein is CRM197 or PncO.

* * * * *

SEQUENCE LISTING

<160> NUMBER OF SEQ ID NOS: 2

<210> SEQ ID NO 1
<211> LENGTH: 229
<212> TYPE: PRT
<213> ORGANISM: Streptococcus pneumoniae

<400> SEQUENCE: 1

Met Lys Lys Tyr Gln Leu Leu Phe Lys Ile Ser Ala Val Phe Ser Tyr
1               5                   10                  15

Leu Phe Phe Val Phe Gly Leu Ser Gln Leu Thr Leu Ile Val Gln Asn
            20                  25                  30

Tyr Trp Gln Phe Ser Ser Gln Ile Gly Asn Phe Val Trp Ile Gln Asn
        35                  40                  45

Ile Leu Ser Leu Leu Phe Ser Gly Val Met Ile Trp Ile Leu Val Lys
    50                  55                  60

Thr Gly His Gly Tyr Leu Phe Arg Ile Pro Arg Lys Lys Trp Leu Trp
65                  70                  75                  80

Tyr Ser Ile Leu Thr Val Leu Val Val Leu His Ile Ser Phe Asn
                85                  90                  95

Val Gln Thr Ala Lys His Val Gln Ser Thr Ala Glu Gly Trp Asn Val
            100                 105                 110

Leu Ile Gly Tyr Ser Gly Thr Asn Phe Ala Glu Leu Gly Ile Tyr Val
        115                 120                 125

Thr Leu Phe Phe Leu Thr Pro Leu Met Glu Glu Leu Ile Tyr Arg Gly
    130                 135                 140

```
Leu Leu Gln His Ala Phe Phe Lys His Ser Arg Phe Gly Leu Asp Leu
145                 150                 155                 160

Leu Leu Pro Ser Ile Leu Phe Ala Leu Pro His Phe Leu Ser Leu Pro
                165                 170                 175

Ser Leu Leu Asp Ile Phe Val Phe Ala Thr Phe Gly Ile Ile Phe Ala
            180                 185                 190

Gly Leu Thr Arg Tyr Thr Lys Ser Ile Tyr Pro Ser Tyr Ala Val His
        195                 200                 205

Val Ile Asn Asn Ile Val Ala Thr Phe Pro Phe Leu Leu Thr Phe Leu
210                 215                 220

His Arg Val Leu Gly
225

<210> SEQ ID NO 2
<211> LENGTH: 608
<212> TYPE: PRT
<213> ORGANISM: Streptococcus pneumoniae

<400> SEQUENCE: 2

Met Glu Phe Ser Lys Lys Thr Arg Glu Leu Ser Ile Lys Lys Met Gln
1               5                   10                  15

Glu Arg Thr Leu Asp Leu Leu Ile Ile Gly Gly Ile Thr Gly Ala
            20                  25                  30

Gly Val Ala Leu Gln Ala Ala Ser Gly Leu Glu Thr Gly Leu Ile
        35                  40                  45

Glu Met Gln Asp Phe Ala Glu Gly Thr Ser Ser Arg Ser Thr Lys Leu
50                  55                  60

Val His Gly Gly Leu Arg Tyr Leu Lys Gln Phe Asp Val Glu Val Val
65                  70                  75                  80

Ser Asp Thr Val Ser Glu Arg Ala Val Val Gln Gln Ile Ala Pro His
                85                  90                  95

Ile Pro Lys Pro Asp Pro Met Leu Leu Pro Val Tyr Asp Glu Asp Gly
            100                 105                 110

Ala Thr Phe Ser Leu Phe Arg Leu Lys Val Ala Met Asp Leu Tyr Asp
        115                 120                 125

Leu Leu Ala Gly Val Ser Asn Thr Pro Thr Ala Asn Lys Val Leu Ser
130                 135                 140

Lys Asp Gln Val Leu Glu Arg Gln Pro Asn Leu Lys Lys Glu Gly Leu
145                 150                 155                 160

Val Gly Gly Gly Val Tyr Leu Asp Phe Arg Asn Asn Asp Ala Arg Leu
                165                 170                 175

Val Ile Glu Asn Ile Lys Arg Ala Asn Gln Asp Gly Ala Leu Ile Ala
            180                 185                 190

Asn His Val Lys Ala Glu Gly Phe Leu Phe Asp Glu Ser Gly Lys Ile
        195                 200                 205

Thr Gly Val Val Ala Arg Asp Leu Leu Thr Asp Gln Val Phe Glu Ile
210                 215                 220

Lys Ala Arg Leu Val Ile Asn Thr Thr Gly Pro Trp Ser Asp Lys Val
225                 230                 235                 240

Arg Asn Leu Ser Asn Lys Gly Thr Gln Phe Ser Gln Met Arg Pro Thr
                245                 250                 255

Lys Gly Val His Leu Val Val Asp Ser Ser Lys Ile Lys Val Ser Gln
            260                 265                 270

Pro Val Tyr Phe Asp Thr Gly Leu Gly Asp Gly Arg Met Val Phe Val
        275                 280                 285
```

```
Leu Pro Arg Glu Asn Lys Thr Tyr Phe Gly Thr Thr Asp Thr Asp Tyr
    290                 295                 300

Thr Gly Asp Leu Glu His Pro Lys Val Thr Gln Glu Asp Val Asp Tyr
305                 310                 315                 320

Leu Leu Gly Ile Val Asn Asn Arg Phe Pro Glu Ser Asn Ile Thr Ile
                325                 330                 335

Asp Asp Ile Glu Ser Ser Trp Ala Gly Leu Arg Pro Leu Ile Ala Gly
                340                 345                 350

Asn Ser Ala Ser Asp Tyr Asn Gly Gly Asn Asn Gly Thr Ile Ser Asp
            355                 360                 365

Glu Ser Phe Asp Asn Leu Ile Ala Thr Val Glu Ser Tyr Leu Ser Lys
    370                 375                 380

Glu Lys Thr Arg Glu Asp Val Glu Ser Ala Val Ser Lys Leu Glu Ser
385                 390                 395                 400

Ser Thr Ser Glu Lys His Leu Asp Pro Ser Ala Val Ser Arg Gly Ser
                405                 410                 415

Ser Leu Asp Arg Asp Asp Asn Gly Leu Leu Thr Leu Ala Gly Gly Lys
                420                 425                 430

Ile Thr Asp Tyr Arg Lys Met Ala Glu Gly Ala Met Glu Arg Val Val
            435                 440                 445

Asp Ile Leu Lys Ala Glu Phe Asp Arg Ser Phe Lys Leu Ile Asn Ser
    450                 455                 460

Lys Thr Tyr Pro Val Ser Gly Gly Glu Leu Asn Pro Ala Asn Val Asp
465                 470                 475                 480

Ser Glu Ile Glu Ala Phe Ala Gln Leu Gly Val Ser Arg Gly Leu Asp
                485                 490                 495

Ser Lys Glu Ala His Tyr Leu Ala Asn Leu Tyr Gly Ser Asn Ala Pro
            500                 505                 510

Lys Val Phe Ala Leu Ala His Ser Leu Glu Gln Ala Pro Gly Leu Ser
    515                 520                 525

Leu Ala Asp Thr Leu Ser Leu His Tyr Ala Met Arg Asn Glu Leu Ala
    530                 535                 540

Leu Ser Pro Val Asp Phe Leu Leu Arg Arg Thr Asn His Met Leu Phe
545                 550                 555                 560

Met Arg Asp Ser Leu Asp Ser Ile Val Glu Pro Val Leu Asp Glu Met
                565                 570                 575

Gly Arg Phe Tyr Asp Trp Thr Glu Glu Glu Lys Ala Thr Tyr Arg Ala
                580                 585                 590

Asp Val Glu Ala Ala Leu Ala Asn Asn Asp Leu Ala Glu Leu Lys Asn
            595                 600                 605
```